US012797015B2

(12) United States Patent
Howard

(10) Patent No.: US 12,797,015 B2
(45) **Date of Patent: *Nov. 17, 2026**

(54) DETECTION OF DISEASE CONDITIONS AND COMORBIDITIES

(71) Applicant: Genesis Intelligence, LLC, Jacksonville, FL (US)

(72) Inventor: Newton Howard, Washington, DC (US)

(73) Assignee: Genesis Intelligence, LLC, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/377,648

(22) Filed: Nov. 3, 2025

(65) Prior Publication Data

US 2026/0060621 A1 Mar. 5, 2026

Related U.S. Application Data

(63) Continuation of application No. 17/066,828, filed on Oct. 9, 2020, now Pat. No. 12,458,299, which is a (Continued)

(51) Int. Cl.
*G16H 10/60* (2018.01)
*A61B 5/00* (2006.01)
(Continued)

(52) U.S. Cl.
CPC .......... *A61B 5/7282* (2013.01); *A61B 5/0077* (2013.01); *A61B 5/11* (2013.01); *A61B 5/165* (2013.01); *A61B 5/372* (2021.01); *A61B 5/4088* (2013.01); *A61B 5/4803* (2013.01); *A61B 5/7267* (2013.01); *G16H 10/60* (2018.01); *G16H 20/70* (2018.01); *G16H 70/60* (2018.01)

(58) Field of Classification Search
CPC ... A61B 5/7282; A61B 5/0077; A61B 5/0476; A61B 5/11; A61B 5/165; A61B 5/4088; A61B 5/4803; A61B 5/7267; G16H 10/60; G06F 19/324
See application file for complete search history.

(56) References Cited

U.S. PATENT DOCUMENTS

| | | | |
|---|---|---|---|
| 4,644,959 | A | 2/1987 | Calmanovici |
| 6,159,015 | A | 12/2000 | Buffington et al. |

(Continued)

FOREIGN PATENT DOCUMENTS

| | | | |
|---|---|---|---|
| WO | 2011127424 | A1 | 10/2011 |

*Primary Examiner* — Shirley X Jian
(74) *Attorney, Agent, or Firm* — Neo IP

(57) ABSTRACT

A new computational approach may provide improved detection of disease conditions and comorbidities, such as PTSD, Parkinson's, Alzheimer's, depression, etc. For example, in an embodiment, a computer-implemented method for detecting a disease condition may comprise receiving a plurality of data streams, each data stream representing a measurement of a brain activity comprising physical and chemical phenomena and performing pattern analysis on the plurality of data streams to detect at least one fundamental code unit of a brain code corresponding to a disease condition based on a combination of the plurality of data streams.

19 Claims, 33 Drawing Sheets

Related U.S. Application Data continuation of application No. 15/431,550, filed on Feb. 13, 2017, now Pat. No. 10,799,186.

(60) Provisional application No. 62/294,485, filed on Feb. 12, 2016.

(51) Int. Cl.

| | |
|---|---|
| ***A61B 5/11*** | (2006.01) |
| ***A61B 5/16*** | (2006.01) |
| ***A61B 5/372*** | (2021.01) |
| ***G16H 20/70*** | (2018.01) |
| ***G16H 70/60*** | (2018.01) |

(56) References Cited

U.S. PATENT DOCUMENTS

| | | | | |
|---|---|---|---|---|
| 6,338,628 | B1 | 1/2002 | Smith | |
| 6,468,210 | B2 | 10/2002 | Iliff | |
| 7,648,498 | B2 | 1/2010 | Hempel | |
| 7,756,575 | B2 | 7/2010 | Park | |
| 8,380,902 | B2 | 2/2013 | Howard | |
| 8,838,565 | B2 | 9/2014 | Bradshaw et al. | |
| 9,399,144 | B2 | 7/2016 | Howard | |
| 9,613,188 | B2 | 4/2017 | Bradshaw et al. | |
| 10,463,271 | B2 | 11/2019 | Intrator | |
| 10,799,186 | B2 | 10/2020 | Howard | |
| 11,006,848 | B2 * | 5/2021 | Agarwal | A61B 5/165 |
| 12,458,299 | B2 * | 11/2025 | Howard | A61B 5/4803 |
| 2002/0072686 | A1 | 6/2002 | Hoey et al. | |
| 2003/0040080 | A1 | 2/2003 | Miesenbock et al. | |
| 2003/0195584 | A1 | 10/2003 | Dawson | |
| 2004/0019370 | A1 | 1/2004 | Gliner et al. | |
| 2004/0186719 | A1 | 9/2004 | Polanyi et al. | |
| 2005/0118558 | A1 | 6/2005 | Wallis et al. | |
| 2005/0142524 | A1 | 6/2005 | Simon et al. | |
| 2005/0250082 | A1 | 11/2005 | Baldwin et al. | |
| 2006/0004279 | A1 | 1/2006 | Ikeda et al. | |
| 2006/0095251 | A1 | 5/2006 | Shaw | |
| 2007/0050151 | A1 * | 3/2007 | Satoh | G16H 20/70 702/19 |
| 2007/0117073 | A1 | 5/2007 | Walker et al. | |
| 2007/0225674 | A1 | 9/2007 | Molnar et al. | |
| 2009/0024050 | A1 * | 1/2009 | Jung | A61B 5/4064 600/544 |
| 2009/0157389 | A1 | 6/2009 | Shaw | |
| 2011/0015538 | A1 | 1/2011 | Matthews, Jr. | |
| 2011/0027765 | A1 | 2/2011 | Nader | |
| 2011/0060377 | A1 | 3/2011 | Howard | |
| 2011/0263946 | A1 * | 10/2011 | el Kaliouby | A61B 5/16 600/300 |
| 2012/0064493 | A1 | 3/2012 | Howard et al. | |
| 2012/0219934 | A1 | 8/2012 | Nakane et al. | |
| 2013/0338526 | A1 | 12/2013 | Howard | |
| 2015/0118661 | A1 * | 4/2015 | Haruta | G16H 50/20 434/156 |
| 2016/0029946 | A1 | 2/2016 | Simon et al. | |
| 2017/0164895 | A1 | 6/2017 | Howard | |
| 2017/0258389 | A1 | 9/2017 | Howard | |
| 2017/0258390 | A1 | 9/2017 | Howard | |
| 2017/0367607 | A1 * | 12/2017 | Agarwal | A61B 5/165 |
| 2018/0093092 | A1 | 4/2018 | Howard | |
| 2018/0260486 | A1 | 9/2018 | Howard et al. | |
| 2021/0106288 | A1 | 4/2021 | Howard | |

* cited by examiner

Fig. 4

"I [+] can't [-] really [-] think [+] right [+] now [-]. I [+] need [-] to [-] post [+] why [-] I [+] am [-] here [-]. I [+] can't [-] figure [+] out [-] how [-] to [-] do [+] it [-]. So [+], please [-] be [-] patient [-] with [+] me [-]."→+11 −17 = -6 (MSI)

"I [+] realized [-] that [-] I'm [+] not [-] viewed [-] in [+] a [-] positive [+] way [-] at [+] my [+] husband's [+] coworkers [-]. I'm [+] ugly [-]. I [+] don't [-] look [-] like [-] a [-] woman [+]. I [+] look [-] like [-] a [-] man [-] to [-] them [-]. I [+] must [-] look [-] like [-] a [-] monster [-]. I [+] know [+] that [-] I'm [+] ugly [-]."→+15 -25 = -10 (MSI)

"I'm [+] embarrassed [-]. I [+] was [-] actually [-] happy [+] yesterday [-]. I [+] was [-] proud [+] of [-] myself [+] for [-] actually [-] caring [+] about [-] how [-] I [+] presented [-] myself [+] to [-] the [+] world [+]. Now [-] I [+] know [+]. I'm [+] a [-] fool [-]. I [+] bring [+] shame [-] to [-] my [+] husband [+] because [-] I'm [+] the [+] butt [-] of [-] the [+] office [+] "ugly [-] wife [-] jokes [-]." The [+] anxiety [-] is [+] making [+] me [-] so [+] sick [-]. I [+] can't [-] stop [-] shaking [-]. I [+] can't [-] stop [-] crying [-]."→+28 -32 = -4 (MSI)

"I'm [+] so [+] down [-] and [+] depressed [-] about [-] what [-] they [-] said [-] about [-] me [-]. I [+] can't [-] get [-] it [-] out [-] of [-] my [+] head [+]. I [+] feel [+] so [+] stupid [- ]. I [+] feel [+] so [-] sick [-]. I [+] wish [-] I [+] could [-] just [-] walk [-] around [-] with [+] a [-] paper [+] bag [+] to [-] cover [-] my [+] head [+]. I [+] wish [-] I [+] could [-] just [-] become [-] invisible [-]."→+20 -29 = -9 (MSI)

DETECTION OF DISEASE CONDITIONS AND COMORBIDITIES

CROSS-REFERENCE TO RELATED APPLICATIONS

This application is a continuation at U.S. patent application Ser. No. 17/066,828, filed Oct. 9, 2020, which is a continuation of U.S. Pat. No. 10,799,186, filed Feb. 13, 2017, which claims the benefit of U.S. Provisional Application No. 62/294,485, filed Feb. 12, 2016, the contents of all of which are incorporated herein in their entirety.

BACKGROUND

The present invention relates to techniques for detection of disease conditions and comorbidities, such as those related to posttraumatic stress disorder using brain language and brain code.

Posttraumatic stress disorder (PTSD) is a highly heterogeneous condition, ranging from individual traumatic incidents such as car accidents to national tragedies such Posttraumatic stress disorder (PTSD) is a highly heterogeneous condition, ranging from individual traumatic incidents such as car accidents to national tragedies such as natural disasters. Every individual has a different depending on their personality and past experiences, especially regarding their tendency to depression. Hence the condition is better termed psychotrauma spectrum disorder (PSD). Its heterogeneity hinders reliable diagnosis, as detection is entirely dependent upon a clinician's subjective impression and sensitivity to comorbidities and there is always the possibility of concealment. Yet early diagnosis is essential, as the earlier PSD is detected the more likely treatment will be successful. Furthermore, reliable biomarkers of PSD would allow for much more accurate detection and monitoring of progression. Here we propose a new computational approach building on our prior work on the early detection of Parkinson's, Alzheimer's, and depression. We will use a new analysis tool, called the Brain Code (BC). This concept was developed to integrate many different kinds of data, for e.g., the often fragmented and incomplete outputs from body sensors that record balance, dexterity, postural, facial, and vocal movements combined together with cognitive or clinical outputs such as the intentional or emotive content of speech. The Brain Code allows us to fit all these different data streams together in such a way as to compensate for the deficiencies of each individually. It can put disparate physiological and cognitive data into the same 'coordinate system', so that we will be able to develop a reliable quantitative 'signature' of PSD. These quantitative biomarkers will be designed so that they are useful for both physicians in a clinical setting and for communities affected by a large-scale traumatic event.

Accordingly a need arises for improved detection of detection of disease conditions and comorbidities, such as PTSD, Parkinson's, Alzheimer's, depression, etc.

SUMMARY

In an embodiment, anew computational approach may provide improved detection of disease conditions and comorbidities, such as PTSD, Parkinson's, Alzheimer's, depression, etc. We will use a new analysis tool, called the Brain Code (BC). This concept was developed to integrate many different kinds of data, for e.g., the often fragmented and incomplete outputs from body sensors that record balance, dexterity, postural, facial, and vocal movements combined together with cognitive or clinical outputs such as the intentional or emotive content of speech. The Brain Code allows us to fit all these different data streams together in such a way as to compensate for the deficiencies of each individually. It can put disparate physiological and cognitive data into the same 'coordinate system', so that we will be able to develop a reliable quantitative 'signature' of PSD. These quantitative biomarkers will be designed so that they are useful for both physicians in a clinical setting and for communities affected by a large-scale traumatic event.

For example, in an embodiment, a computer-implemented method for detecting a disease condition may comprise receiving a plurality of data streams, each data stream representing a measurement of a brain activity comprising physical and chemical phenomena and performing pattern analysis on the plurality of data streams to detect at least one fundamental code unit of a brain code corresponding to a disease condition based on a combination of the plurality of data streams.

In an embodiment, the physical and chemical phenomena may comprise at least one of electroencephalographic monitoring, linguistic assessment, behavioral tracking, facial feature analysis, mood state, cognitive state, language analysis, speech, and vocal impairments, modes of speaking, and body movement. The pattern analysis may comprise at least one of language analysis using machine learning, syntactic structure identification, multilayered perceptron neural networks, machine translation processes, case-based reasoning, analogy-based reasoning, speech-based cognitive assessment, mind default axiology, mood state indicator, linguistic-axiological input/output, and mind default axiology.

For example, in an embodiment, a computer program product for detecting a disease condition may comprise a non-transitory computer readable storage having program instructions embodied therewith, the program instructions executable by a computer, to cause the computer to perform a method comprising receiving a plurality of data streams, each data stream representing a measurement of a brain activity comprising physical and chemical phenomena and performing pattern analysis on the plurality of data streams to detect at least one fundamental code unit of a brain code corresponding to a disease condition based on a combination of the plurality of data streams.

For example, in an embodiment, a system for detecting a disease condition may comprise a processor, memory accessible by the processor, and computer program instructions stored in the memory and executable by the processor to perform receiving a plurality of data streams, each data stream representing a measurement of a brain activity comprising physical and chemical phenomena performing pattern analysis on the plurality of data streams to detect at least one fundamental code unit of a brain code corresponding to a disease condition based on a combination of the plurality of data streams.

BRIEF DESCRIPTION OF THE DRAWINGS

Posttraumatic stress disorder (PTSD) is a highly heterogeneous condition, ranging from individual traumatic incidents such as car accidents to national tragedies such

FIG. 4 illustrates several examples of application of the MSI to authentic expressions.

FIGS. 14 and 14CONT show a diagram of a Brain Code algorithm for cognitive processing under task loaded conditions.

FIGS. 15 and 15CONT show a diagram of a Brain Code algorithm for cognitive processing under task loaded conditions.

DETAILED DESCRIPTION

Figure 1:
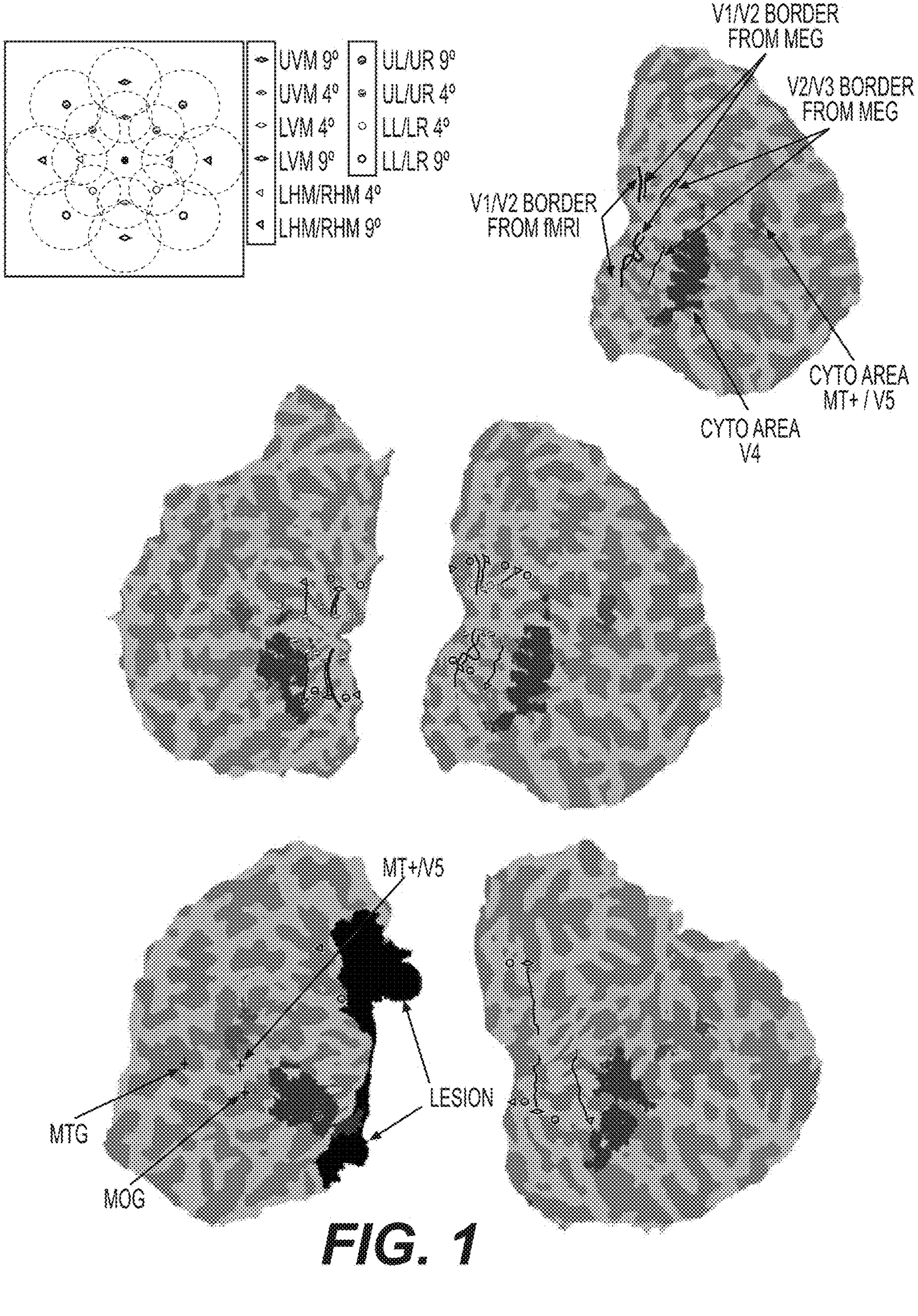
FIG. 1 illustrates an example of a flattened occipital cortex.

Posttraumatic stress disorder (PTSD) is a highly heterogeneous condition, ranging from individual traumatic incidents such as car accidents to national tragedies such

ACRONYMS

ACC—Anterior Cingulate Cortex
ACT—Adaptive Control of Thought
AD—Alzheimers Disease
ADL—Activities of Daily Living
AFR—Audio Affect Recognition
AHTD—At Home Telemonitoring Device
AI—Artificial Intelligence
ALS—Amyotrophic Lateral Sclerosis
ANN—Artificial Neutral Networks
ANOVA—Analysis of Variance Software
ASD—Autism Spectrum Disorder
BC—Brain Code
BDI—Beck Depression Inventory
BP—Bipolar Disorder
BSN—Body Sensor Network
CNS—Central Nervous System
COM—Centre of Mass
COMT—Catechol O-Methyl Transferase Inhibitors
CSF—Cerebrospinal fluid
CSP—Common Spatial Pattern
CT—Computer Tomography
CWT—Continuous Wavelet Transform
DA—Dopaminergic
DAT—Dopaminergic Transporter
DBS—Deep Brain Simulation
DCR—Digital Camera Ready
DNA—DeoxyriboNucleic Acid
DRAM—Dynamic Random Access Memory
DSM—Diagnostic and Statistical Manual
DT/AT—Deceleration time/acceleration time
DTI—Diffusor Tensor Imaging
ECMS—Ego-Centered Mind State
EEG—Electroencephalogram
EFNS—European Federation of the Neurological Societies
EMBS—Engineering in Medicine and Biology Society
EMG—Electromyography
EMNLP—Empirical Methods in Natural Language Processing
ER—Emotion Recognition
ET—Essential Tremor
FCP—Facial Characteristic Points
FCU—Fundamental Code Unit
FFT—Fast Fourier Transforms
FLMP—Fuzzy Logical Model of Perception
fm—Median Frequency
fMRI—Functional Magnetic Resonance Imaging
FOG—Freezing of Gait
GLM—Generalized Linear Models
GMM—Gaussian Mixture Model
GPi—Globus Pallidus H&Y-Hoehn and Yahr
HMM—Hidden Markov Model
HPC—Hippocampal
HNR—Harmonic-to-noise ratio
Hz—Hertz
IARPA—Intelligence Advance Research Projects Activity
ICAD—International conference on Alzheimer Disease
ICC—Intraclass Correlation Coefficient
ICSS—Integrated Clothing Sensing System
IEEE—Institute of Electrical and Electronics Engineers
IMU—Internal Measurement Unit
IND—Indeterminate
IQ—Intelligence Quotient
IWSF—International Waterski & Wakeboard Federation
kNN—K-Nearest Neighbors
L-DOPA—Levodopa
LDA—Latent Discriminative Analysis
LFP—Local Field Potential
LFPC—Log Frequency Power Coefficients
LM—Levenberg-Marquardt LM—Long-term Memory
LTD—Long-term Depression
LTP—Long-term Potentiation
LXIO—Language/Axiology Input and Output
MAL—Motor Activity Log
MAO-B—Monoamine oxidase B Inhibitors
mBSN—Multimodal Body Sensor Network
MDA—Mind Default Axiology
MDP—Markov Decision Process
ME—Measurement Error
MEG—Magnetoencephalography
MFCC—Mel Frequency Cepstral Coefficient
mg—Milligrams
MIT—Massachusetts Institute of Technology
MRI—Magnetic resonance imaging
MSI—Mind State Indicator
NDD—Neurological Disorder
NHR—Noise-to-harmonic ratio
NLP—Natural Language Processing
OAR—Object-Attribute Location
PAG—Periaqueductal Gray
PCC—Pearson Correlation Coefficient
PET—Positron Emission Tomography
PPE—Measure of Fundamental Frequency Variation
PSD—psychotrauma spectrum disorders
PSEN-1—Presenilin-1
PSEN-2—Presenilin-2
PTSD—Posttraumatic Stress Disorder
RAM—Random Access Memory
REM—Rapid Eye Movement
RMSE—Root Mean Square Error operating characteristics curve
ROM—range of motion
SNR—Signal to Noise Ratio
SNRI—Serotonin and Norepinephrine Reuptake Inhibitors
SPSS—Statistical Package for the Social Sciences Software
STN—Subthalamic Nucleus
SUVR—Standard Uptake Value Ratio
SVM—Support Vector Machine
TBI—Traumatic Brain Injury
TD—Tremor Dominant

Section One: Introduction

Post Traumatic Stress Disorder (PTSD) is a collection of heterogeneous responses to trauma, which can be acute and chronic, where trauma is understood as an extreme, life-threatening event (Blake et al., 1995; Brewin et al., 2009; Briere et al., 2005; Feldner et al., 2007). According to the DSM 5 PTSD is characterized by the following series of symptoms: re-experiencing of the event (nightmares)/avoidance of stimuli associated with the trauma/negative alterations in thoughts and mood including numbed responsiveness (detachment, anhedonia)/increased arousal (hypervigilance, exaggerated startle) which leads to significant distress or impairment in functioning (Abubakr et al., 2003; Ait-Aoudia et al., 2013; Galatzer-Levy and Bryant, 2013; Gilboa, 2013; Jovanovic et al., 2010; Mittal et al., 2001; Rushby et al., 2013b; Walters and Hening, 1992; Yehuda, 2001; Yehuda, 2002). Epidemiologic evidence suggests that most individuals with PTSD are diagnosed with at least one other mental illness, and a substantial number have 3 or more comorbidities in addition to PTSD. Studies suggest that approximately 80% of patients with PTSD have at least one comorbid psychiatric disorder, such as bipolar disorder and major depression (Su et al., 2009). Furthermore PTSD is commonly masked by mood and anxiety disorders, as well as chronic pain and addictive behavior, which may appear as a result of the trauma or be pre-existing, but in either case are substantially aggravated (Lew et al., 2009; Sharp and Harvey, 2001; Spinhoven et al., 2014).

One marked problem in PTSD's epidemiology is that, until recently, nomenclature mis-categorized the disorder under an existing psychiatric category (anxiety disorders) instead of giving it a separate classification (Kinzie and Goetz, 1996). The most recent DSM 5 reclassified PTSD (as well as Acute Stress Disorder) from the class of "anxiety" disorders into a new class of "trauma and stressor-related disorders" (Brewin et al., 2009; Rosen et al., 2008; Santiago et al., 2013; Spitzer et al., 2007). The rationale for the creation of this new (and very necessary) class is based on widespread clinical acknowledgement of the heterogeneous expressions of distress in response to trauma (Bonanno and Mancini, 2012; Breslau, 2012; DiMauro et al., 2014). Nearly every individual develops a unique series of responses to trauma, spanning a spectrum of normal to abnormal distress and dysfunctional symptoms. In light of this new classification and growing opinions that PTSD should be regarded as a spectrum (Bremner, 2002, Greenberg et al., 2014; Moreau and Zisook, 2002), I advocate for using the term "Psychotrauma Spectrum Disorders" (PSD) to encompass all the commonly comorbid conditions.

Psychotrauma Spectrum Disorders

Post trauma syndromes are the result of an external event such as violent assault or natural disaster, which causes a much higher adrenaline response than the body is prepared for. This initial response is temporary, but creates deep neurological imprints that can affect future cognitive pathways in ways that are still poorly understood. The persistence of these patterns and imprints when a patient is reminded of or exposed to traumatic experiences creates a "hyperarousal" state, which is marked by sudden mood swings, over-vigilance, and high sensitivity to sensory stimuli. During the initial triggering traumatic experience, adrenaline and other stress hormones tend to suppress hypothalamic activity, creating a cognitive template that is often repeated under less stressful situations. When symptoms persist longer than 3 months it is designated as chronic PTSD (Abosch et al., 2012; Bryant et al., 2013; Harvey and Bryant, 1998; Harvey and Bryant, 1999; Lyttle et al., 2010; Mercer et al., 2012; Sharp and Harvey, 2001; Wade et al., 2014; Zlotnick et al., 1999).

It is estimated that 25% of cases present delayed onset, meaning the symptoms are not present for a period of time (often years) after the event of trauma (Gold et al., 2000; Qureshi and Mehler, 2013), whereas some cases are chronic with persistent symptoms for several years after initial exposure to trauma (Andrews et al., 2007; Cukor et al., 2011; Gold et al., 2000; Horesh et al., 2013; Huggins et al., 2011; Zlotnick et al., 2001). However, only a small subset of acute trauma symptoms are reliable predictors of the development of chronic PTSD (Harvey and Bryant, 1998; Harvey and Bryant, 1999). Current clinical standards for diagnosing PTSD are subjective self-reporting and face-to-face evaluation by mental health professionals[2]. PTSD is often accompanied by other psychiatric disorders (Brady, 1997; Kessler et al., 2005; Panagioti et al., 2012; Spinhoven et al., 2014; Yehuda et al., 2004; Zlotnick et al., 2003). Most individuals with PTSD are diagnosed with at least one comorbid disorder and a substantial number have 3 or more in addition to PTSD. PTSD is often masked by mood and anxiety disorders, as well as chronic pain and addictive behavior, which may appear with the trauma or pre-exist, but are substantially aggravated and further complicate diagnosis and treatment (Lew et al., 2009; Sharp and Harvey, 2001; Spinhoven et al., 2014). Somatic comorbidities, such as endocrine, obesity, and musculoskeletal disorders) are commonly experienced as well.

We know that traumatic events leading to PTSD tend to "deregulate" brain networks underlying emotion, integration of sensory input and motor output and physiological arousal, as well as the capacity to engage properly in the present (Brousse et al., 2011; Delahanty, 2011; Dethier et al., 2013; Huggins et al., 2011; Jovanovic et al., 2010; Koso and Hansen, 2006; Rushby et al., 2013a). Biologically, the fear conditioning and "neural sensitization" in the weeks following an incident of trauma may lead to increased activation of the sympathetic nervous system and possibly the development of PTSD (Briere et al., 2005; Bryant, 2003). On the cognitive level, the development, and continuation, of acute or chronic PTSD symptoms is largely shaped by the cognitive responses following the traumatic event, such as peritraumatic dissociation (Briere et al., 2005; Bryant et al., 2000; Bryant et al., 2013), which has been recognized in several meta-analysis studies as a reliable predictor of the onset of PTSD (Bui et al., 2010a; Bui et al., 2010b; Trickey et al., 2012).

Comorbidity

Comorbidity, or the presence of multiple physiological or psychological disorders, is a significant obstacle to PSD detection, diagnosis, and management. For instance, the DSM V definition for major depressive disorder shares a number of symptoms with PTSD, even though it is not always triggered by stressful or traumatic events. The International Society for Traumatic Stress Studies (ISTSS) guidelines for PTSD treatment estimate that "approximately 80% of people with posttraumatic stress disorder (PTSD) have a co-occurring psychiatric disorder (lifetime rates), yet treatments to address such comorbid conditions have only recently been developed and studied." The ISTSS guidelines also identify several common comorbid conditions, which include substance abuse, OCD, borderline personality disorder, and psychotic disorders. It is often difficult to distinguish conditions as a result of trauma from these comorbid disorders, which could be pre-existing. In addition many pharmacological therapies often prescribed to psychiatric patients yield side effects that can be confused with symptomologies of comorbid disorders. According to Valderas et al. (2009), "comorbidity is associated with worse health outcomes, more complex clinical management, and increased health care costs." This is partly due to the fact that the phenomenon of comorbidity itself is poorly understood. We may be able to recognize signs of multiple disorders at once, but how they interact with one another, and with the patient's psyche, is a problem too complex for current clinical constructs. Angold et al. (1999) Suggest that the causes of disease comorbidity are due to four factors: direct causation, associated risk factors, heterogeneity, and independence.

(Brady et al., 2000) Investigate comorbid depressive disorders of PTSD and conclude that these and substance abuse disorders tend to manifest with similar symptoms to PTSD. In the National Comorbidity Study (NCS), the odds ratio for substance use disorders to PTSD was 2-3 for men and 2.5-4.5 for women. Brady et al.'s study also found that "having a previous depressive disorder is a risk factor for the development of PTSD once exposure to a trauma occurs" (Kessler et al., 1995). Because the personality and behavioral symptoms that are indicative of major depression and PTSD are so similar, a more precise method of differential diagnosis is needed.

Many obstacles to the comorbidity problem continue to persist. Among them is a series of methodological shortcomings in the clinical field that do not differentiate between truly comorbid conditions and multi-morbid conditions. PTSD is unique in that the disorder itself and many of its comorbid conditions are likely to share a common cause, but there still exists the possibility of predisposition to PTSD. Separating predisposition from comorbidity, while largely beyond the capabilities of current diagnostic methods, promises to deliver superior guidance to clinicians who design treatment regimes if it can be achieved on a consistent and timely basis.

PTSD Resilience

Social resilience is defined as "the capacity to foster, engage in, and sustain positive relationships and to endure and recover from life stressors and social isolation (Cacioppo et al., 2011). Other definitions include "sustainability of purpose in the face of stress" and "recovery from adversity" (Zautra et al., 2008). Moreover, social resilience is described as a process of "linking a set of adaptive capacities to a positive trajectory of functioning and adaptation after a disturbance" (Norris et al., 2008). In contrast with "stability," a term used to denote the ability to resist change, "resilience" as a term that emerged from the systemic ecological context concerns the system's ability to flexibly renew its resources by returning to its original attractor after a turbulence has violently distracted its course (Neuman, 2008). It is a process known as "relaxation" according to Scheffer (2009) in which the system stabilizes again after encountering a critical tipping point. In sum, monitoring social resilience is monitoring the population's ability to manage a stressful disturbance and to return to "stability" despite a traumatic experience. One should remember that although "resilience is a widely-used concept, studies vary substantially in their definition, and measurement." Above all, there is no common underlying theoretical construct to this very heterogeneous research, which makes comparing findings extremely difficult (Davydov et al., 2010).

There are several factors influencing resilience, which include emotional self-awareness and emotional expression (Armstrong, 2011) social support (Prati and Pietrantoni, 2010) and feeling of connectedness to others (Cacioppo et al., 2011). Nevertheless, the operational definition of resilience is context dependent, as the resilience expected from an Olympic athlete does not necessarily overlap with the resilience expected from a community facing a natural disaster. Therefore, the operational definition of resilience should be context dependent.

Agaibi and Wilson (2005) examine PTSD resilience from the standpoint of five explanatory variables: personality traits, affect regulation, coping mechanisms, ego defenses, and the use of protective factors such as therapy after traumatic events. In particular, he defines resilience as the ability to recover from a state of PTSD diagnosis to an optimal state of psychological function, and the time it takes to do so. Resiliency is often manifested as competence. That is, the manner in which a patient addresses and responds directly to a traumatic event can have a significant impact on the later progression of PTSD symptoms. Survivor's guilt, for instance, is a common PTSD trigger syndrome that originates in the patient's self-doubt and lack of experience in addressing traumatic stress. Patients with a more developed understanding of such stressors tend to suffer less from this syndrome, and thus are less susceptible to PTSD symptoms. In addition, Agaibi et al. identify self-efficacy during stress as a vital component of PTSD resilience. The sensation of helplessness, in which a patient was not able to improve their own situation during periods of traumatic stress, is another contributor to PTSD. Weisath (1995) develops this concept of competence further: “competent performance indicates positive beliefs about self, task performance, and problem solving.” Both he and Agaibi et al. appear to agree that pre-exposure training is one of the more effective ways to build PTSD resilience. However, this still leaves the problem of untrained patients exposed to PTSD stressors.

Pre-existing conditions, apart from stress preparedness, can affect the patient’s psychological outcome. In particular, Garmezy (1991) cites a combination of factors, such as maternal social, biological, and environmental disadvantages, that can contribute to PTSD susceptibility. These factors often affect the childhood development of patients, and are shown to affect their psychological resilience. This is in part because, at the childhood level, patients have little control over their circumstances and little experience in responding to stress. Thus, they are more likely to feel helpless during periods of stress, and their general lack of self-efficacy further contributes to their susceptibility to post-traumatic stress.

Fellsman et al (1982) also addresses the issue of childhood susceptibility to PTSD, citing IQ and boyhood competence, or “a measure of active involvement in activities and a good childhood environment” as good indicators of resilience in young males. However, owing to the significant variability in psychosocial development across more resilient members of the Fellsman’s study, it is difficult for the authors draw a direct causal relationship between life-span development patterns and long-term resilience. While early development factors are clearly significant in the development of an individual’s psychological resilience (and thus resilience to PTSD symptoms), other intervening factors such as lifestyle choices, preparation, and the nature of the stressor can also have a significant effect on patient outcomes.

There is a growing recognition that resilience should be multilevel and take into account both the individual and group level of analysis. Social media blurs the difference between the individual and collective levels of analysis and provides an interesting platform for the study of social resilience.

Large Scale Psychotrauma

A central problem in the field of post trauma stress is the ability to detect PTSD or risk of PTSD in the aftermath of traumatic events. Exposure to a traumatic event is relatively common; it is estimated that in any given year up to one fifth of people in the united states will experience a traumatic event and up to two thirds of people may experience a traumatic event at some point during their lifetime (Breslau et al., 1991; Norris, 1992). Unlike physical injuries, psychotrauma conditions and symptoms are not always apparent especially at first, and can go unrecognized long periods of time. It is critical that emergency response methods are timely and efficient especially considering the amount of people that can be affected by disaster both directly and indirectly. Survivors are not the only ones effected by large-scale events of trauma, but can also include anyone who witnessed a trauma or had a loved one who was exposed to trauma. Assessing as many people as possible in a short amount of time is a central priority of disaster response, but also follow-ups and continued evaluation is also needed, because psychopathology can develop and worsen over time sometimes hibernating for years. Resilience and vulnerability factors for each victim adds another layer of complexity to rapid mental health screening.

The most widely used mental health response methods are brief screening tools such as interviews or checklists administered to individuals at least once following a traumatic event (North and Pfefferbaum, 2013). Screening tools such as the Primary Care PTSD Screen (PCPS), the Short Screening Scale for PTSD (SSSP), the Screening tool for Early Prediction of PTSD (STEPP), Impact of Event Scale, the Diagnostic Interview Schedule, the PTSD checklist, the National Women’s Study PTSD module and the abbreviated PTSD checklist, can be used during post-disaster response. Often a layperson as a member of a response team administers these screening tools (Galea et al., 2005). The Clinician Administered PTSD Scale and the Structured Clinical Interview for DSM-III-R, are less common because they require an interview conducted by a Clinician (Galea et al., 2005).

Ideally what is needed in the aftermath of a disaster or traumatic event is a rapid screening tool that can be administered anywhere and does not require a trained clinician. Trauma screening would also benefit from a method that takes additional psychological and physiological variables into consideration. For instance The New York PTSD Risk Score screening instrument developed by Boscarino et al. (2011) is a brief PTSD screener that integrates clinical, psychosocial, and demographic factors on top of the Primary Care PTSD Screen. The New York PTSD Risk Score includes 5 prediction domains: stressor exposure, sleep disturbances, suicidal thoughts, depression symptoms, and demographic factors. When tested on a World trade center cohort and a group of pain patients at a trauma center, the prediction tool demonstrated higher specificity and sensitivity when compared to the Primary Care PTSD screen alone.

An objective screening tool that does not require a person to administer or any self-reporting would further eliminate subjectivity. Additionally an objective-screening tool that can be administered on a routine basis starting right after experiencing a traumatic event would provide rich data to model and predict personalized PSD trajectories.

Foundations of a New Approach

The overarching aim is to develop a comprehensive, biomedical, nonintrusive, mobile ‘sensor’ system to characterize post-traumatic trajectories based on non-invasive measures of pathophysiological, behavioral, cognitive, and emotional and other neurobiological outcomes. These outcomes may serve as objective biomarkers, which should aid the scientific community in better understanding the course and trajectory of posttraumatic syndromes and work towards developing promising targets for intervention. To capture the full spectrum of post trauma syndromes requires a large amount of serial longitudinal data from a large population of patients, and several dimensions of measurable outcomes over time. Ideally data from several “brain networks” needs to be measured quantitatively and analyzed to link together cognitive and behavioral indicators of PTSD.

Behavioral Biomarkers

Behavioral biomarkers are a broad category of measures that clinicians can use to detect and diagnose disorders. ‘Behavior’ is defined as the external responses (actions or inactions) to internal and/or external stimuli, excluding responses understood as developmental changes (Bell et al., 2009; Bosl et al., 2011; Gomar et al., 2011; Jovanovic et al., 2010; Lee and Jung, 2013; Levitis et al., 2009; McGhee et al., 2013; Mittal et al., 2001; Schmidt et al., 2013; Torres et al., 2013; Yener and Basar, 2013; Zhang et al., 2009), whereby behavior is mainly understood as product of the motor system (movement) as well as cognition (speech and language). Therefore, these two systems, which are products of neural electrical activity, form an important set of modalities of interest in terms of behavioral biomarkers of post trauma. The recent study of Torres et al. (2013) demonstrates the effectiveness of measuring intelligent action data streams to detect clinical biomarkers. Torres et al. (2013) assessed behavioral movement (micro-movement) inventories to diagnose autism spectrum disorders. Their work acknowledges that behavior requires movement. Inclusion of this data seems likely to provide an objective characterization of behavior giving insight into interactions between the peripheral and the central nervous systems. The nature of this kind of data is heterogeneous, dynamic, and stochastic. Torres et al. offer a unifying statistical framework to reveal re-afferent kinesthetic features of Autism. Their method detects stochastic patterns of minute fluctuations (micro-movements) inherent in natural movement. Such patterns of behavioral variability provide re-entrant sensory feedback contributing to the autonomous regulation and coordination of motor output. From an early age, this feedback supports centrally driven volitional control and fluid, flexible transitions between intentional and spontaneous behaviors. Torres et al. explain that in Autism, there is a disruption in the development of proprioception and corollary discharge of the motor program. Despite this disturbance, each individual has unique adaptive compensatory capabilities that are used to evoke faster and more accurate decisions. The findings of Torres, et al. support our proposed project to measure output of the motor system and various stimuli to observe kinesthetic perception in response to trauma syndromes.

These biomarkers are the key to the establishing an effective diagnostic method for neurological disorders including PTSD. Biomarkers are a gateway into the cognitive state of individuals with disorders. As Howard et al. (2013) mention, the study of neural oscillations within the cerebral cortex can provide a significant amount of information about brain function and dysfunction. The platform they have developed, the ‘Fundamental Code Unit’ (FCU) provides the ability to integrate and quantify disparate biomarkers within the same ‘coordinate system’. By utilizing this FCU, early detection of dysfunctional neural oscillations can lead to earlier diagnosis of brain disorders. The goal of the Fundamental Code Unit is to provide a foundation for the Brain Code (BC)[6], which, simply put, is essentially a higher-level analysis that utilizes data processing methods that are assembled from widely different neurological, chemical and psychological components. The combination of each produces a cognitive output of which natural language, for example, is one product to create this holistic output.

Human Behavior

Behavior can be described as our internal responses to stimuli, both internal and external. (Levitis et al., 2009). With that in mind it is important to take into account a system’s synergy. The interaction of multiple elements in a complex biological system requires the measurement of a minimum subset of the elements. The selection of elements to describe behavioral biomarkers comes from our understanding of behavior, which we perceive as interpretation of movement and posture (motor system) as well as speech and language. In addition, these elements of behavior are the product of neural electrical activity.

Perception & Judgement

In order to properly identify where machines can interface with the brain, and the capabilities that this will yield, we must first develop an understanding of the functions and rough structure of human cognition, because it defines our collective understanding of the phenomena.

Barsalou’s (2008) model of cognition is made up of four distinct components based on function, physiology, and location within the brain (Barsalou, 2008). The first component consists of sensation and perception. This connects the five observatory senses to the overall mechanism of cognition via sensory “buffers” that render the input from these senses more easily understood. The second family of brain functions is that of long-term memory, habits, skills, and other memory engrams that may be retrieved long after they were created. These include perceptual memory, memory of one’s own life and experiences, linguistic and semantic skills, visual memories, and habits and motor skills. Short-term memory consists primarily of executive functions, as well as pre-executive rehearsal of speech and motor movement. The motor control/action component of cognition is responsible for action planning and response. Of the four components of cognitive function, perception has traditionally been central to diagnosis of neurological disorders because it reflects the patient’s own experience and therefore informs patients’ self-reports. Perception is defined as the process of becoming aware of some object or activity in one’s surrounding environment through the five senses, because this process can separate one’s view of reality. The brain binds inputs from multiple senses to enhance our ability to identify key events in the environment. This process is often based on information from several senses.

From a philosophical perspective, Spinoza breaks perception into four constituent parts: perception by the senses, by experience, by deductive reasoning, and by intuition. Each of these components is influenced by its own complex set of stimuli, and each individual may process these stimuli differently. Perception is therefore a highly subjective and idiosyncratic process, which rarely produces a perfect reflection of actual events. Differences in perception and disparities between perception and reality have significant potential to cause misunderstanding and conflict. In a clinical context, such misunderstandings can affect a practitioner’s ability to identify etiology and predict outcomes, with implications for the effective and timely diagnosis of neurological disorders.

One study in particular, whose focus was predictive analysis of consumer behavior in response to changes in advertising content, found that “affect dominates over cognition for predicting conative attitude and action” (Morris et al., 2002). In essence, the development of perception is affected by pre-existing emotional neural pathways as much as it forms new pathways. For that reason, the authors found that affect, or an enduring and often pre-existing component of intention whose origin is often rooted in the emotional determinants of behavior and perception, is not mediated by cognition. Since active cognitive processes do not influence affect as strongly as previously thought, and affect actively influences behavior, Morris et al.’s research suggests that perception results from a complex, multi-origin combination of pre-existing neural patterns and new combinations of neural activity.

The first component consists of sensation and perception. This connects the five observatory senses to the overall mechanism of cognition via sensory “buffers” that render the input from these senses more easily understood. The brain binds inputs from multiple senses to enhance our ability to identify key events in the environment often based on information from senses. One study in particular, whose focus was predictive analysis of consumer behavior in response to changes in advertising content, found that "affect dominates over cognition for predicting conative attitude and action." In essence, the development of perception is affected by pre-existing emotional neural pathways as much as it forms new pathways. Since active cognitive processes do not influence affect as strongly as previously thought, and affect actively influences behavior, Morris et al.'s research suggests that perception results from a complex, multi-origin combination of pre-existing neural patterns and new combinations of neural activity.

The second family of brain functions is that of long-term memory, habits, skills, and other memory engrams that are retrieved long after they are created. These include perceptual memory, memory of one's own life and experiences, linguistic and semantic skills, visual memories, and habits and motor skills. Short-term memory consists primarily of executive functions, as well as pre-executive rehearsal of speech and motor movement. The motor control/action component of cognition is responsible for action planning and response. Of the four components of cognitive function, perception has traditionally been central to diagnosis of neurological disorders because it reflects the patient's own experience and therefore informs patients' self-reports.

Intention Awareness

Multisensory processing and integration even allows for distinction of oneself from others, which is required for self-awareness and social interactions. The awareness of self and others is based on exteroceptive and interoceptive models and influences discussion making on many levels. The unreliable and flexible nature of perception introduces a note of randomness into the human system. This randomness, or noise, plays an important role in cognitive modeling and provides both a positive influence in terms of exploring possible solutions, as well as a negative by inducing errors in prediction, West et al. (2006). It is known that predictions become harder as randomness increases. Intelligent cognition arises from a correct interpretation of a situation despite the noise. This also holds for predicting intent in the case of interaction with another "intelligent" system. Situation and intention awareness are therefore similar components of intelligent cognition in that the first is necessary, but not sufficient, to achieve the latter. Systems that incorporate situational awareness or enhance that of human operators have found successful applications, especially in scenarios dealing with high volumes of data in real time, such as command and control communication technology. Howard and Cambria (2013) suggest that these intention-aware systems reduce informational strain on humans with the same high level of effectiveness compared to situation-aware systems. However, such applications may give the impression that situation awareness is complete when only a few parameters are known. These parameters are typically raw quantitative data that by themselves tell us little about situations especially when they are a product of humans. This is exactly the kind of data for which we can apply mining techniques and a-priori understanding to optimize outcomes. By integrating concepts of intention awareness, or taking into account the internal processes of actors/nodes themselves, it is possible to significantly improve this analysis. Because "intentions play an essential role in transforming unconscious processes into conscious processes and physical activities" (Howard, 2002; Howard, 2012b; Howard, 2013b; Howard and Cambria, 2013c) (Howard, 2002), developing a more effective application to enhance understanding of situation awareness could provide us significantly more insight on the complex human mind.

Situation awareness provides a snapshot of the environment; A situation-aware system does not account for changes over time or the originating causes of the actions it documents. For situation-specific information to confer intention awareness to the analyst, two events must occur. First, information of greater dimensionality must be gathered. This means compiling connection-level data (frequency, length, bandwidth, data transferred, etc.) and 'offline' data with implications for behavior (i.e., level of security of the system, as perceived by a potential attacker). Second, intention-based analysis must be applied to this gathered information. In particular, each action, or event, is connected to some actor based on the information available, and intent is extrapolated based on that actor's series of actions over time. There are two specific components of human cognition that intention awareness (IA) mimics. First, humans extrapolate, or "fill in the blanks," when there is not enough information to come to a conclusion. This includes cost-benefit analyses regarding each possible reality based on incomplete information, as well as balancing the probability and stakes of each decision. Second, we prioritize when there is a glut of information. When information is too plentiful for human cognition to account for all of it or there is too little time to analyze all of the information at hand, relevance, importance, and ease of analysis become metrics of prioritization. That is, in order to solve problems, we form criteria based on which information is most necessary to our goals, and we analyze accordingly. Extrapolation and prioritization are similar in that they are both adaptations to imperfect information environments. The former has always been a fundamental problem in supervisory control systems, whether they are political, military, or otherwise. However, the problem of information excess is relatively new and unique to the digital age in which the number of connections and data transmitted via those connections is consistently increasing.

When humans prioritize, they perform a sort of extrapolation, which has some level of uncertainty about which information is most vital. That measurement must be made on a per-case basis, and burdening humans with that task at the speeds at which cyber-security threats emerge is not feasible for the effective protection of information. The marriage of available modern computational technology to human methods of strategy in adverse conditions such as warfare is the next logical step in information protection. The tangible result of this application is an informational presentation consisting of intentions and actions that act upon one another. This provides both causal, or motivational, and temporal dimensionality that allows for more information-rich analysis (West et al., 2006; West et al., 2005). A large part of intention awareness is the capacity for inference. Since total intention awareness would require perfect situational and contextual information, systems to be deployed can only approach it. Nevertheless, the greater decisional automation it offers saves valuable man-hours for tasks that cannot be completed computationally using additional steps. This will illustrate how a subjective concept can be modeled and predicted.

As always, the quality of our prediction is governed by the mathematical model used and the available data, with its limitations. The same kind of reasoning can be applied when we want to understand perception and cognition on a more individual level.

Prior research focusing on the cognitive formulation of intention, which incorporates the aforementioned aspects, has shown that mathematical modeling can help us understand and predict the outcomes that result from complex interactions of actors and systems of actors. "Intention" is a cognitive construct that predicts actions, based on the assumption that actions are purposeful and thus guided by the desire for some specific outcome. We believe that the observable characteristics of physical situations provide sufficient information to form hypotheses about the guiding intentions. This model has already been successfully applied in several non-medical domains, but we plan to apply this human cognitive model to the evaluation and diagnosis of neurological disorders.

Intentionality is a useful template for consciousness because it incorporates temporality; that is, intentions cannot be formed without some notion of how events will transpire over time, and state changes over time can tell us a great deal about brain function or disorder. For this reason, it is useful to view the conscious brain as a 'hierarchical prediction machine'. One of the most important brain functions is to match "incoming sensory inputs with top-down expectations or predictions," a process that a greater understanding of intentions will allow us to understand and study in greater detail (Clark, 2012).

The Brain Code

The Brain Code is a comprehensive approach that compiles and collects a series of fragmented, often incomplete, streams of data and applies a method to fit them all together in a way that counteracts the weaknesses associated with each individual data stream. The BC aims to quantify the linkage between input and output, such as speech and movement parameters to isolate features, trends, and patterns that are specific enough to characterize phenotypical structure, suggesting specific markers. While the concept of a "Brain Code" may sound like an abstract framework, brain activity is essentially composed of physical and chemical phenomena whose interactivity is still not well understood, but can sometimes be measured or observed. By designing data units, data acquisition hardware, and novel cognitive data structures, we propose novel analysis to better understand this interactivity and its changes in response to trauma.

The design of the proposed study is based on BC success with Parkinson's Disease and Alzheimer's (Bergmann and Howard, 2012; Bergmann et al., 2013; Howard; Howard; Howard; Howard, 2014; Howard and Bergmann, 2012; Howard et al., 2013a; Howard et al., 2013f; Howard et al., 2014; Howard et al., 2013o; Howard and Stein, 2013; Howard et al., 2013v; Nave et al., 2013). Many studies suggest that PTSD and dementia share several proposed risk factors and neuroanatomical correlates (Qureshi et al., 2011; Schmand et al., 1997; Whalley et al., 2000). For example, it has been suggested that lower intelligence (Barrett et al., 1996; Brandes et al., 2002; Ehlers and Clark, 2000; Gale et al., 2008; Gil et al., 1990; Gilbertson et al., 2006; Kleim et al., 2012; Koenen et al., 2007; Kremen et al., 2007; McGurn et al., 2008; McGurn et al., 2004; Schmand et al., 1997; Whalley et al., 2000; Yehuda et al., 2006), lower educational level (Iversen et al., 2008; Stem et al., 1994), smaller hippocampal volume (Admon et al., 2009; Ball, 1977; Bizzozero et al., 2012; Bremner et al., 2003; Douglas, 1995; Gilbertson et al., 2002; Lindauer et al., 2006; Small et al., 1999; Vaisvaser et al., 2013; Woon et al., 2010; Yehuda et al., 2007) and dysfunction of frontal and parietal cortical regions (Frackowiak et al., 1981; Shin et al., 2005; Weber et al., 2005; Zubieta et al., 1999) are associated with both PTSD and dementing illnesses. Lower IQ, impaired attention, and memory have been observed in early and chronic stages PTSD and comorbid depressive symptoms, and both worsen over time suggesting acceleration in age-related memory impairment (Brandes et al., 2002; Mittal et al., 2001; Yehuda et al., 2006). For PTSD the BCCS will include data streams that take into account the natural heterogeneity of trauma response. We will call these multi-level data streams Target of Dimensional Measure (ToDM). Each ToDM represents a group of data streams, which represent brain output, that are of particular interest in post trauma responses. Here we present a list of ToDMs that could be used in the LEAPS study, but keep in mind one of the important features of the consortium is to bring together multidisciplinary expertise to collaboratively agree on the optimal measures and targets of interest. The list below gives preliminary ToDM that will be further refined and finalized in future work.

By utilizing FCU, it may be possible to understand fundamental properties of brain information processing before the neurophysiological and molecular complexities. It is essential to understand that the FCU cannot be simplified down to a single neuron; it is a combination of the quantitative differences between these neurons and neural networks. There exists a language between neuron levels and these "words" that are translated from neuron to neuron allow for the recall of memory, which in turn encodes sensory recollection. An individual's basic unit of thought is defined in terms of biological structures. These structures create building blocks to form the Fundamental Code Unit's role in producing thought. In order to map the phenomena of cognition, the function of unary values ("unary plus"+, "unary minus"−) increase or decrease in value, to represent cognition. The brain communicates with itself and with the rest of the body utilizing these unary operators. The path is simply this: information is coded using the FCU and travels from positive or negative cognitive constructs to action potentials in neurons to neurotransmitters, DNA and proteins and may eventually be governed by quantum effects. The FCU corresponds with synapse interactions and activation as well as protein exchanges between neurons. The way in which the exchange of a protein occurs depends on the structure of this linguistic expression; thus cognition is essentially reflected at this biochemical level. The FCU system models the mediums of brain function to provide a unified multi-level model of information Exchange.

In order to incorporate these different methods of analysis to better diagnose PSD, a new system has been developed called the Brain Code Collection System (BCCS).

CONCLUSION

The proposed BCCS incorporates the BC framework, which inherently includes the FCU, and clinical data streams such as speech and facial feature analysis. We suggest that this would produce a comprehensive, diagnosis method more accurate than current standards used by physicians. The complete BCCS entails three parts: 1)non-invasive collection of multi-level data 2) integration of these multiple data streams, and 3) application of multi-level paradigm analyses. The BCCS will collect multi level data using non-invasive hardware to collect large amounts of clinical and physiological data. Too often this data is rejected and cast aside, because initially you are presented with raw, segmented, quite massive amounts of data. Individually each stream is weak, fragmented and does not offer much value, but by integrating all these streams onto the same coordinate plane a far more precise and insightful analysis would be possible. Imagine the ability to capture hundreds of thousands of data points that span the central nervous system and in a few minutes, then be able to transform all these disparate data points into a simple objective measure or reading of PSD diagnosis, within a few more minutes. While this and the concept of a "Brain Code" may sound like an inconceivable, abstract idea, it does in fact exist within a valid infrastructure. Human brain activity is in fact composed of physical and chemical operations that can sometimes be observed and measured. Besides turning to invasive means of neurosurgery we cannot access the brain directly to observe or measure it, but we can access its output—our behavior. After all, behavior, movement, speech, and cognition are a direct product of our brain activity. By designing data units, data acquisition hardware, and novel cognitive data structures, we propose the collection of high quality data and novel analysis to better understand this interactivity and its changes in response to trauma. The significance of the BCCS is that it provides a novel approach to data acquisition that is designed to be non-invasive, timely, and cost effective and doesn't involve any biological specimens. By incorporating multiple data streams, more than one biomarker can be collected simultaneously and indicate measures of diagnosis, management and treatment, may be even resilience as well.

The methods we describe in this proposal have been in development for over a decade, with roots in military science and command and control technologies. These methods have evolved into a methodology and research design philosophy we call the BCCS. We propose that a more objective detection of PSD may be possible using the BCCS. Section 2 will discuss the theoretical concepts essential to the BCCS, including prediction, axiology, and temporality. Section 3 will discuss the approach and study design of PTSD Diagnosis using the BCCS, namely the targets of dimensional measure (ToDM). Section 4 will detail the specific methods used by the BCCS including language analysis, MSI/LXIO, and machine learning. Section 5 presents 2 BCCS preliminary data studies using the BCCS and machine learning to diagnose PSD and related conditions from text and facial feature analysis. Section 6 presents the proposed future work of BCCS, the LEAPS consortium. This section includes a detailed work plan of BCCS study to validate ability of BCCS to detect PSD, diagnose PSD, and differentiate comorbid conditions.

Section Two: Theoretical Foundations

The proposed BCCS relies on several essential theoretical concepts that lay the foundation for the approach and methods presented in this thesis. This section will discuss theoretical building blocks of language, and temporality that make up the BCCS.

Prediction

Predictions can be made in a number of ways. Dynamic prediction, first postulated by Newton and Leibniz, was successfully applied to the movement of planets and their satellites and, since then, has become the greatest predictive method in applied mathematics (Xiang, 2008). Its scope is universal: all that is material, all that is in movement can be studied using the tools of dynamical systems theory. The current state of a system is described as the result of its previous stages. The theory of dynamic systems can therefore be applied to prediction and retrodiction. In order to do so, one must know both the present state of a system, as determined by a set of predetermined state variables, and its law of motion, which generally consists of an ordinary differential equation or a partial derivative equation that enables calculation of the system's future states from its present state. If time is represented as a discrete variable set $t, t+1, t+2 \ldots$, then the law of motion is determined by a function of E, where E represents the dynamical state space. If the system is in state x at time t, it follows that it will be in state f(x), f(f(x)) and so forth in future moments.

Prior to the technological age, applying dynamic prediction was limited to relatively simple systems because calculations were too complicated. With the advent of computers, however, dynamic prediction has been applied to complex systems. In some cases, for instance meteorology, there have been remarkable results. Most systems are as complex as meteorology, but there are no means available to study them. Dynamic prediction is generally not applicable because the set of state variables cannot be determined and its laws of motion are unknown. Moreover, even if this information were available, it could not be verified because the state variables would be too numerous to be measured. What's more, dynamic prediction often only provides good results for short-term calculations, even if all the state variables have been accurately measured and there is full knowledge of the laws of motion. Precise knowledge of the system's dynamics is not enough to guarantee that the real-life experiment will turn out to be identical to the digital experiment, due to sensitivity to initial conditions.

Although dynamic prediction is universally applicable, it can be quite limited. Rational prediction is a much more effective predictive technique owing to its inherent flexibility. It trims off all excess calculations involved in the heavy lifting of dynamic prediction, such as the exact dynamical state of the system, and leaves only the essential facts. Generally, one can separate all the system's future states into two categories: the first including all the states for which the required functions are fulfilled, and the second containing all the remaining states; in other words, success, and failure. It is not necessary to know the exact future state of the system, only that it will fall within the "success" category. It is a trade-off between complete accuracy and the ability to make long-term predictions.

Generally, one can separate all the system's future states into two categories: the first including all the states for which the required functions are fulfilled, and the second containing all the remaining states; in other words, success, and failure. It is not necessary to know the exact future state of the system, only that it will fall within the "success" category. It is a trade-off between complete accuracy and the ability to make long-term predictions.

There is significant evidence in PTSD literature to suggest that major obstacles such as differential diagnosis of large numbers of patients can be achieved by incorporating analysis of context-independent factors such as vocal tonality and pause frequency into patient assessments, as well as other linguistic features that vary with subject matter being discussed.

In addition, while most methods that work along these lines are intended simply to supplement the diagnostic abilities of human clinicians, the evolution of superior algorithms based on human brain structure and function promises to make machine-based diagnosis a much more important aspect of the diagnostic process. Natural language is a particularly promising domain in which to seek a solution to meet this need, because it is possible to interact directly with the patient's affected cognitive constructs.

Predictive Linguistics

Predictive Linguistics deals with the conceptual, perceptual, and intentional factors that are specific to a particular tongue or individual (Bergmann and Howard, 2012; Howard, 2007; Howard, 2011c; Howard, 2013e; Howard et al., 2009; Howard and Lieberman, 2012). While natural language has evolved to include sophisticated semantics, there are a series of core grammatical and lexical concepts that have remained the same over time. These are linguistic 'primes,' which exist both at the word and sub-word level. At the sub-world level there is a demonstrable analytical bias towards specific letter and phoneme types among western language speakers (New et al., 2008). New et al. found that "French and Italian adults were able to track transitional probabilities at the lexical level in a context of fixed consonants and variable vowels, but not the other way around" (2008). They concluded, "the scope of the consonantal bias at the lexical level is not even limited to the speech modality. It actually extends to lexical access through reading." By adopting this perspective as a framework, natural language content could be a potential platform for detecting PSD.

Axiology and Semantic Primitives

When we study axiology, we examine the quality or value that people assign to concepts. The natural language processing module of the BCCS (MSI and LXIO explained later) aims to integrate the principles of axiological value using mathematical rigor. THE BCCS aims to investigate which concepts and expressions are "positive" and "negative" based on cultural and situational context. The most central question of axiology, and which we seek to answer as we assign numerical values to the concepts we encounter in patient evaluation, is what we can consider intrinsic value, and what we can consider instrumental value. Examples of opposite values include Virtue/Vice, Love/Hatred, and Praise/Critique. One of the most important characteristics of value, which any axiological analysis must address, is its relation to categories such as: right, reason, rational, just, and ought.

According to teleological views, it is sometimes said that things are consequently positive in virtue of their perceived "good" consequences. Within the LXIO framework, we seek to provide a computational explanation for cognitive states in terms of their relation to their expression in the common sense, not just in the terms of "true" versus "not true". We try to explain psyche in terms of "axiology", that is any state of mind that can only be understood and predicted if a larger system of expression is also understood.

Human language goes beyond mere semantic features. That is, people tend to be more likely to consider positive "simple" as opposed to "complex", than they are to consider "simplicity" as opposed to "complexity" (since some objects or subjects may be "complex" and "interesting" at the same time). Howard and Guidere (2011) postulate that "language is the container of our intent" (Howard and Guidere 2011). This fact suggests that there is a latent "value", made up of cultural attitudes, expectations, and background assumptions, which is part of language and emotional meaning that extends beyond linguistic and even contextual face value.

The base mind state, which we denote the default axiology in mind, consists of a set of beliefs that are predictable from rules. That is, feeling expression is organized with conventional values and perceptions of the world, which may or may not fit reality. One's cognitive state is relative to their beliefs, desires, and personal reasoning, each of which is shaped by culture and context as well as the individual. By appealing to these internal logics, we can use predictive cognition and linguistics to capture the meaning of the overall state as a trend of possibilities, which is the probabilistic world where the individual lives symbolically.

The BCCS's language analysis tool uses a system of quantitative values to map words to feelings. The axiology used to predict cognitive states is a formal representation of a set of concepts within a domain that is mapped to their perceptions as expressed in language. It is used to reason about the properties of the cognitive state, and may be used to define the cognitive state. It provides a shared conceptualization, which we can use to model the type of state of mind.

Interpreting Axiological Values

In order to interpret this information, the probability of a particular value is equal to the numerical translation of a particular knowledge state, which, despite being subjective, has been attained via a rational process. Interpretation illustrates the uncertainty when dealing with incomplete information on the circumstances and causes of a state. Such values could have been verified based on past states. Despite the same mathematical rules being applicable independently of the chosen interpretation (+/−), the choice has important practical implications: Are we referring to an actual cognitive process or just to a perceived one? And is it impossible to answer that question since differentiating between actual and perceived states is in itself subjective?

Temporal Axiological Values

A temporal axiological value is a series of numerical values that represent the evolution of a specific cognitive state over a period of time, and which can be expressed mathematically in order to analyze the behavior and predict future behavior. As this is a new discipline, in-depth psychometric studies have not been conducted. Nonetheless, the concept of axiology has long been used in philosophy as well as ethics.

Temporal values can be applied to the creation of cognitive axiology. The actual values are not proven, but there is the possibility of doing so later on. Using this approach, the premise differentiates itself from the axiom by the fact that the latter is always the fundamental element of the system, which does not require proving. We can therefore use this value premise with the consent of the subject, who considers it a principle that, despite not being proven, is legitimate because it cannot be argued with, or because it has already been proven through other experiments. Most value premises are backed by logic or experience.

Axiological Values

The focus of axiology is studying cognitive variables overtime. Its main objectives are to define trends using temporal series and find when the values will vary or be stable over the course of time. The need to integrate temporality into the analysis of cognitive processes stems from the lack of predictive methods provided by classical models of psychology. Accordingly, predicting cognitive states can be likened to the ARMA (Auto Regressive Moving Average) model developed for the field of economics in 1970 (Box and Jenkins, 1970). In order to predict the cognitive state of a particular subject in two years' time, it is not sufficient to use a structural model that explains the state being analyzed (depression, trauma, etc.). With the ARMA model, the cognitive state can be predicted using axiomatic state properties (e.g., average values and divergences). Frequently, this model utilizes past values of the cognitive process (hence, the "auto-regressive").

The ARMA model is a specific model stemming from a more general one called ARIMA (in which "I" refers to "Integrated"). Whereas the ARMA model can only be used with stationary series, the ARIMA model can be applied to non-stationary series once the level of integration has been determined (i.e., the number of times the series must be different before it can be set). Despite being excellent predictors, the ARIMA or ARMA models have one major drawback: they are incapable of dealing with more than one variable (series) at a time. For instance, classical models are able to answer a question such as: What effect does a traumatic event have on a bi-polar subject?

One of the major questions in the study of temporal values is knowing whether they are part of a stationary process; in other words, whether the underlying structure of cognitive process changes over time. If the axiological value remains the same, the cognitive process is said to be stationary. If the process is stationary, its properties will not be affected by a change in temporal reference point. The same behavior will be observable regardless of whether we are evaluating point t or point t+k. Whether the process is stationary is important in the modeling of temporal values: it plays a decisive role in predicting future cognitive states because the prediction interval is dependent on the immobility of the value.

For example, if we were to think of “Sky” as a concept set and in order for us to determine what its axiological value is we need to follow the current procedure. The concept “Sky” is a resultant of various activation sets in which each contribution was based on the level of its activation within a specific time frame and orientation. If we were to consider another concept such as “Dark” most likely the same computation applies but a negative axiological value would be assigned. At another point in time and according to the same patient the concept “Morning” can be formed based on these two concepts and it will result with a positive axiology since a “Dark Sky” might resemble the end of a day and hence announcing the coming of the “Morning”. This axiological value is valid within these time-division constraints and it might change if the constraints were to change, similarly for other patients. Therefore, the use of a learning algorithm will enhance our computational accuracy while reducing evaluated errors for specific patients.

Temporality

Analysis and Perception of Time

Although humans do not have any body parts dedicated to the perception of time, we are somehow capable of perceiving its passage. Research on the perception of time is thus confronted with a paradox concerning the nature of time itself and requires combining psychological experiments with philosophical thought and basic brain mechanisms. Researchers have been able to distinguish different types of phenomena, all of which elucidate human perception of time. They have examined the perception of intervals of time, the perception of periodicity, and the perception of temporal order and simultaneity.

In 1857, German psychologist Johann Czermak published a series of findings on what he called “sense of time” (Czermák, 1857). Using new methods in psychophysics, he tried to measure the shortest interval of time perceptible by different senses (sight, hearing, and touch), the way in which the same length of time was perceived by different senses, and the way in which the perception of an object’s speed varied according to the perception of space. These questions established the framework for the experimental study of “psychophysical time”. During the same period and throughout the second half of the $19^{th}$ century, Mach, Vierordt, Wundt, and Fechner also carried out experiments in an effort to determine if the perception of time was related to the perception of other physical elements. One of their first findings was that temporal perception more or less followed Weber’s law on duration.

Ernst Weber was among the first to quantitatively study the link between stimulus and physical sensation. Gustav Fechner paid homage to his work by naming the quantitative relationship that he discovered “Weber’s law” (their successors would however use both names when referring to it) (Weber et al., 1996). Weber’s construction of the relationship between sensation and stimulus is significant because it lends physicality to the notion of intention, and thus to intention awareness. Cognition is the primary agent in generating intention, and it is influenced in large part by environmental stimuli and in turn influences the response to those stimuli. In this sense, it is both a cause and an effect of environmental change, and the mechanism by which it is affected by the environment is neatly laid out in the Weber-Fechner law. Stimulus intensity can take any number of forms, but taken relative to an actor’s present intentions, a clear relationship between stimulus and intent becomes apparent. The Weber-Fechner law describes the quantitative relationship between sensation and stimulus. According to this law, perceived sensation is represented by the following equation:

$$S=k\times\log(I)$$

Where:

S=the perceived sensation

I=the intensity of the stimulation k=a constant

The experimental verification of the Weber-Fechner law could not be carried out, however, due to the introduction of the notion of differential threshold (ΔI), that is, the smallest difference in perceived intensity of a stimulus. This notion was introduced because it was observed that a subject did not always react to changes in stimuli when the changes were minute. ΔI/I, or relative differential threshold, is proportional to the size of the stimulus change, no matter how small. Therefore, $\Delta S=k'(\Delta I/I)$ where $k'=1/k$. The differential threshold affects experimental verification for small time intervals, but it is not a factor when considering large stimulus changes such as the passage of time in years.

Throughout the $20^{th}$ century, experimental psychology studied humans’ perception of time using new paradigms that compared their perceptions to data on that of animals. Through adapted experiments, it was discovered the laboratory animals (mostly rats, pigeons, cats, and monkeys) were aware of temporal relationships between events.

Pavlov’s experiments on conditioning had already shown that a dog accustomed to being fed a certain amount of time after a bell had sounded would salivate in anticipation of food. One of the protocols that highlight the chronometric capabilities of animals is peak procedure. In this type of experiment, the animal is trained to wait a certain amount of time before performing an action (e.g., pushing a lever) in order to get something. If it acts too soon the animal receives nothing.

Animals are perfectly capable of carrying out this exercise, proving that they too have a sense of time. Similar experiments then showed that the temporal performances of animals are also consistent with the Weber-Fechner law such that, even if there are differences in sensitivity from one species to another, it appears that perception of time in humans and animals has the same neurobiological basis. The question remains, however, whether these different temporal perceptions arise from the same mechanisms. According to French psychologist Paul Fraisse, “temporal perception” should be distinguished from “temporal estimation”, which refers to our ability to comprehend long periods of time (Ibid.).

As in other areas of experimental psychology, technology now plays an important role in research laboratories. The speed of electronic systems allows researchers to better control the introduction of different stimuli (visual, aural, etc.), an obviously critical aspect of experiments on temporal perception. In more general terms, technology makes it easier to collect and analyze data. Computer systems also provide important brain imagery tools, which are used in modern cognitive neuroscience. Electroencephalography (EEG) is one technique that has played, and continues to play, an important role in experimental research on the perception of time, since it provides access to brain activity with millisecond accuracy. This technology was able to highlight so-called slow electric waves (such as the Contingent Negative Variation wave) that appear while an individual is awaiting a stimulus.

Furthermore, improvements to the calculation capabilities of computers have allowed researchers to imitate hypothesized mechanisms in order to make certain predictions that can later be empirically verified with real data. Established models based on neural networks have shown that, under certain conditions, temporal information can be processed through neural circuitry without it being necessary to evoke a specific mechanism, such as an "internal clock." Several hypotheses on the subject clash, yet do not necessarily contradict each other. On the one hand, according to the "spatial coding of time" model, a certain number of neurons in the heart of the neural network are activated as one perceives stimulus. Temporal information is thus encoded by the number and position of activated neurons. In order for this model to work, a stimulus must always cause the same order of events, which appears to be the case according to studies conducted using computer modeling.

On the other hand, the "pacemaker-accumulator" model, created by Gibbon, Church and Meck and inspired by the cognitivist movement, uses a pacemaker that emits steady ticks or pulses (Gibbon et al., 1984). These ticks are "stocked" in an accumulator which then conveys the number of ticks to what is called a "reference memory". Next, the accumulator's content, which has been stored in reference memory, is transferred to the working memory, and is compared to the reference memory. Finally, the test subject compares the data for both time periods and determines (within a certain margin of error) whether the first period of time is longer or shorter than the second.

There were numerous attempts to ascribe neurobiological bases to the different operators occurring in the pacemaker-accumulator model. In its current version, it is accepted that there are specialized areas of the brain that process temporal information. Catalin and Meck suggested that the basal ganglia system could play the role of the pacemaker-accumulator while others, such as Ivry and Schlerf, insisted that the cerebellum, and particularly the cerebellar vermis, were crucial to the perception of time (Buhusi and Meck, 2005; Gibbon et al., 1984; Ivry and Schlerf, 2008).

Brain Code

The Brain Code (BC) relies on several essential concepts that are found across a range of physiological and behavioral functions. The Fundamental Code Unit (FCU) assumes an abstract code unit to allow for a higher order of abstractions that inform information exchanges at the cellular and genetic levels. Together the two hypotheses provide a foundation for a system level understanding and potentially cyphering of the Brain Code (Howard, 2012a; Howard, 2012e; Howard et al., 2013f; Howard et al., 2013s). This section discusses an organizing principle for an abstract framework tested in a limited scope experimental approach as a means to show an empirical example of cognitive measurement as well as a framework for a Cortical Computation methodology. Four important concepts of the BC and FCU are discussed. First concept is the principle of activation based on Guyton thresholds. This is seen in the well-known and widely documented action potential threshold in neurons, where once a certain threshold is reached, the neuron will fire, reflecting the transmission of information. The concept of thresholds is also valid in Weber minimum detectable difference in our sensing, which applies to our hearing, seeing, and touching. Not only the intensity, but also the temporal pattern is affected by this (Fitzgibbons and Wightman, 1982).

This brings insight to the second important component, which is duration. The combination of threshold crossing, and duration may define the selection mechanisms, depending on both external and intrinsic factors. However, ranges exist within which tuning can take place. Within reason, it can be stated that no functional implication will occur beyond this range. Transfer of information and processing itself relies on energy and can be described in waveforms, which is the third concept. The human sensing system acts as transducer between the different forms of energy, the fourth principle. The aim of the brain code approach is to incorporate these four principles in an explanatory, descriptive, and predictive model. The model will take into account fundamental physiological knowledge and aims to reject assumptions that are not yet fully established. In order to fill in the gaps with regards to the missing information, modules consisting of the previous described four principles are explored. This abstraction should provide a reasonable placeholder, as it is based on governing principles in nature. The model is testable and allows for updating as more data becomes available. It aims to replace methods that rely on structural levels to abstraction of functions, or approaches that are evidence-based, but across many noisy-elements and assumptions that outcomes might not reflect behavior at the organism level.

There is a seemingly contradictory characteristic of complex systems, whereby they appear strikingly simple at the unit level, but can achieve unparalleled complexity at higher orders. This is the basis of the Fundamental Code Unit (FCU) argument; an assumed abstract code unit to allow for higher order of abstractions, and provide a foundation for the Brain Code (Howard, 2012e; Howard et al., 2013f; Howard et al., 2013u) organizing principle model. This paper presents a low-level analysis of the phenomena that compose cognition, and the means by which we can better understand it. Here we begin with a discussion of the potential applicability of Brownian motion formulas to the uncertainty inherent in protein-driven neurotransmissions, for protein exchange occurs at a lower level than neural activation and is often a causal agent in neural activity. For instance, Rubinsztein (2006) demonstrates that the ubiquitin-proteasome and autophagy-lysosome pathways are the primary means of protein transmission into the organelles of neurons. The former are multiprotein complexes whose function is to degrade nuclear and cytosolic proteins. Rubinsztein also details the process of endoplasmic-reticulum-associated degradation (ERAD), in which misfolded protein is retrotranslocated back into the cytosol, where the proteasome pathway degrades them.

In a hypothetical model offered, each of these events can be appropriately captured by the introduction of Brownian motion methods, which currently have wider applications to models in imaging technology. The "Brain Code" is a higher-level analysis which consists of computational method whereby cognitive events such as neural spikes, network activation, and memory recall can be understood in terms of the simultaneous physical phenomena that cause them. As mentioned previously "brain language" is decoded from a combination of inputs (natural language, behavioral outputs, and electrical activities of the brain) yielding a comprehensive cognitive picture. Thus, the process described is essentially one of deriving enhanced insight from a series of fragmented, often incomplete streams of data. I offer reviews of several different analytical methods, along with examples of phenomena applications for each. Brain codes, such as cognitive state signatures or behavioral indicators such as movements and other behavioral expressions, continue to provide valuable insight into the patient's cognitive state even after higher motor and cognitive functions are significantly impaired. Thus, brain codes remain a common output to both functioning and impaired neural systems, unlike natural language expressions if used alone (Howard et al., 2013f).

Morse code is an appropriate metaphor to express the Brain Code paradigm, for it describes a simple code to express meaning and concepts however complex they may be. Yet it is basic in its structure. If we assume a Morse code is transmitted via many multiple modalities, and subsystems of the cortical universe, it will survive the molecular pathway journey and reach a higher function, such as language. Also, there is uniformity, as the structure must remain the same throughout any transmission. The unitary basis for conceptualizing the brain's combined throughputs uses the etymology of the Brain Code and the Fundamental Code Unit to offer a theoretical framework that supports advances of cortical computing. Essentially, the FCU hypothesis is an attempt to offer a system of code-methodology, which governs fundamental neuron communication across all brain activities, that which formed the fundamental unit of thought through evolution. Therefore, it is hypothesized that behavior, intelligence, cognition, and conscience are all products of and expressed using the same schema of coding in both stimulus processing and decoding.

A comprehensive model that can explain how high level functioning is affected by biological coding is currently underdeveloped. Encoding behavioral information from cognitive states is computationally possible using the "Brain Code" model. The Brain Code is designed to enhance our study and understanding of human cognition. Additionally Anderson (2010) proposes neural reuse as a fundamental organizational principle of neural networks in the brain. In particular, he suggests that structures and resources within the brain are often allocated according to current needs, rather than created on an ad-hoc basis. Functions sharing cognitive resources include "evolution and development of the brain, including (for instance) the evolutionary-developmental pathway supporting primate tool use and human language; the degree of modularity in brain organization; the degree of localization of cognitive function; and the cortical parcellation problem and the prospects (and proper methods to employ) for function to structure mapping." Anderson thus provides further support for the notion that the key to deciphering cognition lies in the ability to properly understand brain networks in their specific temporal contexts. To provide a superior understanding of cognition, one must demonstrate not only that these processes are related, but also show how they relate to one another.

To that end, the Brain Code (BC) framework we propose is a unified analysis of patterns in neural oscillation, linguistics, behavior enabled by simultaneous data stream acquisition and analysis. By causally linking sensory stimuli, cognitive activity, and cognitive outputs such as language and behavior, the BC framework maintains the networked structure of the brain, but is populated with units specifically relevant to cognition. Because we don't yet possess the ability to manipulate and interact directly with these networks, the Brain Code framework interpolates multiple data streams and modalities, including electroencephalography (EEG), speech recording and analysis, and movement analysis, to provide an accurate portrayal of the inner workings of the brain. This data fusion is superior to single-stream analyses for two primary reasons. The first is the incomplete and largely uncertain picture painted by many such methods. Linguistic analysis, for instance, can only reveal so much about the cognitive state of the individual, because language is a voluntary act that is controlled and regulated by conscious thought. Secondly due to language being a voluntary act, the cognitive state will not always be evident in speech. By expanding cognitive state and cognitive analysis to realms that are less under conscious control, such as recurring movements behavioral and neural oscillation patterns, it is possible to develop a more complete picture of the mind, as well as deviations between conscious and unconscious mind processes to discern state of order or disorder. The brain code will initially apply machine learning. Despite the limitations it will provide a means to determine the most relevant features and provide a prediction of future behavior. Future work will evaluate additional methods to include the testing of additional BC specific wavelets.

Brain Code Defined

While Brain Code is an abstract phenomenon in that it is a human cognitive construct, it is composed of physical and chemical phenomena whose interactivity is still not well understood. By designing data units, data acquisition hardware, and novel cognitive data structures, we intend to demonstrate in this section that, given high quality properly formatted data, we can shed light on this interactivity. In addition to the methods outlined in this paper for analyzing individual data streams, a key component of brain code derivation is tracing the relationship each of these data streams has with the others. Shibata et al. (2011) present an FMRI neurofeedback method for inducing visual perceptual learning that bears relevance to my position in that their findings contain two important implications first, visual perceptual learning (VPL) in the early visual cortex of adult primates is sufficiently malleable so that fMRI feedback can influence the acquisition of new information and skills when applied to the correct region of the brain (Shibata et al., 2011).

Second, these methods can induce not only the acquisition of new skills and formation, but can also aid in the recovery of neurological connections that have been damaged by accident or disease. For instance, a trauma victim suffering from language skill loss can potentially recover those skills through fMRI neurofeedback induction. BC method seeks the same state clarity in cognition, yet furthermore proposes that cognition on the processing level must be based on some finite number of neurological connections—those same connections influenced by the activity of fMRI neurofeedback. *Ibis* process does not target a single neuron, but rather a locality of connected neurons, and based on its positive effects on the conscious process of Visual Perceptual Learning.

Shibata's fMRI could be an induction to research that could provide powerful evidence for the composition of thought because it can be used to determine the minimum amount of neuronal connectivity for the formation of thoughts. In today's state of the art technology, our primary means of monitoring activity within the brain is to measure the electromagnetic phenomena produced by the brain's activities. Electroencephalography, for instance, allows identification of the brain areas and networks activated by the patient's responses to specific stimuli. In most research settings, these stimuli include hyperventilation, visual stimuli such as flashing lights, directed mental activity, and sleep pattern manipulation. While EEG and similar real-time brain monitoring methods may appear to be the most promising avenue of clinical brain and cognitive research, technology has not yet matured to the point of providing sufficient spatial resolution to identify specific neural webs that are being activated by certain stimuli. For that reason, EEG is often used in broad category diagnosis such as the identification of comas, encephalopathies, and, in some cases, brain death.

These disparate methods beg an important question: how do we extract brain code from these data streams? Because none of these methods can provide a complete brain code by themselves, it is important to develop a method that allows each to compensate for the others' shortcomings. For instance, EEG monitoring alone cannot reveal the precise conceptual neural webs being activated during exposure to a stimuli.

However, as quantities of data rise, pattern analysis based on a combination of electroencephalographic monitoring, linguistic assessment and behavioral tracking can identify those concepts from a cognitive perspective, as well as the neurological phenomena related to them. For example, a patient suffering from cynophobia (abnormal fear of dogs) will reveal aberrant EEG readings when shown a picture of a dog. However, EEG alone will do little more than to identify a disorder that is already obvious to a clinician. If we combine behavior and linguistics into this assessment, we can create an "informed self-report" based on a brain code, in which cognitive state analysis is conducted alongside the patient's own speech output.

Self-reporting may reveal a traumatic incident with a dog early in the patient's life, and linguistic analysis of that self-report, along with behavioral data can identify further the source of the cynophobia, whether it was the result of a single experience, long-term conditioning, or concept conflation. A brain code analysis of a patient such as this would include thorough EEG testing using a broad spectrum of dog-related sensory stimuli, in addition to linguistic analysis of the patient's self-report and an IMU-based assessment of body language.

In the cynophobia example, we expect that a patient shown pictures of dogs as stimuli (or perhaps shown a live dog in a controlled environment) would have EEG signatures pointing to an activation of the amygdala (recalling a remembered fear reaction such as anticipatory anxiety), as well as activation of the hypothalamus. Behavioral analysis based on movement patterns captured with inertial measurement units (IMU's) would distinguish the patient's behavior as part of a learned pattern or spontaneous, and mind-state analysis of the context and content of the patient's linguistic output would yield further insight about the nature of the patient's fear.

Fundamental Code Unit

To understand the FCU approach, we need to establish a mutual understanding of the nature of sensory information processing in the brain. Brain information processing of incoming sensory information (such as speech sounds) can be viewed as the following step-by-step process: Sensory transduction—e.g., converting speech sounds into electrical information transmitted to the brain via the auditory nerves. Conversion of that information into intelligible language that our mind (whatever that may be) can comprehend as records of events, concepts, stories, and so on. For the visual system, that language is a series of images, discerned as objects that may move, emit light, etc. These patterns provide an understanding of our physical surroundings. Analogously for the auditory system, the conversion process to language can be considered as discerning a series of sounds as speech, expressed in patterns that consistently correlate with specific objects, feelings, and thoughts. Those meaningful representations can be communicated to and from others, based on a common understanding of what those speech sounds signify—language. Storage of those meaningful patterns as meaningful thoughts are done as a series of both images and auditory language representations within the brain. Retrieval of those meaningful thought patterns is either at will or involuntarily. The latter case refers to spontaneous thoughts, our constant internal dialog which can at times be distracting and prevent us from concentrating on what we find meaningful and important To offer an example, autism spectrum disorders (ASD) are strongly tied to genetic identity. However, like many others such as ADHD, schizophrenia, and certain other disorders, it's underlying cause is not tied to a single gene as is the case in Huntington's Disease which belongs to another class of ndd with complexity in cause in symptomology.

On the cellular & molecular level, the etiology of the disorder appears equally diverse and complex. Adding to the challenges of developing new therapies for ASD—or improving current ones—is the fact that the key underlying cellular & molecular mechanisms—such as those responsible for transducing speech sounds into mutually understood and remembered language within the brain—have not yet been clearly defined. Using the advances in AI techniques that are increasingly grounded in the reality of brain physiology, such as new neural network algorithms NLP or others briefly discussed here will greatly benefit and aid the discovery of new methods and processes to reach meaningful solutions. We will have distinct categories based on their underlying etiology, more intimately correlated to each of the multiplicity of mechanisms that can give rise to the speech and behavioral abnormalities characteristic of many of those brain disorders.

It should also serve as a guide to the development of new therapeutic strategies on an accelerated time frame, based on the ability of the brain to rewire itself in response to experience—neuroplasticity. Such neuroplasticity-based therapies do not require detailed mechanistic knowledge of brain function abnormalities. In certain forms of ASD, there appears to be hyperactivity of spontaneous internal thoughts, images, and ideas, and this may contribute to the observed symptomatology. In all forms of ASD, language deficits and image recognition deficits (e.g. The inability to make sense of subtleties of human facial expression) are hallmarks of that symptomatology.

In the $19^{th}$ century, Darwin's insightful outside-in observations of life's diversity in time and space gave rise to the notion of inheritable characteristics that could change over time—genes, a fundamental coding unit dictating those characteristics that could change (mutate) over time, giving rise to systematic changes promoting environmental adaptability, and eventually giving rise to new life forms—i.e., evolution. Also in the $19^{th}$ century the outside-in research of Gregor Mendel and others homed in further on the nature of the gene, specifically its role in the expression of discernible characteristics by parental inheritance.

By the 1930's, prior to DNA being discovered, those fundamental units were shown by light microscopy to reside on chromosomes, and we had a basic view of the cellular phenomenology of genetic inheritance and genetic abnormalities. In genetics, before our current detailed cellular and molecular-level view of genetics was obtained—before DNA was discovered to be the unit of genetic information coding, storage, and expression—a great deal was known about the nature of the gene as a discrete, fundamental coding element, dictating a wide variety of inherited characteristics, both physical and mental. Long before we had an inside, molecular level view of the fundamental coding unit, DNA, we had a detailed outside-in view of the gene, a view that proved quite useful in many ways.

How might this historical analogy to the field of genetics relate to brain information processing? This question is key to the FCU-based strategy for understanding brain information processing and its abnormalities, by analogy with the historical success of understanding the properties of genetic information encoding in the brain, the FCU-based strategy is based on this premise: In the face of limited but advancing understanding of brain information processing on a molecular & cellular level, our novel FCU approach addresses the problem from an entirely different direction.

To help appreciate this dualistic approach, by analogy we can compare the FCU brain information strategy to the field of genetics, as viewed from the outside in (observations of the evolving characteristics of organisms) vs. the inside out (the structure of DNA and the dynamics of its translation into the protein elements comprising the organism's structure and metabolism, etc.). FCU-based strategy for understanding brain information processing may reveal fundamental properties of brain information processing, long before the molecular and neurophysiological complexities of the brain's information processing pathways and processes are fully revealed. There exists practical advantages of viewing human consciousness as an abstract concept, as well as a biological entity embedded in the brain—

Isaac Newton's discernment of universal laws governing motion. In this 17*th* century world, the motions of heavenly bodies seemed unmanageably complicated. Astronomers such as Kepler developed elaborate schemes to describe such motions, but such schemes offered little in the way of fundamental understanding of said complexity. Newton came along, and used his mathematical talents together with other gifts to propose that these motions could be more meaningfully described if one were to postulate the existence of an all-pervasive, universal force—gravity—that exerted its actions on heavenly bodies by universal laws that could be represented mathematically. As we know, this insight greatly simplified the apparent complexity of planetary motion, and to this day has proved of great value in predicting the orbital trajectory of satellites, etc. All this was done in the face of a lack of knowledge (strikingly incomplete even today) of the physical nature and origin of this gravitational force. Gravitational field theory was developed solely by—yet again, as in the discovery of the gene—the outside-in approach of observing its effect on bodily motion.

How does Isaac Newton's approach bear relation to FCU-based approach to deciphering the complexity of information processing in the brain? Again in this case, neuroscience has told us a great deal about the brain's molecular and cellular pathways and processes associated with information processing, but the inside view is still too incomplete to provide a unified view of the coding and handling of information in the brain. By viewing the brain's ability to import information and process it into thought patterns and concepts meaningful to human conscious awareness as an abstract concept—approaches akin to force field theory of physics, cutting edge tools of mathematics and computer science can be productively brought to bear on human neural information coding research in health and disease. We can usefully model human consciousness as a mathematical abstraction, whose underlying properties can be revealed through an analysis of its manifestations in the form of language and behavior.

A prerequisite for the connectivity analysis proposed above is the ability to define networks, in terms of foci where activity relevant to a task is to be found and the connections between these areas as they are defined anatomically and functionally. There are many ways of defining how nodes are related, e.g., through phase relationship or amplitude modulations, directed or undirected and with or without time delays. Each of the different sensible ways of defining a metric for the inter-dependence between nodes poses a distinct question and many such questions must be addressed at any one time. We have used tomographic analysis of MEG data to identify the nodes of the network since we have already demonstrated that we can identify activity from the MEG data with high accuracy (Moradi et al., 2003).

Recent work has focused on eye movement in awake state and sleep processing in the visual system (Ioannides et al., 2004a; Ioannides et al., 2005), because eye movement and the visual system are the only systems we understand reasonably well to attempt a serious modeling with the graph theory as outlined in Ioannides (2007) and (Ioannides et al., 2013). Studies in the visual system have covered a wide range of stimuli including simple stimuli like checker board patterns (Moradi et al., 2003; Poghosyan and Ioannides, 2007; Tzelepi et al., 2001) occluded figures (Liu et al., 2006; Plomp et al., 2006) illusory contours (Bakar et al., 2008) and a series of studies on face and face affect recognition, both on control (Ioannides et al., 2000; Liu et al., 1999) and schizophrenic subjects (Ioannides et al., 2004c).

It was clear from these studies that it would be necessary to also deal with controlling the state of the subject. For these reasons a series of studies were undertaken on sleep (Ioannides et al., 2004a; Ioannides et al., 2009) and attention (Ioannides and Poghosyan, 2012; Poghosyan and Ioannides, 2008). Finally two cases were studied where the visual system was studied in extreme conditions, where damage probed its operations under conditions that were beyond what the system was optimized for evolution for maximum efficiency. In the first case the hemianopic subject GY was studied with stimuli presented to the intact as well as damaged hemisphere, and thus allowing the identification of spatiotemporal profiles of visual processing with and without primary visual cortex (Ioannides et al., 2012).

Research by Ioannides and his team was based on the observation that simple and complex tasks alike (regardless of whether they involve motion, concept processing or both) necessarily involve the activation of and communication between multiple brain areas. While some neural networks are permanent in structure and function, most of the ones involved in these tasks contain components, whether individual cells or sub-networks, which are members of multiple larger networks. Complex and dynamic information and data networks such as the human brain share many characteristics in common, such as recurring patterns, as well as sudden changes, or shocks, that can redefine the structure of the network, or simply alter it. Ioannides et al. used a modified functional coupling measure method in order to take "snapshots" of neural connectivity from signal.

FIG. 1 illustrates an example of a flattened occipital cortex. The left hemisphere flattened patches are shown on the left and the right hemisphere patches on the right. Colored shapes mark centers of ROIs obtained in response to stimuli presented in different parts of the visual field, as depicted on the upper right part of the figure. Cyan and yellow shapes mark ROIs corresponding to stimuli presented at eccentricities of 4° and 9° respectively. Triangles, rhombi, and circles indicate ROIs for stimuli presented on the horizontal meridian, vertical meridian and in the quadrants respectively. Filled and empty shapes indicate ROIs for stimuli presented in the upper and lower visual fields respectively. The markings for estimated visual area borders are indicated on the example flattened patch on the upper right part of the figure. White lines indicate borders between early visual areas estimated based on source analysis of ME G data alone. Black lines indicate the borders between areas V 1 and V 2 estimated in independent fMRI experiments. Putative V 4 and V 5 areas obtained from the above 50% cytoarchitectonic probabilistic m aps are also indicated on the flattened patches. (A) Shows distribution of R O Is in a typical control subject. (B) Shows distribution of R O Is in G Y. Crosses m ark the locations of the three high-level R O Is in the ipsilesional hemisphere. The black patches show the lesioned portion of the left occipital cortex.

These snapshots usually consisted of time windows in the 100 ms range, which were then progressively moved forward to track the change in computed values (local efficiency between attended and ignored conditions) over time. Time-window width was calculated to be 2 cycles of the lower frequency. The work of Ioannides et al. is particularly relevant to cortical computing and the brain abstract code because it helps bridge the analytical gap between computational networks and structures outside the human brain, such as man-made data representations, and the neural processes that occur within the brain.

Figure 2:
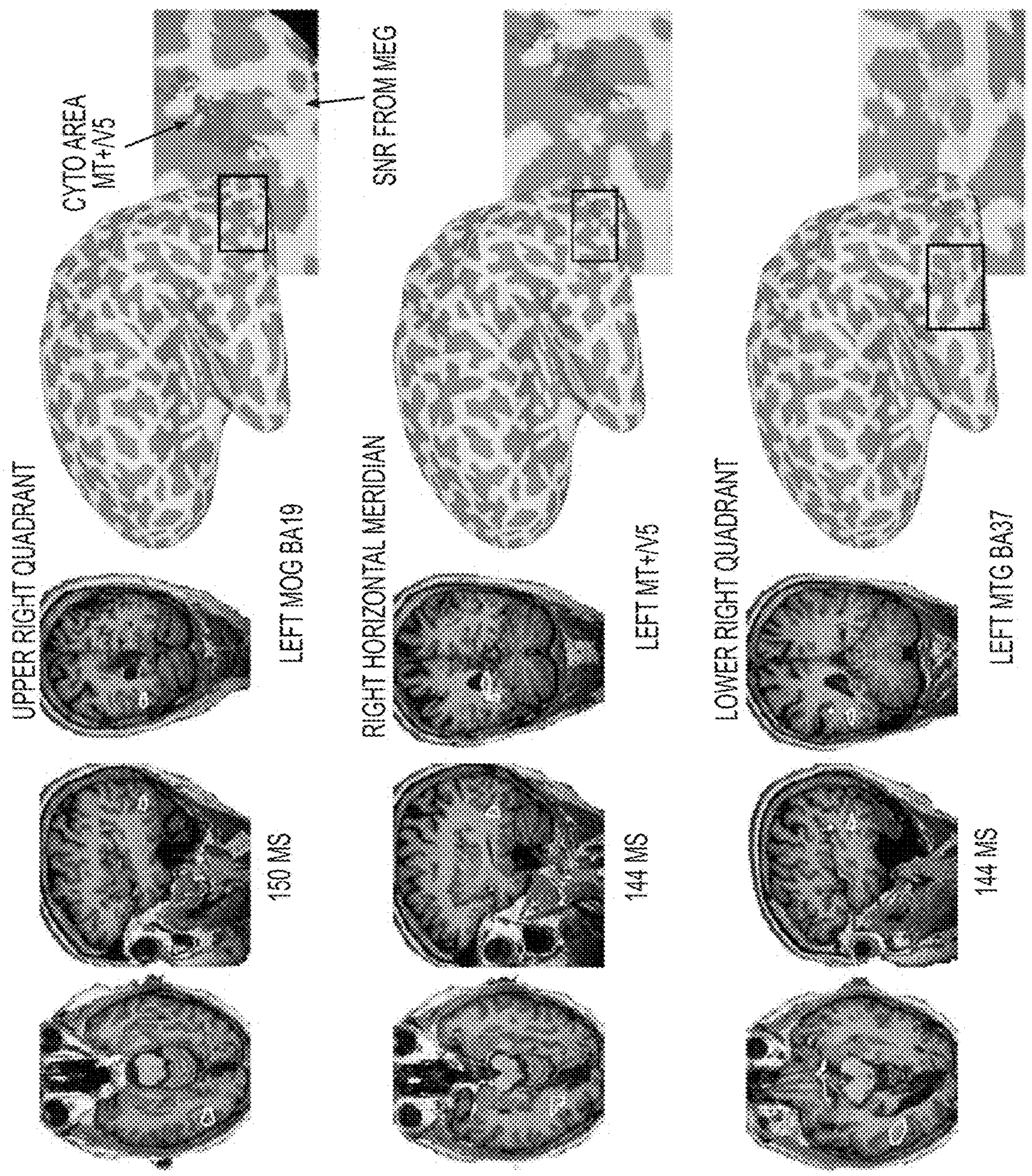
FIG. 2 illustrates an example of the first activations in response to "unseen" stimuli in the blind hemifield of G Y.

FIG. 2 illustrates an example of the first activations in response to "unseen" stimuli in the blind hemifield of G Y. The first activations (SNR>0.2) elicited by stimuli presented in the U R quadrant (upper row, M O G B A 19), on the R H M (middle row, M T+/V 5) and in the LR quadrant (lower row, M TG B A 37) are shown on the M R I and lateral aspect of the inflated cortical surfaces of the left hemisphere. Note that the first responses to all three "unseen" stimuli were in the ipsilesional hemisphere. Axial (left), sagittal (middle) and coronal (right) M R I slices best covering the relevant activations are shown. The yellow contours on each M R I view encompass the regions with SNR>0.2. Activation latencies are given below the sagittal view s. The black rectangles on the inflated cortical surfaces indicate the zoomed areas shown in their lower right part. Putative V 5 area obtained from the 50% cytoarchitectonic probabilistic m aps is also shown in the inflated m aps and they are captured also on the first and second zoomed views. All the mentioned studies can be considered as preparatory for the implementation of the approach outlined in Ioannides (2007) "Dynamic Functional Connectivity." It represents a solid volume of work demonstrating that the elements to build a proper graph theoretical approach are in place. It also testifies an unparalleled wealth of M E G data already collected that can provide the foundation for the m ore extensive work on subcortical functional interaction and connectivity (FIG. 6. in Ioannides et al. (2012)).

By modeling both types of systems using similar methods (i.e. graph theory) to describe similar phenomena, they demonstrate that the network-based methodology used by the brain code to describe brain activity is sufficiently complex and efficient to accommodate neural activation, even in highly volatile states.

Where the primary objective of Ioannides et al. was to provide a network-centric model of brain processes, ENREF 20 Marx and Gilon (2013) show a biochemical basis for understanding those same changes in neural networks over time. While both of these authors lend implicit support for the cortical theorem, Marx & Gilon show a physical basis for theoretical underpinnings, such as a unary mathematical system describing neural connectivity. Marx & Gilon's method, which is based on a three-part model of memory engrams, focuses on individual neurons and neural neurons, extracellular matrices, and chemicals that affect the activity of these matrices as a means to prove the brain code algorithm to reach a Fundamental Code Unit (FCU) as proposed by Howard (2012e).

Where a proposed cognitive minimum assumes an abstract code unit, a minimum to allow for higher order of abstractions that informs information exchanges at cellular and genetics level, together with his twin hypothesis of the brain code method and the Fundamental Code Unit, Howard (2013k) provided a foundation for a system level understanding and potentially cyphering of the Brain Code. Termed "Neural extracellular matrices" (nECM's) Marx and Gilon's (2013) method for describing chemically encoded information transfer is based on a hydrated lattice structure manipulated by neurons using electro-elastic processes.

While current research has not addressed the role of electroelastichydrogels in specific memory applications, it is particularly important to note that the networked structure of both these lattices and the larger neural networks with which they interact, operate on largely the same set of rules. Thus, the same-based cortical mathematical system used can be applied to hydrated lattices. Furthermore, the multilevel analytical function is born out of the independent arrival of two disparate research efforts focused on different brain phenomena which arrive at the same conclusion. If a Brain Code (BC) exists it will have to rely on several essential concepts that are found across a range of physiological and behavioral functions.

Modeling with the graph theory as outlined by Ioannides in (Ioannides, 2007) and (Ioannides et al., 2013) offers a data driven proven and tested methodology towards empirical evidence that supports the existence of cortical microcircuits that implement these models of computing primitives, as disused in aspects of the models where microcircuits in the brain have been examined and modeled. Our current method if further supported could yield significant advances towards identifying what is the minimum set of new information about cortical microcircuits that would significantly advance the state of the art connectivity, synaptic weights, glial distribution, neuromodulator state, gene expression, neural activity patterns, etc.

Twin Hypotheses

Python codes developed to date based on the Brain Code methodology contain two functions for time-frequency analysis and machine learning classifiers. It is necessary to show in a single equation or method that there is utility in using a brain code approach instead of current machine learning (ML) methods; here I have suggested the use of wavelets to show where the work will progress after ML. Wavelets are more specific to the application of BC. Work done to date on fusing multiple data streams within the brain code approach focused and tested affect data, which is easily extendable, but requires additional data analysis to validate. The first step was to focus on the predictive algorithm. A specific type of Markov chain, called a Hidden Markov Model (HMM) was applied where the states are unknown, and therefore are "hidden", however the emissions from the states are observed. HMMs are composed of hidden states, $S=\{1, \ldots, N\}$, transition probabilities, $a_{ij}$=transition probability from state i to state j, and emission probabilities, $b_j(o_m)=P(\text{emitting } o_m|S=j)$. Similar to Markov chains, HMMs also are based on the property that at each time step t, the future state $S_{t+1}$ is only affected by the current state $S_t$. Therefore, given the visible emissions, the goal is to find the underlying hidden state of each of the emissions. Mathematically, for each given sequence of emissions $O=\{o_1, o_2, \ldots o_t\}$, the sequence of hidden states S is determined which maximizes the probability of the hidden states given the observations. Attempts to train an HMM from raw data did not succeed, scikit-learn was used (scikit-learn.org) as an open source general-purpose machine learning library for Python, and using the Gaussian HMM.

The Viterbi algorithm was applied to determine the sequence of hidden states S contained in S which makes the visible states O most probable, resulting in a set of Viterbi paths $Q=\{q_1, q_2, \ldots, q_t\}$ which maximize the likelihood of $P(E|\lambda)$.

The method was tested on upper limb data (Bergmann et al., 2015). The hardware configuration used, as described in (Bergmann et al., 2015) allowed for upper limb motion patterns to be obtained by an IMU sensor attached to the wrist. The Euclidian norm of the acceleration signal was used as main feature, as accelerations can be applied to differentiate between different motions (Spulber et al., 2012) The norm was determined by $$\|a\| = \sqrt{a_x^2 + a_y^2 + a_z^2},$$

with a as the 3D acceleration vector $[a_x\ a_y\ a_z]$. The norm was computed for each index point and the signal was subsequently segmented in 1-second windows.

It has already been shown that smooth eye movements require cognitive attention during selective tracking tasks (Barnes et al., 1978). The smoothness of other selective tasks, as seen in everyday living, might also have a similar cognitive component, which could affect smoothness. The Hurst parameter (H) describes the sharpness of the acceleration signal, with a higher value indicating a smoother motion. Parameter estimation of fractional Brownian motion based on wavelets can be applied in order to approximate H.

The first assumption for the presented task would be that smoothness starts to vary more as cognitive loading is introduced. However, relying more on an automated movement process when an additional cognitive task is introduced might also have the opposite effect. Therefore, the exact change of the signal is likely to be subject dependent. The changes in the parameter are described by obtaining the standard deviation of several 1-second windows. The threshold value ($T_h$) was computed for each subject by taking the average of the standard deviation found for one loaded and one unloaded condition. Data from 10 subjects containing two loaded and two unloaded conditions, which were needed for determining a subject dependent threshold (training set), as well as an additional data set for testing the accuracy of the prediction. The described approach aimed to correctly predict cognitive loading based only upon the estimated variation of H during the movement task. The results show that the model makes a better than chance prediction (Table 1). This particular method provided an accuracy of 65% (Table 1). The test results for the prediction of 10 subjects who performed an everyday living activity, with or without an additional stroop task. Table 1 shows performance outcomes for the different tasks:

| | Loaded condition | Unloaded condition |
|---|---|---|
| Loaded prediction | 9 | 1 |
| Unloaded prediction | 6 | 4 |
| | Sensitivity 60% | Specificity 80% |

The outcomes show that we could predict with a sensitivity of 60% and specificity of 80% if the auditory stroop task was introduced just by looking at an accelerometer on the wrist during a normal everyday task.

The single loaded tasks consisted either of speaking or making a sandwich, while the dual task required both while performing the Stroop task. The results are given in Table 2. No statistically significant differences in reaction time were seen between the three conditions. Table 2 shows performance outcomes for the different tasks:

| | Speech | Motion | Speech + motion (n = 99) |
|---|---|---|---|
| Missing data (%) | 5 | 6 | 1 |
| Correct responses (%) | 88 | 94 | 77 |
| Reaction time(s) Mean± | 2.15 ± 0.75 | 1.80 ± 0.47 | 2.11 ± 1.53 |

While the complexity of systems that are not inherently linear lends itself to difficulty in expressing the physical phenomena within itself to those structures, I propose the methodology of the Brain Code, a representation scheme designed initially to enhance our study of human brain disorders, mainly the early detection of neurodegenerative diseases. The properties of codes and their fitness for a specific application, in this case the biological solution of the human brain, requires an accurate but also relevant and energy efficient description. Applying machine learning as placeholder in order to identify relevant features and subsequently introducing unitary math as a proper interface between in- and output provides the base for the brain code. The Brain Code offers a theoretical framework that bridges the gap between cognitive outputs—the mind—and the biological, chemical, and physical source of those processes—the brain. The "Brain Code" framework is a large task to accomplish; it is attractive for an open source scale approach. Thus BC is argued as a design principle that leads to a framework. As the initial task requires the construction of a wavelet function or set of wavelets for each modality possibly one mother wavelet for a combined modality should also be tested. Because wavelets can describe audio/speech/movement and brain activity in same domains, this also allows all modalities to be described in the "same" way. After testing a mother wavelet, links to resonance and energy input and output should be investigated.

Neural Algorithms

Neural algorithms that form the basis of inference and recognition in the brain are a potential basis for creating new types of machine learning algorithms that potentially meet human-like performance characteristics better than today's leading systems, like the model for parallel processing in neural systems and computers (Eckmiller et al., 1990). The Brain Code suggests that within a given cortical region or cognitive/sensory domain, the brain employs hierarchical algorithms composed of repeated instances of a limited set of computing "primitives" or modular constructs.

These primitives are further theorized to be embodied in cortical microcircuits at various scales, as part of the evolutionary method of solving this biological solution through nature. Although there has been significant progress in understanding multiple aspects of cortical microcircuits and the larger networks in which they are embedded, a comprehensive description of their structure, function, and interconnectivity remains elusive. Consequently, a myriad of mathematical, computational, conceptual, and schematic models have been proposed to describe the nature of the cortical computing primitives and the hierarchical algorithms that employ mathematical, computational, or otherwise executable models of cortical computing supported by neuroanatomy.

Most models are purely conceptual, schematic, or descriptive, for example a framework that simultaneously acquires and analyzes multiple cognitive and behavioral data streams. Specifically, those presenting analytical models to combine neural models and cognitive models, as well as offer a means to infer relationships that might exist between the biological and physical properties of the brain and higher-level cognitive processes (Turner et al., 2013).

Very little is known about the underlying processes that drive cognition. Thus, an effective model of cognition, which can be used to both interpret and interact with cognition in-vivo, must be able to link each natural process involved in cognition, from behavior to language to individual neural activations, in a coherent manner. Such a joint modeling framework would account for the necessity of a unified "timeline" through which meaningful experimental analysis can be performed. This information may be used to formulate a new program aimed at developing novel machine learning algorithms based on high fidelity representations of cortical microcircuits (Howard, 2013h).

CONCLUSION

The theoretical tenets described in this section, predictive linguistics, axiology, the Brain Code, and the Fundamental Code Unit, provide the philosophical rationale for the BCCS. These concepts are essential in order to analyze multi-level data streams as the BCCS proposes to do in order to meet the heterogeneity of PSD phenotypes. These multi-level data streams will be referred to as Targets of Dimensional Measure (ToDM). Each ToDM represents a group of data streams, which represent brain output, that are of particular interest. The next section will describe ToDM of interest the BCCS can use to detect PSD. Keeping in mind the theoretical foundational concepts of the brain code, described in this section, we will proceed to discuss how to take these conceptual ideas and translate these into an approach for the diagnosis and detection of PSD.

Section Three: Approach

Behavioral biomarkers are a broad category of measures that clinicians and researchers can use to detect diseases and disorders. The interaction of multiple elements in a complex biological system requires the measurement of a minimum subset of the elements. The selection of elements to describe behavioral biomarkers comes from the logical reasoning that behavior perceived by humans relies mainly on interpretation of movement and posture (motor system) as well as speech and language (cognition). Therefore, these two systems form an important set of measures of interest in terms of behavioral biomarkers. It is known that movement and language are the product of neural networks and their interactions (i.e. brain function), therefore the BCCS approach is essentially measuring internal brain activity from behavioral output.

PSD presents a broad range of symptoms and conditions that are not fully understood and not yet clinically differentiable. The complex comorbid nature of PSD should therefore take into account a holistic approach. The BCCS approach aims to improve upon today's current methods of clinical diagnosis by combining data collection and computational analysis methods that focus first on the most basic mechanisms of function and dysfunction working towards a system-level understanding. The approach of the BCCS seeks to better understand the pathogenesis of phenotypes of traumatic stress responses by focusing on the mechanisms of psychopathology that evolve over time.

Overall Study Design

For PTSD, the BCCS will include data streams that take into account the natural heterogeneity of trauma response. We will call these multi-level data streams Target of Dimensional Measure (ToDM). Each ToDM represents a group of data streams, which represent brain output, that are of particular interest.

Target of Dimensional Measure: Speech & Language

The Mood State Indicator Algorithm (MSI) and the Language/Axiology Input and Output algorithm (LXIO) make up the speech and language analysis component of the BCCS, which will be described in more detail in Section 4. This component of the BCCS presents a method for quantifying cognitive states from speech or written text by linking axiological values and behavioral trends within a given time frame (Howard, 2012h; Howard, 2013a; Roberts and Kassel, 1996). Collecting spontaneous speech in naturalistic environments (at home, at work, not in a clinical setting) may allow analysis of both speech production and linguistic features to potentially measure motor and cognitive changes, given that speech is produced by biologically selected apparatus of the motor system (Goberman, 2005; Goetz et al., 2009; Howard et al., 2013a; Howard et al., 2013v).

Howard (2014) measured features of speech and vocal impairments in Parkinson's, which indicated a direct relationship between speech and motor symptoms, which may also be the case with PSD (Howard, 2014; Howard et al., 2013a; Howard and Stein, 2013; Howard and Stein, 2015; Howard et al., 2013v). To better understand what that relationship is and the trajectory over time additional non-categorical data is required.

Different modes of speaking, such as conversational and mimicked speech, involve different levels of cognitive and motor function. Spontaneous speech requires an internal motor plan, followed by execution and monitoring, whereas mimicked speech provides a template (Bavelier et al., 2006; Cummins et al., 2011; Factor and Weiner, 2002; Goberman, 2005; Neel, 2008; Peelle and Davis, 2012; Polzin and Waibel, 1998; Sapir et al., 2008; Skodda et al., 2011; Van Lancker Sidtis et al., 2010). Van Lancker Sidtis et al. (2010) argue that subcortical functionality has different effects on speech performance in different speaking modes. For example, in Parkinson's patients they found that dysfluencies are most prevalent in conversational speech (with and without deep brain stimulation (DBS) treatment) also harmonics-to-noise ratio (HNR) improves in mimicked speech when treated with DBS. A study of speech features amongst mild and moderate Parkinson's Disease patients (such as number of silent hesitations per minute, number of filled hesitations per minute, abnormally long silent hesitations, words per silent hesitation, open class phrases, as well as syntactic complexity) separated moderate from mild Parkinson's patients with a high level of accuracy (Goberman, 2005; Howard et al., 2013v; Rapcan et al., 2009; Skodda et al., 2011; Thomas et al., 2005; Tsanas et al., 2010; Tsanas et al., 2011; Van Lancker Sidtis et al., 2010). Specific language features such as metaphors may provide further information about their cognitive state. Although very little is known about this neural phenomenon, we know that metaphors associated with specific concept types (i.e., predicate metaphors) involve increasingly abstract processing along the lateral temporal cortex and can be analyzed accordingly (Chen et al., 2008).

Examples of PTSD Language Analysis

Papangelis et al. (2013) introduce an adaptive dialogue system (ADS) for assessment of patients with PTSD. Their system was focused on training new clinicians to perform PTSD assessment themselves, this natural language system is designed to replace the human clinician in order to extract sufficient information to make a diagnosis. The authors' research focuses on the information-seeking paradigm, in which the system performing the assessment is continually able to modify its diagnosis based on new input from the patient. This system employs a slot-based structure, in which each "slot" or piece of information can be set to boolean, integer, or string values such as "yes/no," "1," or "lethargic." The slots are related to one another based on temporal proximity, as well as their relationship to the question posed by the automated adaptive dialogue system. The current dialogue state is defined as a vector (d∈D). This vector contains all information used to describe the interaction to the present point, such the information provided and information still missing. They also define dialogue "state transition probabilities," which are continually updated, in order to account for uncertainty in understanding the patient, assigning confidence values to each slot, and then analyzing the results with a hierarchical Markov Decision Process. Using a matrix-based structure of slot values and a parallel matrix of confidence values, the ADS continually assesses the patient's emotional state, and actively balances between keeping him/her calm when possible and retrieving the information it needs, which sometimes triggers reactions to traumatic events. In order to assess emotions presented by the patient, the authors relied on a dictionary-based emotion-recognition method whose keywords predominantly correspond to single emotional states. While the ADS described by the authors is able guide conversations in a way that it elicits information in a similar way as PTSD self-assessment tests, it still lacks the ability to incorporate visual input and other audiovisual features, such as pitch, tone and facial expressions which are important for the most comprehensive PTSD diagnosis.

DeVault et al. (2013) identify several dialogue level features that distinguish between patients with depression and those with PTSD, as well as between PTSD patients and healthy controls. Like Papangelis et al., the DeVault et al. present a virtual dialogue system that extracts features from patients' speech and use the information as a way to sort and triage patients to be evaluated more precisely by human clinicians. Their approach is reflective to the state of automated diagnosis technology; that is, it is little more than an adjunct to current therapeutic methods. However, DeVault et al. do incorporate additional factors into their assessment, such as increased speaker-switch durations and decreased variability of vocal fundamental frequency, which have been shown as indicators of depressive mind states by Cohn et al. (2009). In order to show the feasibility of the virtual assistant, the authors hired participants to complete a series of questionnaires such as PTSD Checklist-Civilian version (PCL-C) and the Patient Health Questionnaire, depression module (PHQ-9), then engaged them in an interview with the virtual clinician "Ellie." This system used a similar slot-based structure as Papangelis et al. to categorize subcomponents of patient dialogues, such as those separated by pauses. For each dialogue di∈D, the system collected data across several context-independent fields in addition to speech content, such as the speaking rate of each user segment, mean length of user segments, mean maximum valence in user segments, and the total number of user segments. Using these features, the authors were able to achieve a diagnostic accuracy of 74.4% for PTSD. Approaches such as Kenny et al. and IBM's Watson Watkins et al. (2012) rely on the automation or expedition of existing diagnostic procedures using natural language processing. However, the true value of Natural Language Processing (NLP) in diagnosing PTSD is its near-limitless potential for drawing upon high-quality data (in that data availability is only limited by access to patients), as well as its ability to provide deeper than face-value analysis of human speech and its noninvasiveness.

Target of Dimensional Measure: Movement

Movement is of particular interest because, like speech and language, it is a major component of human behavior. Movement data from PSD patients may be able to give new insight into how the motor system is effected by disease and how it differs from other patient groups. There is evidence that motor control, such as balance, gait, and stability, can be impaired by psychological disorders (Alexander et al., 1995; Allah et al., 2010; Bridenbaugh et al., 2012; Michalak et al., 2009; Mielke et al., 2013; Moore et al., 2007; Moscovich et al., 2013; Niazmand et al., 2011; Woollacott and Shumway-Cook, 2002). Although much less focus is given to movement impairments compared to the emotional and cognitive symptoms of psychological disorders, several movement impairments have been observed such as gait, abnormal posture, pure dystonia, facial spasm, tremor, and "hyperthyroidism-hyperadrenalism" (Carroll et al., 2011; Dethier et al., 2013; Moscovich et al., 2013; Walters and Hening, 1992). Freezing posture has been observed in fear/anxiety disorders and it has been repeatedly shown that depressed patients differ from normal and psychiatric comparison groups with regard to objectively quantified gross motor activity, body movements, and motor reaction time (Moisello et al., 2011; Porter and Coltheart, 2006; Sobin and Sackeim, 1997). Fleisher et al. (2002) studied 32 subjects with Epilepsy. Each participant completed the Impact of Event Scale, the Davidson Trauma Scale, the Mississippi Scale for Combat-Related Posttraumatic Stress Disorder (PTSD), the Dissociative Experience Scale, and Pittsburgh Sleep Quality Index measures. Subjects with Epilepsy exhibited trauma-related profiles that differed significantly from those of epileptic comparison subjects and closely resembled those of individuals with a history of traumatic experiences (Fleisher et al., 2002).

In previous research we have successfully used Body Sensor Networks (BSN) to objectively collect movement data, especially during the performance of everyday tasks involving physical movements (Aziz et al., 2007; Bergmann and Howard, 2012; Bergmann et al., 2012; Bergmann et al., 2014; Chan et al., 2007; Espina et al., 2006; Howard and Bergmann, 2012; Lo et al., 2005; Lorussi et al., 2004; Loseu et al., 2012; Quwaider and Biswas, 2008; Seto et al., 2009; Webb et al., 2013). BSN are an effective collection method for broad categories of activity, such as standing, that can be used to assess the motor system Monitoring the functional movements of both the upper and lower limbs offers the chance to collect a real-life parameter, which can be coupled with subjects' cognitive and emotional data from other measures of output.

Facial Features

Several fields of research show that facial expressions can be useful in detecting emotional and cognitive states (Bowers et al., 2006; Cohn et al., 2009; Dethier et al., 2013; Ekman, 1993; Ekman and Rosenberg, 1997; El Kaliouby and Robinson, 2005; Huggins et al., 2011; Jacobs et al., 1995; Katsikitis and Pilowsky, 1988; Keltner et al., 2003; Kulkami et al., 2009; Liu et al., 1999; Lyons et al., 1998; Pantic and Rothkrantz, 2000). Emotions expressed through facial movements play a crucial role in our daily lives. Facial expressions, both spontaneous and voluntary, communicate our feelings to others. Emotional problems, such as depression and anxiety, are common comorbidities of PSD (Cloitre et al., 2014; Cohen et al., 2011; Spinhoven et al., 2014) and are measurable through facial expression analysis. Facial expressions may also be affected by emotional impairments given the role of the basal ganglia in emotional processing.

CONCLUSION

The BCCS approach proposes to collect objective and subjective measurements to compare and correlate novel objective behavioral markers to the current PSD clinical standards of subjective self-reporting. Hence, our approach does not rely on retrospective recall of symptoms or abbreviated or self-reported measurements of PTSD symptoms. The next section will describe specific BCCS methods and why they are the preferred methods to use for the BCCS.

Section Four: Methods

The methods we describe in this section have primarily been used in the data mining community for military and intelligence applications (Cambria et al., 2013; Cambria et al., 2012; Howard, 2001a; Howard, 2001c; Howard, 2002; Howard, 2007; Howard, 2011a; Howard, 2011c; Howard, 2012b; Howard, 2012h; Howard, 2013b; Howard, 2013e; Howard, 2013h; Howard and Argamon, 2009; Howard et al., 2009; Howard and Cambria, 2013a; Howard and Guidere, 2011; Howard and Leisman, 2013; Howard and Lieberman, 2012). These methods have evolved from being used in command and control and data mining technologies to being used for research and clinical applications.

Machine learning is a rapidly growing field and is more frequently being explored as a method for clinical applications, including diagnosis of Alzheimer's disease and Autism (Bosl et al., 2011; Datta et al., 1996; Trambaiolli et al., 2011) and also detection and prediction of freezing of gait in PD (Mazilu et al., 2013). In general terms, machine learning is to construct a system that can learn from data inputs (Mazilu et al., 2013). There exists a variety of machine learning models for different applications. Generally speaking, there are two groups of machine learning algorithms: supervised learning and unsupervised learning. In supervised learning, labels of each observation in the dataset (training data, specifically) are known, and the goal is to construct a function to predict the label of a new observation; in unsupervised learning, the labels of the dataset are not known and the goal is to find the hidden structure of the data.

Language Analysis Using Machine Learning

Natural language analysis requires a robust computational method to overcome common NLP challenges. For instance, the use of out of context expressions, whose meaning is derived primarily from context rather than content, presents a significant computational hurdle to develop natural language processing algorithms. Vague and ambiguous modifiers, for instance, are difficult for computers to interpret because their words' meanings are in part defined by conversational structure in addition to their inherent meaning. A method is required that preserves the context of these spoken words by means of temporal structure that incorporates behavioral and contextual information associated with the concepts being discussed. Natural language structures, such as metaphors, are embedded in time domains that depend on cultural, conversational, and cognitive context. However, this important information tends to be neglected in text forms. While this is less of a problem for humans, who are used to reasoning empathetically about the language generation process and considering alternative meanings and decisions.

Syntactic Structure Identification Ddjean (2000) applies background knowledge and default values in order to construct grammars for non-recursive phrases. His proposed system uses theory refinement in order to "automatically modify a knowledge base to render it consistent with a set of classified training examples." The process consists of two steps: (1) the use of external background knowledge (i.e., that provided by the designers) to build a roughly correct grammar, and (2) the use of training examples to find points in the grammar that need to be corrected. Tadapak et al. (2010) focus on content gathering in a language-specific context. Their process is to parse web pages, determine their native language, and gather data from them if they match a specific set of predetermined languages. Gathered data also helps optimize future language-based searches by highlighting web servers that are more likely to host pages written in the target languages. The primary machine language learning algorithm in Tadapak et al.'s approach (2010) is composed of three steps. First, the language predictor is "trained." That is, it is fed typical examples of the target language for rote acquisition of common syntactic constructions. Once the web page in question is downloaded to a server and its text converted to an easily parseable format (UTF8), the following loop is applied:

```
If LexTo returns nonThai nonThai_count+ +
If nonThai_count > defined_Threshold τ
StopThisProcess_and_EXIT Else nonThai_count = 0
If nonVisitedQ not empty
Dequeue a URL from nonVisitedQ Goto 2
```

In order to determine whether there exists a language match, web page data is matched against a lexical database with a minimum of 10% words in common. Tadapak et al. (2010) appear to be more interested in quantifying linguistic tendencies within a certain error percentage than in quantifying the language itself. However, since the algorithm improves with each website it processes by gathering host data and performing linguistic comparison, it has implications for the language learning model. Sagiroglu et al. (2007) also propose a language identification process, but does so with the intent of finding multiple languages embedded in a single source or website. In essence, this process uses letter frequency analysis backed by artificial neural networks (ANNs). ANNs work by "detecting the patterns and relationships among data and learn[ing] through their architectures and learning algorithms" (Sagiroglu et al. (2007).

The Multilayered Perceptron Neural Networks (MLPNNs) used by Sagiroglu et al. (2007) consists of three layers: input, output, and at least one "hidden" layer. This is done in order to add (or subtract) weight to each input signal that matches the pre-trained lexical network. The percentage of input to output neurons thus helps the MLPNN determine whether the input matches with a given language. Constructing the MLPNN occurs by adjusting it for the occurrence frequency of texts available in each target language. The algorithms used by Sagiroglu et al (2007) were Levenberg-Marquardt (LM) and Backpropagation with momentum (BPM). To be brief, LM uses a "least-squares estimation method based on the maximum neighborhood idea" and is classified as a momentum-learning algorithm. BPM is a gradient descent method for calculating network weights that gives the change in the weight of the connection between two neurons at a given connection. Ultimately, this approach is used to train a network with bias rules based on each language's indexicality.

Figure 3:
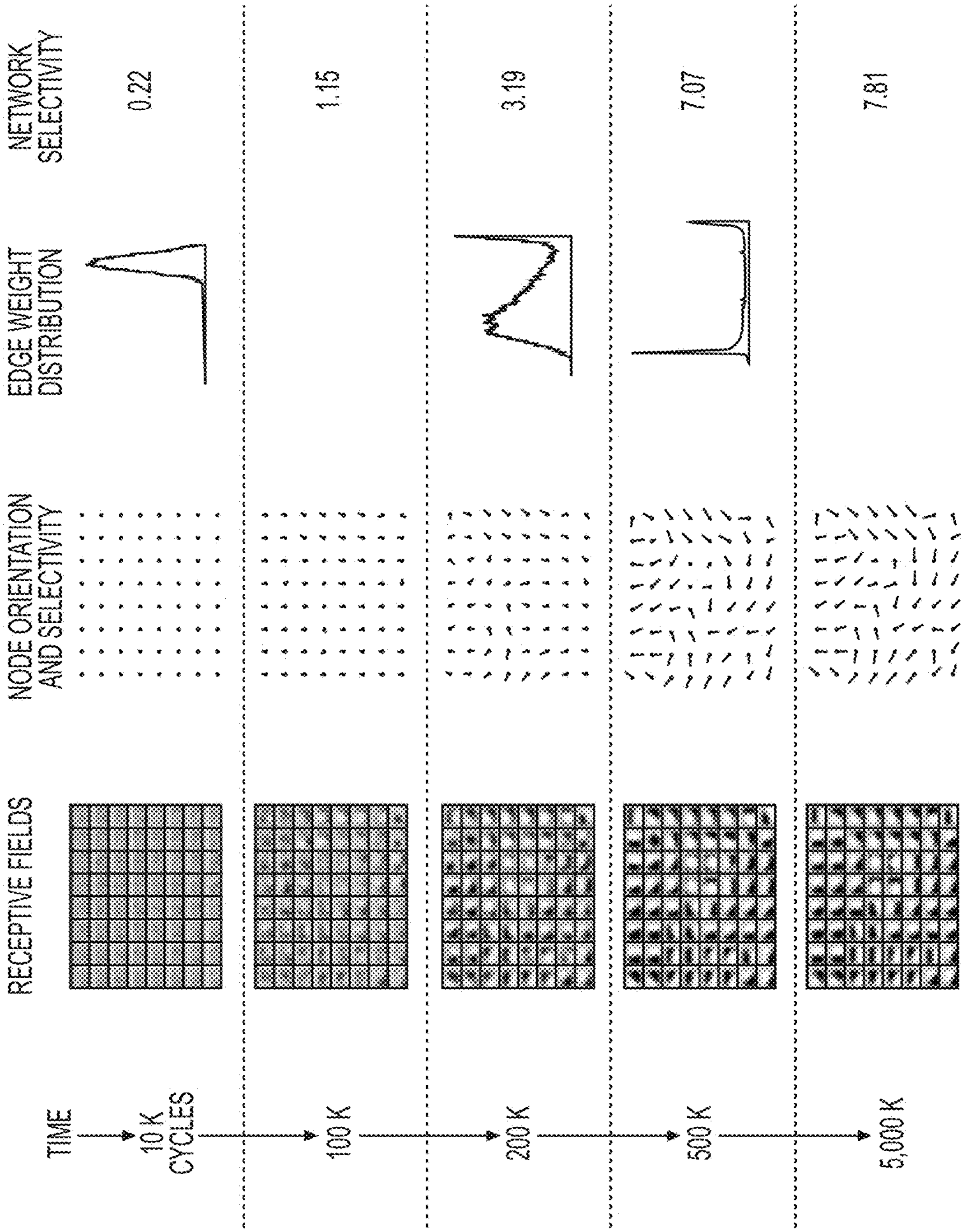
FIG. 3 illustrates selective activation of neural networks over time.

FIG. 3 illustrates selective activation of neural networks over time (Snider 2008).

Machine Translation Algorithms

Valiant (1984) lays out the machine translation problem as "knowledge acquisition in the absence of explicit programming," and a methodology for class exploration and the achievement of language learning. According to Valiant, "learning machines" can acquire new classes of concepts in a polynomial number of steps (i.e., a computationally tenable time complexity). Arnold et al. (1994) lay out several important criteria for the effectiveness of machine translation algorithms, each of which contains the potential for algorithmic variation. First, categorization of words must take place. Given a string of text in a given language, that string must be parsed for matching words using a dictionary that contains relevant contextual data for each of those words to be a data structure, its payload would include the string itself, word type, variations based on tense and gender, and possibly context.

The more data that is contained in the structure's payload, the better the machine will grasp its linguistic significance. For instance, a dictionary data structure for the word go might, in order to be as comprehensive as possible, contain variations such as goes, went, gone, and used to go in order to tie them all to the same general definition of to go, with variation based on context and qualities of the subject. In the worst case, parsing each such word, assuming there are at least two more variations of it in the English language, will increase the execution time of the parsing algorithm, as well as its time complexity if it is equipped to process phrases. Consequently, a particularly useful machine learning algorithm would seek to minimize the overall size of this data payload for the sake of speed, performance, and efficiency while simultaneously maximizing the proportion of this data that is truly useful to the translation process. Such a learning algorithm will most likely be based on statistical data regarding verb tense and noun gender variation, as well as the approximate amount of variation of these variables per amount of text.

The second prerequisite step in machine translation is parsing the sentence using pre-defined grammar rules. Whereas the first step determined word types (and possibly word phrase types, such as prepositional phrases), the use of these grammar rules determines which words compose object, subject, action, and modifier(s). This dual-layered parsing requires two passes (at least) over the data—algorithmic improvement in this field might buffer commonly encountered phrases, words and their contexts—this would improve time complexity at the expense of space complexity, but the latter is cheaper—whereas no amount of hardware tinkering (at least on the horizon) can fundamentally alter the effects of theoretically high time complexity, the quick pace at which the cost of memory decreases and the sophistication of hardware increases suggests that algorithms that are spatially complex but temporally efficient will have greater long-term relevance.

Third, transformation rules must be applied in order for the translation process to proceed. Transformation rules include patterns for determining the structural differences between equivalent sentences in different languages. For instance, determining the distinction between the 2nd person present tense ("you go to the store") and the imperative tense ("go to the store") may require more than simply mapping words in one language to their equivalent in another language. Machine learning algorithms can be applied here in seeking the most common transformation rules based on frequent associations. For instance, if the phrase "go to the store" is preceded by a "please" or followed by a temporal directive ("tomorrow," "now," "before . . . [you come home]"), then it is more easily identified as an imperative.

The nuances and complexity of human language dictate that machine learning must occur as evolutionary training. The more raw input such a machine receives and analyzes, the more effective it becomes. Thus, algorithms that seek to improve the efficiency or the effectiveness of machine language learning should focus as much as possible on the optimal configuration of training data, and the best way to do this is to approach it from the language statistics point of view. The learning process itself is a straightforward progression of a small number of highly important steps; thus, the greatest capacity for improvement is in the data we feed into this process.

Madsen (2009) argues that high-quality machine language translation is simply not a feasible goal, and that a better computational objective is to frame the problem in a way that is more helpful to human analysts, who will always be a necessity in language translation. That is, an explicit definition of what machine translation can and cannot do will allow humans to devote their attention more efficiently in the translation process. Madsen discusses three specific approaches to machine translation, and the weaknesses inherent in each: the dictionary method, knowledge-based methods, and statistical methods. The dictionary method is the simple and straightforward process of translating each input word, one at a time, by matching against a database of linguistic equivalents. Since this method does little to account for context and differences in phrasing. A revision of this approach, the Georgetown-IBM method, works by translating word triplets to increase the probability of correctly accounting for phrases. Although the method used by the Georgetown-IBM supercomputer is still prone to contextual errors, triplet-based translation is as accurate (in the worst case) or more so than the original dictionary method, at the expense of greater time complexity. The Georgetown-IBM method works in two parts. The first is a lexical step that splits source text in to morphemes, or the smallest grammatically meaningful units in the language. The morpheme dictionary contains several possible meanings of each morpheme, which is used to assign markups to each morpheme. In the second, or "operational" step of the Georgetown-IBM algorithm, the morphemes are examined while keeping in a memory buffer the previous and next ones. This allows subsequent operations to correctly place modifiers, subject and objects when switching between languages (i.e., in front of a noun instead of following it).

One of Georgetown-IBM's primary weaknesses is its inability to distinguish between idioms. As Madsen (2009) puts it:

No distinction is made between He let down his guard and He let down his friends, or between He had blood on his hands after the trial and He had blood on his hands after the operation.

Knowledge-based machine language learning methods involve the incorporation of semantic information into the translation (i.e., associations between chairs and sitting, cars and driving, beverages and [drinking, liquid, thirst]). Empirical knowledge is also a fundamental component of knowledge-based translation, like the association between violence and fear. The association is linguistically indirect but observably direct. The Meehan algorithm, developed at Yale University (Meehan, 1977) is a particularly clear example of knowledge-based machine language learning. Instead of constructing language from the morpheme up, Meehan used concepts like actors, desires, and actions to build narratives from scratch. One example program was called TALE-SPIN, and was designed to generate stories in the same style as Aesop's fables (Meehan, 1977); these were often flawed, but similar techniques were used in the translation of subject matter with predictable context (i.e., weather forecasts). Ultimately, the main obstacle to knowledge-based translation is the fact that enough quantifiable information cannot be stored. To "teach" a machine bits and pieces of knowledge, and the associations between those bits and pieces, in a retroactive manner by pre-programming what we already know about the world thus proved to be an inefficient means of machine learning. Human language learning, in a very simplistic sense, consists of two components: the experience needed to form conceptual associations, and the analytical means to process them as new situations arise. Humans, for the most part, are not equipped with prior knowledge associations. However, they do have the cognitive means to form new associations and incorporate them efficiently. Consequently, to attempt to pre-program machine learning schemes may be successful in some respects, but will never out-"associate" a human brain due to the tremendous amount of information that must be stored before analysis can even begin. Madsen (2009) disagrees and criticizes this aspect of machine learning arguing that there is no way to create a facsimile of human learning in the machine realm only ways to re-construct it from the ground up.

Goguen (2006) begins analysis of spatiotemporal metaphors by asking when the statement "The Wednesday meeting was moved forward two days" has just two solutions (as days of the week). He begins by identifying three distinct dualities in our concept of space and time: ego (self) reference point vs. absolute reference point, static vs. dynamic, and landmark reference points versus trajector (moving) reference points.

Goguen constructs the following formalization of the problem:

Time = Z
Su, M, Tu, W, Th, F, Sa: → Day
Day: Time → Day
E, T: → RP
$f_2$: Time Time RP → Time

| | | |
|---|---|---|
| day(0) = Su | day(1) = M | day(2) = Tu |
| day(3) = W | day(4) = Th | day(5) = F |
| day(6) = Sa | | |

$(\forall t, t' : \text{Time})\ \text{day}(t) = \text{day}(t') \text{ if } |t - t'| = 0 \bmod 7$
$(\forall t, t' : \text{Time})\ f_2(t, t', E) = t - 2 \text{ if } t \leq t'$ -continued $(\forall t, t' : \text{Time})\ f_2(t, t', E) = t + 2 \text{ if } t > t'$
$(\forall t, t' : \text{Time})\ f_2(t, t', T) = t + 2$ If we assume that Time includes all integers (0 being present, negative being past, and positive being future), then the day of the week needs to then be declared, followed by a function that maps Time to days. Goguen's objective was to prove that only two possible solutions existed for the problem, where m'=1 or m'=5, depending on what "moved forward" means.

Goguen (2006)'s solution set contains the following similar theories:

| | |
|---|---|
| m, m', e: → Time | m, m', e: → Time |
| r: → RP | r: → RP |
| $f_2$(m, e, r) = m' | $f_2$(m, e, r) = m' |
| m = 3 | m' = 3 |

Here, concepts map m', the new meeting time, to either Wednesday or two days after Wednesday, due to ambiguity in the sentence. This provides a rational framework to which idiomatic data and information can be applied, such as the regional tendencies of this sentence to have divergent meanings. If we apply this framework to parametric event portioning, as explored in (Malouf, 2002), we may be able to construct a uniform cognitive mechanism for translating spoken words into FCU-based information, regardless of linguistic difference or regional dialect. (Chater and Manning, 2006; Chater et al., 2006) capitalize on recent progress in computational science that enables robust probabilistic models to be used to analyze relational systems such as graphs, grammars, and other mappings. Chater et al. (2006) take the complex problem of cognition and structure it as yet another in a series of computational challenges involving "relational systems," meaning that at its core, cognition is simply a network of nodes and connections, down to the individual neural connection and intemeuron signal. The authors point out that cognition is, in essence, an exercise in information processing, and that "information processing typically involves inferring new information from information that has been derived from the senses, from linguistic input, or from memory" (Chater and Manning, 2006; Chater et al., 2006). To that end, cognitive modeling should employ similar methods of information assimilation and recall to approach the behavior of the brain in its natural state. The probabilistic perspective is advantageous because it is conducive to the development of techniques that blend multiple sensory sources and account for the uncertainty inherent in each.

Case-Based Reasoning

Case-based reasoning differentiates itself from other means of machine learning that rely on generalized relationship rules because it is "able to utilize the specific knowledge of previously experienced, concrete problem situations (cases). A new problem is solved by finding a similar past case, and reusing it in the new problem situation." Unlike the methods used by Arnold et al. (1994) case-based reasoning focuses on the application of input data rather than its formatting or the means by which it is acquired.

There are five primary means of performing case-based reasoning: Exemplar-based, instance-based, memory-based, case-based, and analogy-based. Exemplar-based reasoning refers to the extensional definition of cases. In the machine learning case, this means the definition of types of words and phrases by their typical context. For instance, typical proper nouns that don't occur at the beginning of a sentence are still capitalized—this feature allows exemplar isolation, and for a better idea of the typical context of such objects. In order to algorithmically optimize exemplar-based reasoning, it is more important to select the most unique and/or relevant aspects of exemplars than it is to focus on the initial (predetermined) definition itself. This allows better exemplar retrieval and a better sampling of different contexts in which various word types are used. Instance-based reasoning is a specialized form of exemplarity, and is less knowledge intensive by design—it compensates for a lack of background knowledge in a given case. Memory-based learning begins with the collection of large numbers of cases in order to develop patterns of precedent. It can deal either with syntactic criteria or general domain knowledge. In the first case, the placement of specific word types (and conjugations) is the primary data source; in the latter, correct, and incorrect usage examples may be drawn from the memory of cases for analytical purposes. If we want to optimize memory-based learning techniques, the best way to do so is the selection of optimal cases for the memory buildup. This is similar in some sense to the choosing of particular advantageous test cases discussed earlier. From an algorithmic perspective, this means using exemplarity to parse ideal phrases and word contexts, and moving those into a database. (Typical) case-based reasoning presupposes a generally higher degree of information richness and organizational sophistication: "[typical case-based methods] are able to modify, or adapt, a retrieved solution when applied in a different problem solving context." (Aamodt and Plaza, 1994).

Case-based reasoning differentiates itself from other means of machine learning that rely on generalized relationship rules because it is "able to utilize the specific knowledge of previously experienced, concrete problem situations (cases). A new problem is solved by finding a similar past case, and reusing it in the new problem situation." Unlike the methods outlined previously in Machine Translation Methods, case-based reasoning focuses on the application of input data rather than its formatting or the means by which it is acquired.

There are five primary means of performing case-based reasoning:

Exemplar-based
Instance-based
Memory-based
Case-based
Analogy-based

Exemplar-based reasoning refers to the extensional definition of cases; in the machine learning case, this means the definition of types of words and phrases by their typical context. For instance, typical proper nouns that don't occur at the beginning of a sentence are still capitalized—this feature allows exemplar isolation, and for a better idea of the typical context of such objects. In order to algorithmically optimize exemplar-based reasoning, it is more important to select the most unique and/or relevant aspects of exemplars than it is to focus on the initial (predetermined) definition itself. This allows better exemplar retrieval and a better sampling of different contexts in which various word types are used. Instance-based reasoning is a specialized form of exemplarity, and is less knowledge intensive by design—it compensates for a lack of background knowledge in a given case.

Memory-based learning begins with the collection of large numbers of cases in order to develop patterns of precedent. It can deal either with syntactic criteria or general domain knowledge. In the first case, the placement of specific word types (and conjugations) is the primary data source; in the latter, correct, and incorrect usage examples may be drawn from the memory of cases for analytical purposes. If we want to optimize memory-based learning techniques, the best way to do so is the selection of optimal cases for the memory buildup. This is similar in some sense to the choosing of particular advantageous test cases discussed earlier. From an algorithmic perspective, this means using exemplarity to parse ideal phrases and word contexts, and moving those into a database. (Typical) case-based reasoning presupposes a generally higher degree of information richness and organizational sophistication: "[typical case-based methods] are able to modify, or adapt, a retrieved solution when applied in a different problem solving context."

Analogy-Based Reasoning

Finally, there is analogy-based reasoning, which is designed for the solution of new problems using past cases from diverse domains. Cross-domain analogical reasoning requires matching patterns to patterns instead of patterns to predefined dictionary entries. Thus, the algorithmic problem is doubly complex, and potential approaches must be two-fold in nature: first, they must choose best cases from the selected domains. In the language learning sphere, this means a roughly accurate proportion of the occurrences of proper uses of a given rule and accepted exceptions to that rule. One that comes to mind is the addition of "ed" for past tense verbs or "s" for plural nouns. Exceptions exist, and the only way to "teach" a machine that that is the case is to seed the selected language domains with sufficient exceptional cases. Parsing of each language's domain prior to language learning processes is the most likely course of action in analogy-based reasoning.

Speech-Based Cognitive Assessment

A modular analysis engine for speech content that enables clinicians and researchers to better understand a patient or subject's state of mind based on their linguistic output is needed. Their system offers a new means of "examining [a subject's] selection of words, their value, and the instances of which they used them in will paint a clear picture of their current state of mind." The correlation of computational data can allow for better psychological assessment.

To provide a rigorous assessment of mind state, Howard & Giudere (2011) base their core analysis on a database of default values. Because our thoughts and perceptions are directly represented by words, these default values link concepts to specific mind states, known as the Mind Default Axiology (MDA). MDA values can be altered based on context and vocal cues, but are inherently anchored by their content. A person's choice of words holds value and meaning which can give a clear picture of a patient's state of mind. This state of mind if based on an axiological analysis of elements such as perception intention and conception. By assigning positive and negative values with concepts it can provide more insight about cognitive state. This system can decipher the human state of mind by examining the selection of words and how they are used. Word strings including individual words, phrases, and entire sentences are assigned values based on MDA as well as dictionary values using the following pseudocode function:

```
set axiology_value (set mda, set dictionary) {
int i;
for (i=0;
```

-continued

```
i <= sentence_length;
i++) {
axiology_value = mda ^ dictionary;
}
return axiology_value;
}
```

We use the following function to identify instances of matching word patterns:

```
Int findmatch (char *p, char *t){
int i, j; int m, n; m = strlen(p); n= strlen(t);
for (i=0; i<=(n−m); i=i+1) {
j=0;
while ((j<m) && (t[i+j]==p[j])) j=j+1;
if (j==m) return (i);
}
return (−1);
}
Syntactic Structure Identification
```

Tadapak et al. (2010) focuses on content gathering in a language-specific context. That is, the task of this proposed process is to parse web pages, determine their native language, and gather data from them if they match a specific set of predetermined languages. Data gathered here also help to optimize future language-based searches by highlighting web servers that are more likely to host pages written in the target languages. Their site crawler is the primary machine-learning centric appliance in the process. The primary machine language learning algorithm in Tadapak et al.'s approach is composed of three steps. First, the language predictor is "trained." That is, it is fed typical examples of the target language for rote acquisition of common syntactic constructions. Once the web page in question is downloaded to a server and its text converted to an easily parseable format (UTF8), the following loop is applied:

```
If LexTo returns nonThai nonThai_count+ +
If nonThai_count > defined_Threshold τ
StopThisProcess_and_EXIT Else nonThai_count = 0
If nonVisitedQ not empty
Dequeue a URL from nonVisitedQ Goto 2
```

In order to determine whether there exists a language match, web page data is matched against a lexical database with a minimum of 10% words in common. Tadapak et al. appear to be more interested in quantifying linguistic tendencies within a certain error percentage than in quantifying the language itself. However, since the algorithm improves with each website it processes by gathering host data and performing linguistic comparison, it has implications for the language learning model.

Sagiroglu et al. (2007) also proposes a language identification process, but does so with the intent of finding multiple languages embedded in a single source or website. In essence, this process uses letter frequency analysis backed by artificial neural networks (ANNs). ANNs work by "detecting the patterns and relationships among data and learn[ing] through their architectures and learning algorithms." The Multilayered perceptron neural networks (MLPNNs) used by Sagiroglu et al. consist of three layers: input, output, and at least one "hidden" layer. This is done in order to add (or subtract) weight to each input signal that matches the pre-trained lexical network. The percentage of input to output neurons thus helps the MLPNN determine whether the input matches with a given language. Constructing the MLPNN occurs by adjusting it for the occurrence frequency of texts available in each target language. The algorithms used here were Levenberg-Marquardt (LM) and Backpropagation with momentum (BPM). Levenberg-Marquardt uses a "least-squares estimation method based on the maximum neighborhood idea" and is classified as a momentum-learning algorithm. It calculates network weights based on a damping parameter (λ) and Jacobian (JsK) & identity Matrices (I):

$$\left(J_k^T J_k + \text{lambda } I\right)\text{delta omega}_k = -J_k^T f(\text{omega}_k)$$

Backpropagation with momentum is a gradient descent method for calculating network weights that gives the change in the weight of the connection between two neurons at a given connection by $$\Delta\omega_{ji}(k) = -\alpha\frac{\partial E}{\partial\omega_{ji}(k)} + \mu\Delta\omega_{ji}(k-1) \tag{1}$$

where α is called the learning coefficient, μ the momentum coefficient and $\Delta\omega_{\mu}(k-1)$ the weight change in the immediately preceding iteration.

Ultimately, this approach is used to train a network with bias rules based on each language's indexicality.

Parallel-Independent Approach Vs. The Sequential Approach

Bates (1995) argues that "[c]ritical areas for the future include grammar that is appropriate to processing large amounts of real language; automatic (or at least semi-automatic) methods for deriving models of syntax, semantics, and pragmatics; self-adapting systems; and integration with speech processing." What this means for the study of natural language, and its specific applications, is that dictionary-based natural language mechanisms may be adequate for some tasks, but will likely never parallel the human brain due to the sheer time, in addition to pre-programming, that is needed for it to function properly (that is, produce some amount of correct output). Bates frames the Natural Language Processing (NLP) discourse as two-fold in nature. The first approach is sequential; that is, it views the problem of language translation and learning as a set of interdependent problems that must be solved in a specific order. Another view is that NLP consists of independent, parallel processes, each using a different knowledge base that contributes unique knowledge to the problem. The parallel-independent approach to NLP uses a dictionary-equipped lexical processor that organizes input words into useful syntactical structures (i.e., prepositional phrases). Another module, the syntactic processor, uses a grammar of the language in question in order to process idiomatic language and context.

The discourse and pragmatics module is of particular interest; in addition to using input phrases to construct proper sentence forms, it contains a task model specific to the user's goals. It also keeps track of the portions of those goals that have been achieved by previous inputs. For instance, similar tasks may recur in slightly different forms over the course of a translation task, such as translating the same phrase into multiple languages, or creating a list of similar terms and their definitions (a dictionary in the conventional sense).

MSI & LXIO

To clinically use language and speech for the detection of PSD, the BCCS uses the Mood State Indicator (MSI) algorithm developed by Howard (2011; 2012). The MSI algorithm uses natural language from speech or text to measure and detect cognitive "mind states" based on axiological values. The analytical algorithm systematically retrieves, parses, and processes written/spoken discourse into individual words to which positive and negative values are assigned. These values are then correlated to values calculated by psychological assessment testing to better diagnose an individual's mood state. Other mood detection algorithms, such as lexical analysis of spontaneous speech (Thomas et al., 2005), are based on grammar and semantic analysis, but the disadvantage with these algorithms is that "environmental noise" distorts incoming data. For example, noise in the military environment includes, weather, slurs, other people talking in the background. The MSI algorithm, however, is more efficient as it is a value system indicator, meaning regardless of noise and quality of recording the algorithm can extract meaningful analyses of mood states. The MSI is also unique because it takes into account the past, present and future tense of words in order to capture time projection. In addition to linguistic analysis the MSI system can take into account variations in speech production such as shimmer, jitter, and amplitude, which are more so a measure of motor control than language analysis. Vocal patterns reflect the complex interaction of muscles in the vocal tract, as well as the level of motor precision needed to produce intelligible speech.

The core engine of MSI is the Linguistic-Axiological Input/Output (LXIO), which provides parameters for a speech-based axiological analysis. LXIO assigns positive and negative values to specific concepts and words based on their intrinsic connotations as well as context.

Axiology-based values can be determined based on an individual's word usage and sentence construction. Values (+ or −) are assigned to every word, tense, and concept of the linguistic data.

Mind Default Axiology Database

The Mind Default Axiology (MDA) database stores common word values. The database was built by Howard & Guidere (2011) using a large cohort of subjects at the University of Geneva and systematically chosen open source datasets. Spoken or written excerpts were collected from every subject at least once over a measured period of time. The linguistic data was axiologically sorted so that each sample had multiple word-value frequencies depending on usage and time. These words were parsed and stored in a large database sorted by intrinsic axiological value. The MSI system was initially calibrated using this database. Axiological value defines truth, or axiom, within our mathematical framework. Value is thus a starting point within a logical system that can be chosen at random. However, the relevance of the axiomatic calculation depends on the relevance of its values and their interpretation.

Axiological values are the basis of formal cognitive processes. Here is a simple calculation which follows an internal composition rule (+). Table 3 shows an example of calculating axiological values

| | |
|---|---|
| 1 + 2 = 1 + succ(1) | Abbreviation extension (2 = succ(1)) |
| 1 + 2 = succ(1) + 1 | Axiom |
| 1 + 2 = 2 + 1 | Abbreviation extension (2 = succ(1)) |

-continued

| | |
|---|---|
| 1 + 2 = 2 + succ(0) | Abbreviation extension (1 = succ(0)) |
| 1 + 2 = 2 + 1 = succ(2) + 0 = 0 + succ(2) | Axiom |
| 1 + 2 = 3 = 0 + 3 | Use of the abbreviation (succ(2) = 3) |
| 0 + 1 = 1 + 0 = 1 | Axiom |
| X + succ(X) = succ(X) + X | Axiom |

Procedures and Metrics

Much contemporary work in psychometrics, which concerns itself with the construction and validation of the instruments with which we measure psychological metrics, has been undertaken in an attempt to measure personality, attitudes, and beliefs. Measurement of these phenomena is difficult and largely subjective, and much of the research and accumulated science in this discipline has been developed in an attempt to properly define and quantify such phenomena. The MSI model is particularly novel in that we attempt to measure the observable phenomena that compose emotional expression, as well as the contextual factors that contribute to changes in personality, attitudes, and beliefs. We try to assign a numerical estimation to feeling expression according to one quantity relative to another. We have found the operations by which we may meet the necessary criteria for objective measurement.

The Mind State Indicator (MSI) is based on the requirements of measurement in the physical sciences rather than the more subjective requirements of clinical applications. It gives a mathematical representation for data with a large number of latent values that can be tested to determine if they fit well. MSI allows for real-time analysis of a patient's mental state with the proposed analysis using "quantitative measurements . . . based on axiological values and time orientation of lexical features" (Howard 2013). Using MSI, we can analyze a wider range of psychological phenomena than permissible with existing assessment tools. For instance, we can define precisely emotional states in Time and Space.

FIG. 4 illustrates several examples of application of the MSI to authentic expressions labelled as Depression (MSI<0).

Figure 5:
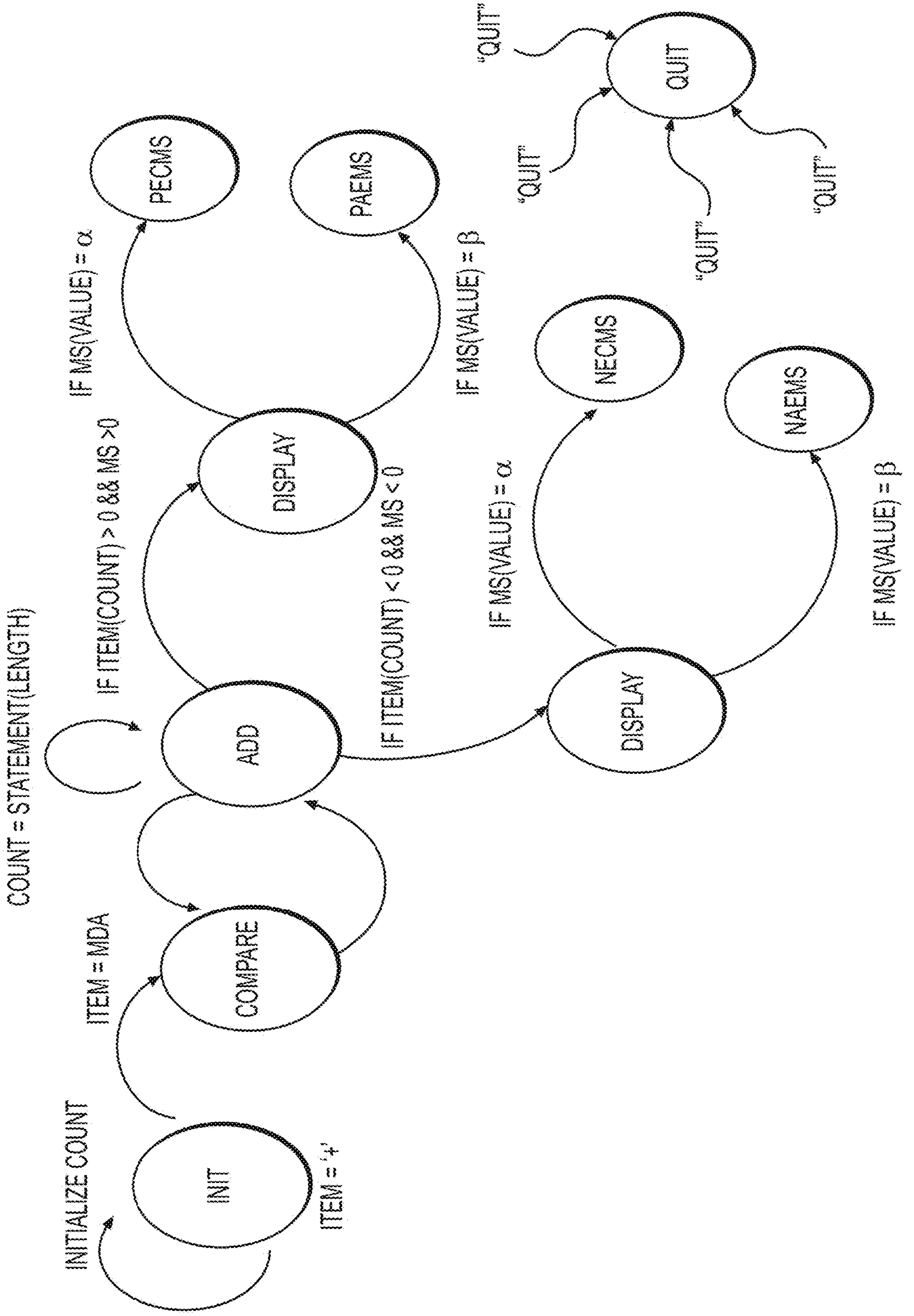
FIG. 5 illustrates an example of a Graph-based representation of the M ind State Indicator Algorithm.

FIG. 5 illustrates an example of a Graph-based representation of the M ind State Indicator Algorithm.

Figure 6:
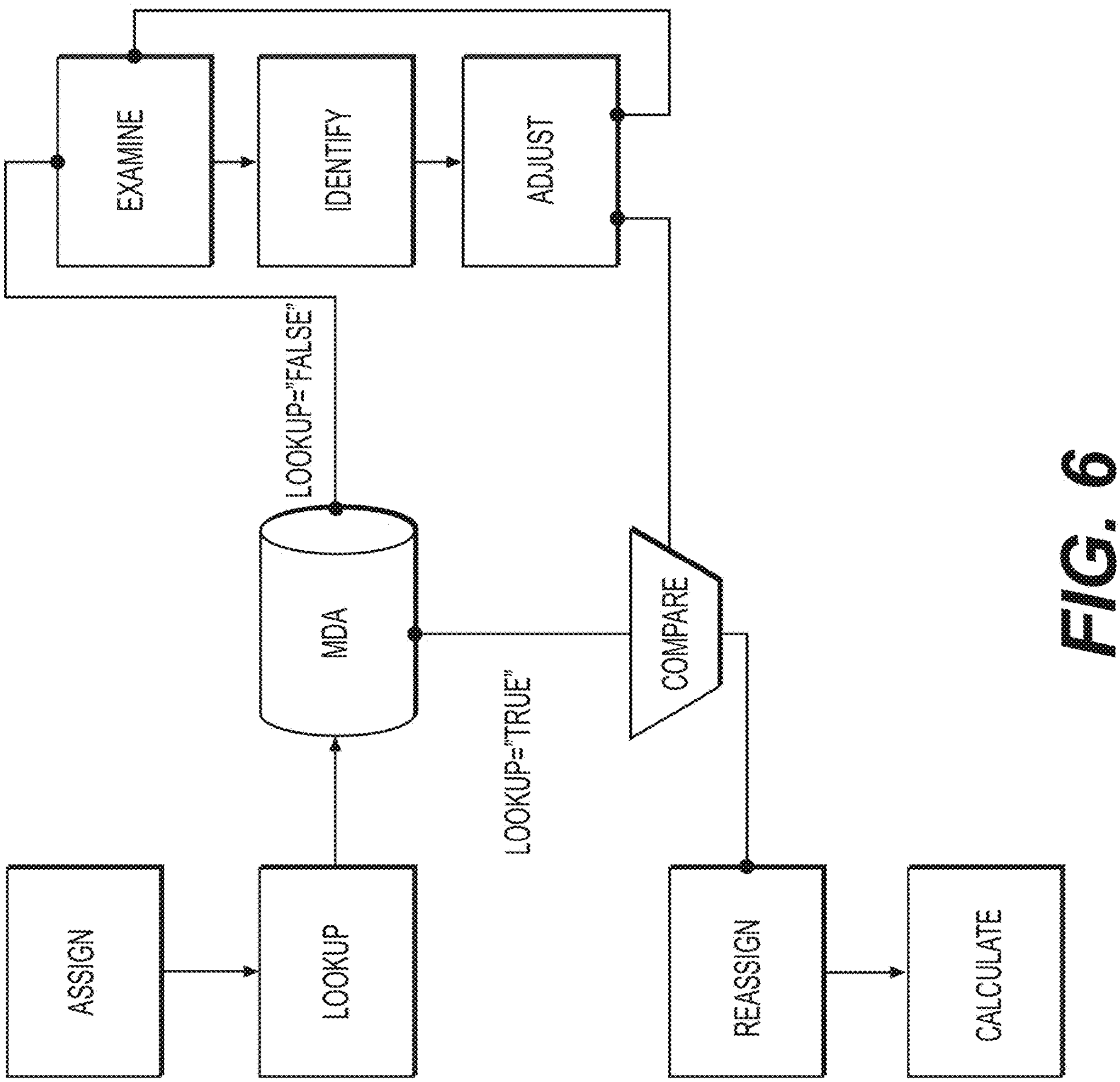
FIG. 6 illustrates an example of Adding the Mind Default Axiology Database to MSI functionality.

FIG. 6 illustrates an example of Adding the Mind Default Axiology Database to MSI functionality.

MSI Framework Analysis

Figure 7:
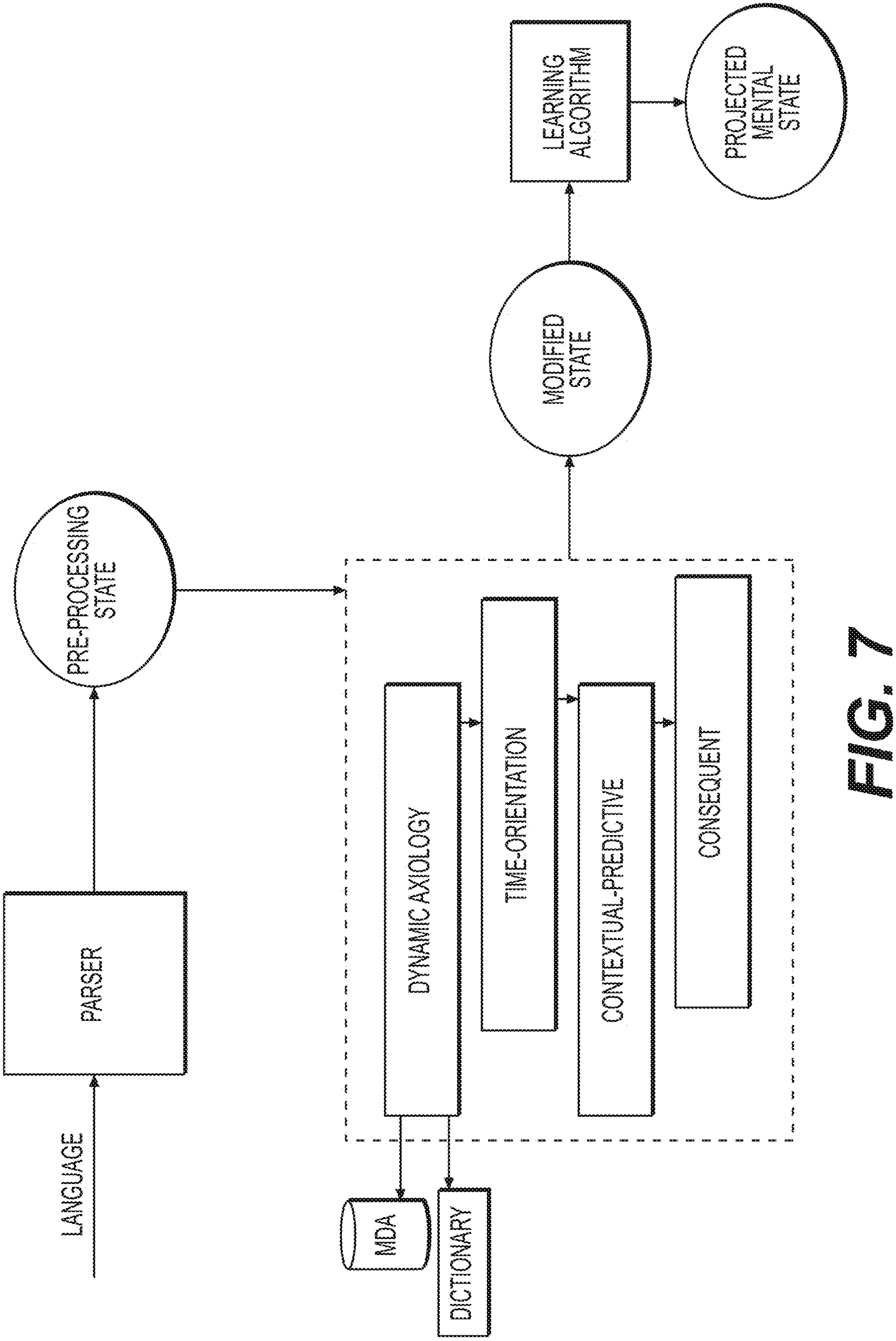
FIG. 7 illustrates a high-level overview of the MSI analyzer.

FIG. 7 illustrates a high-level overview of the MSI analyzer. Much of this architecture can be interchanged based on the testing apparatus in use. This allows the researcher to adjust and fine-tune the system to compensate for errors resulting from a patient's inaccurate descriptions or words that have a particular and unique sentimental value to the patient being examined.

The system also addresses variations in the forms of linguistic expressions independent of the language or dialect it was described in. By using the axiological database of specific languages and applying an accurate parser, we can factor out differences in language and structure from our analysis. Because there are many factors that contribute to how a word is used, perceived, or emphasized, we were led to develop a state analyzer architecture that compensates for such criteria as these. We then used a parser developed at Massachusetts Institute of Technology (MIT) called the START parser, which allows us to retrieve the components of each word used and better analyze its grammatical structure.

Pre-Processing State

In the pre-processing state, each sequence of sentences is broken up and fed to the analyzer as a sequence of clauses, each associated with a sentence. There are two types of clauses, which are relevant to the computation of word values. These are "has_tense" and "word_root" clauses. If the verb is not in the MDA database it can be annotated manually as "+" for present/future tense, and "−" for past tense. In order to count "has_tense" clauses, we leverage the fact that "word_root" clauses always come after "has_tense" clauses. As such, when the server is processing a "has_tense" clause, it first looks up the word in the dictionary. Then, if the word is found, the sentence value is left unchanged (since the value of the word will be appropriated added later when the corresponding "word_root" clause is processed), and if the word is not found, the sentence value is incremented or decremented according to the tense. In the latter case, the verb is stored to a list variable "tense_counted" so that they can be rendered properly in the front end. The modular engine consists of several modular constructions joined by logical data dependencies where each plays a significant role in evaluating a given discourse. The framework is divided into several modules, as described in the following sections.

Dynamic Axiology Module

The data here is compared to a mind default axiology (MDA) database and a given pre-defined dictionary. The role of this module is to identify and retrieve the value associated with identical words.

The processing of "word_root" clauses in this module is simple, if the word is looked up in the database or dictionary, and if its value is found, it is counted, else it is not counted. The value of the word is determined either by the lookup, which has just occurred, or by the previous counting of a "has_tense" clause, which can be found in the list "tense_counted."

The resultant of such lookup will be stored at the given module. This mechanism will iteratively continue until the whole sentence has been processed.

Figure 8:
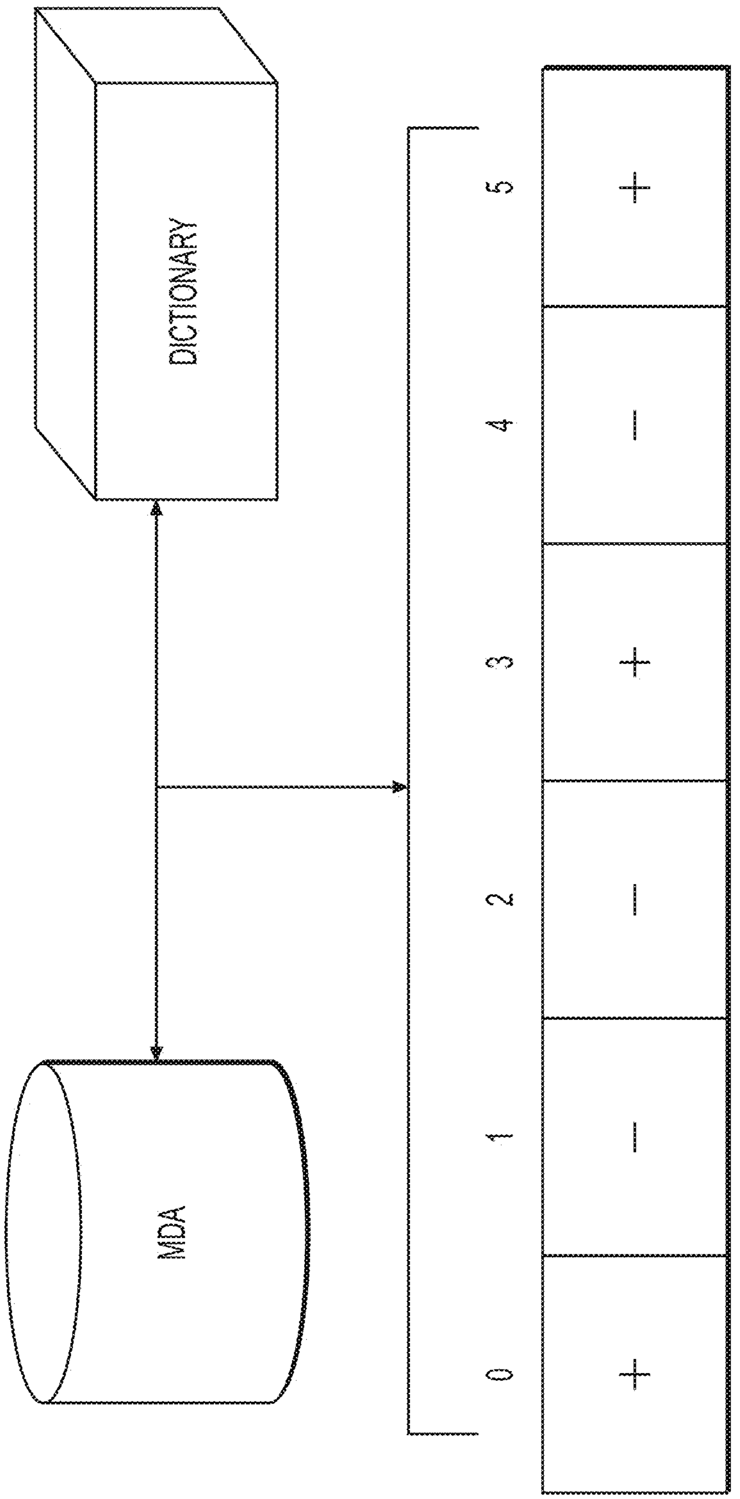
FIG. 8 illustrates how both the MDA and dictionary contribute to the value for each word string and dictionary database mapping with the MDA.

Labeling each word with its value enables us to compute and update sentence values in linear time. FIG. 8 illustrates how both the MDA and dictionary contribute to the value for each word string and dictionary database mapping with the M D A.

```
set axiology_value (set mda, set dictionary)
{
int i;
for (i=0; i <= sentence_length; i++) {
axiology_value = mda ^ dictionary ;
}
return axiology_value;
```

This pseudo computes the axiology value of the word based on AND'ing the values from both the MDA and dictionary. Using this logical operation we can account for the values retrieved from both databases while outputting the desired result.

A straightforward string-matching algorithm is implemented to identify matching word patterns.

```
Int findmatch (char *p, char *t)
{
int i, j;    /* counters */
int m, n;    /* string lengths */
m = strlen(p);
n= strlen(t);
for (i=0; i<=(n−m); i=i+1) {
j=0;
while ((j<m) && (t[i+j]==p[j]))
j=j+1;
if (j==m) return (i);
}
return (−1);
}
```

Time-Based Module:

This module accounts for time orientation. Time is very essential in analyzing a patient's mood. Research suggests that individuals will separate their personal experiences, the basis of memories, into the psychological time frames of past, present, and future (Gonzalez and Zimbardo, 1985; Zimbardo and Boyd, 1999). These memories, good or bad, have different implications on current behavior and future directions. Zimbardo also maintains that individuals with a more future-based time perspective, for example adopting goals to achieve, exhibit greater psychological satisfaction than those who do not. Hence, a tense that represents the past is considered to be negative, while a tense representing the future is considered positive. Many sentences carry their own representation of the tense as a whole in which case we need to account for such tenses. Therefore, the module examines the tense of a given word and verifies its time projection.

4.2.3.4 Contextual-Predictive Module:

Based on sentence analysis, this module is responsible for identifying words that can affect the value of succeeding words. Therefore, some words that can be linked to others will affect their values. The module takes into account these combinations and creates a database that identifies them in various languages. Hence, contextual words are either negative or positive. For example, "my life" is positive, "life" is intrinsically positive and "my" is positive since it is linked to it. There are several algorithms to represent this mechanism, perhaps one of which is the use of the nearest-neighbor heuristic. This approach not only allows us to identify the nearest words within a sentence but it can also be used to correlate those words that have a contextual connection within different sentences.

Consequent Module:

Words are traced throughout the whole modular process then word values are computed for each module separately. This module is used to allocate words that carry a meaning in themselves. Many compound nouns such as 'nothing', 'nowhere', 'somebody', etc. have either a positive or negative value based on what they represent. For example, the word nothing is opposite to something, which has a positive value, hence nothing is negative. This module computes the values for each word, logs are generated for each stage and at each level of a given paragraph. The value from each modular iteration is then convoluted with the value from the other modules.

Figure 9:
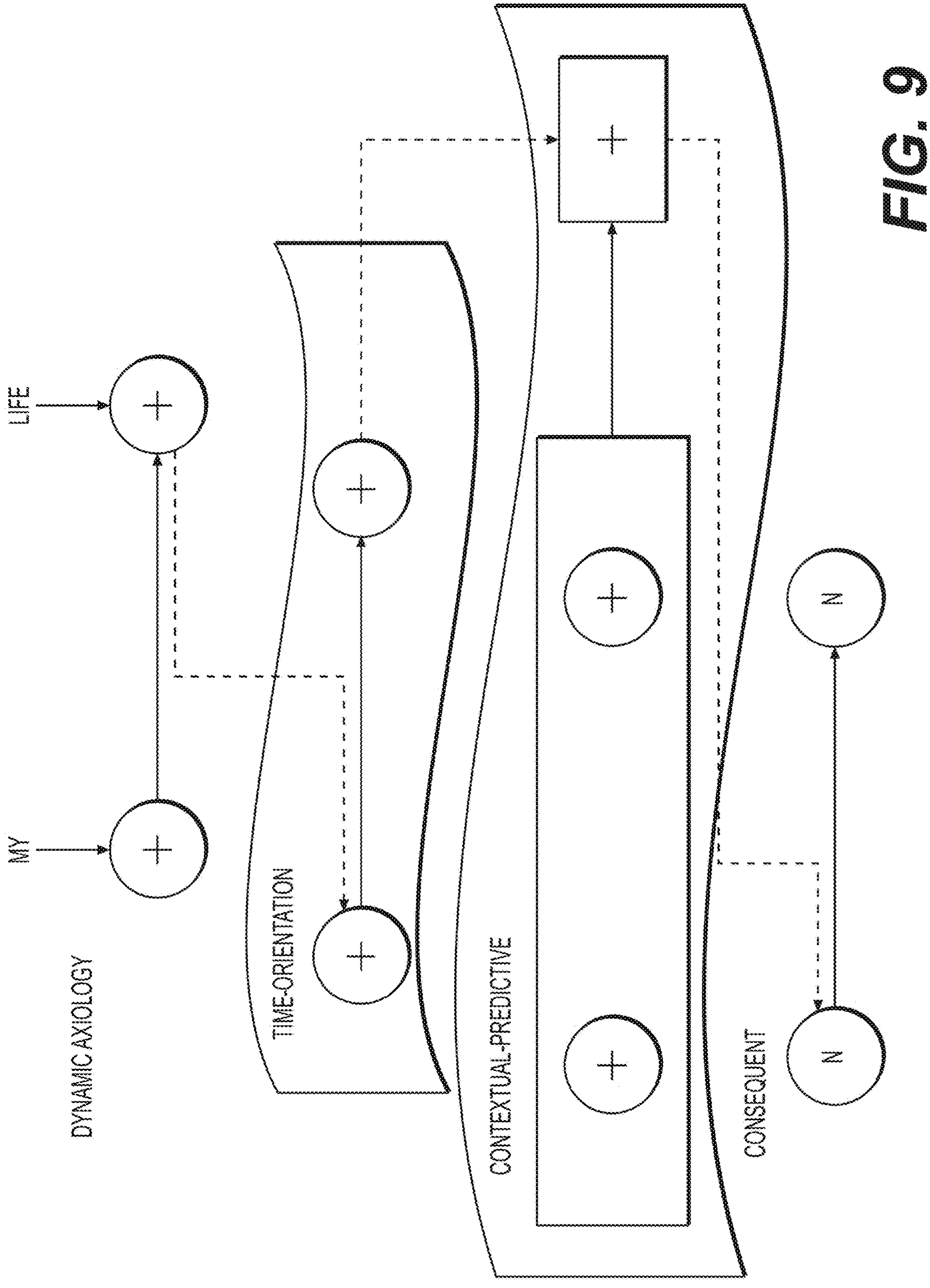
FIG. 9 illustrates assigning value to discourse elements using LXIO.

FIG. 9 illustrates assigning value to discourse elements using LX IO

Modified State

This is the initial state representing the resultant mood value based on the modular architecture. This value is the approximate representation of each mood state, however it is still dependent on the history of the patient and their different word representations.

Project Mental State

We are applying a learning algorithm that looks at various instances and tracks a patient's word analysis history. This algorithm takes into account the resultant modified state and redefines the word values based on the history of the patient. Once every word is clearly defined or calculated, the mood state is represented based on the unary summation of the words forming the full sentence. To further explain this notion it is important to look at how this unary system behaves.

Unitary System Foundations

Topology

The topology of the MSI system generates mood states by examining the mind's abstract structures, based on cognitive conceptual containers known as the Fundamental Code Unit (FCU). Throughout the brain there are various forms of activations (electrical, chemical, biological) each contributes individually or within groups to the formation of new concepts, which define a positive or negative mental state. Series of such activations form an activation set, this set represents a connected structure for each activated region, which is defined in terms of a node. The node circumference changes based on the duration of the region being activated and the reflexivity is due to the re-activation of this region at different instances.

Each node representing a form of activation can also be connected to another node that can vary in shape and time orientation. The segment connecting the various nodes to one another represents the time orientation. Once this connected structure is formed, a new activation set is created. This activation set can also be connected with other activation sets to create a concept set. In other words, nodes within the same set are added together based on the unary system computation and they are represented in terms of waveform signals that are weighted by a statistical coefficient to produce a resultant active node. The concept set is the set of concepts derived from the connected-activated sets, which produce an axiological value that represents a mood state after being projected on a positive and negative plane.

The concept set is defined by the activation set with higher value. Therefore, a concept can be formed when other activation sets are elements of it but their contribution (effect) is diminished by another dominant activation set. The value of the resultant concept set can have various ranges from positive infinity to negative infinity, only after its projection that these values become a unitary positive or negative. The model is based on the FCU framework, which analyzes at the quantum, biochemical, and abstract concept levels.

Calculation of Axiological Values

Calculating axiological values requires a mathematical equation but no experiment in order to determine the values, whereas an experiment (e.g., the concept of frequency as an estimation of value or a Bayesian inference) is requisite to calculating values after the fact.

The axiological system for our predictions contains several values, each representing a cognitive state, which may come to change because it is not static. In order to avoid making contradictory attributions for a single value, a series is examined rather than isolated values. There are four possible attributions:

State 1: Positive (+)

State 2: Negative (0)

State 3: Neutral (N)

Furthermore, within the attribution system:

Positive values are so either intrinsically or as a consequence

Negative values are so intrinsically, as a consequence or through context

Intrinsically positive values keep their positivity throughout the process and can affect the value of surrounding words (e.g., "my"+"husband")

To show the system's full range of possible applications, we establish that positive intrinsic values are stable for several cognitive states. Consequently, a value depends on the first positive attribution, otherwise known as a non-homogeneous Markov chain. Thankfully, it is easily turned into a homogeneous chain by adding an artificial state for each new attribution. For example, instead of a stable positive fourth state, we would find:

[ . . . ]

State 4: Positive, at the beginning of the attribution ("my")

State 5: Positive, second addition ("husband")

State 6: Positive, third addition ("my wonderful husband"); etc.

The probabilities linking two consecutive artificial states (e.g., the $3^{rd}$ and $4^{th}$ attributions) are given a value of 1 because it is accepted that all attributions that are started are also finished (the opposite could also be true by changing the value of the probabilities). In order to change the attribution process, fictitious states would need to be added (at the moment of the attribution, one year since the last attribution, etc.

The Matrix for P is written as follows:

$$P = \begin{bmatrix} \frac{97}{98} & \frac{1}{98} & 0 & 0 & 0 \\ \frac{2}{73} & \frac{65}{73} & \frac{6}{73} & 0 & 0 \\ 0 & 0 & \frac{12}{13} & \frac{1}{13} & 0 \\ 0 & 0 & 0 & 0 & 1 \\ 0 & 0 & \frac{7}{8} & \frac{1}{8} & 0 \end{bmatrix}$$

Within this matrix, Pn gives the transition probabilities of n number of states. Therefore, $P^n_{ij}$ is the probability of being in state j at the end of n years for a subject that started with axiological value i. In order to find out what happens to a subject after n years, the following needs to be written:

$$[1\ \ 0\ \ 0\ \ 0\ \ 0] \times P^{(n)} = \begin{bmatrix} p_1^{(n)} \\ p_2^{(n)} \\ p_3^{(n)} \\ p_4^{(n)} \\ p_5^{(n)} \end{bmatrix}$$

Here, $P^n_i$ equals the probability of being in the axiological value (or state of mind) i after n years, assuming that the series began with a positive value. If the number of units in each series at year 0 is known, a simple Y vector must be calculated 1×[neutral positive negative positive-negative]×Pn=Y. This method allows us to separate the units of the different axiological values (after n times). By multiplying the Y vector by the total number of units, we get the amount for each value after n times.

Statistical Estimation of Axiological Values

Statistical estimation produces a value based on a language sample or a certain number of results taken from an interview with a subject. This type of estimation frequently rests on the principle of maximum likelihood. Statistical analysis is specifically where quantification via the four values specified above (grammatical, intrinsic, contextual, and consequent) becomes most pertinent for the application of Intention Awareness. By performing data collection and analysis along these variables, variations in sentence structure can be attributed to behavioral pr linguistic norms (or oddities) and paired with the corresponding change(s) in intention.

An estimate based on the number of times a word appears helps determine the probability of an axiological value once all possible values have been determined and once the value attribution can be reproduced repeatedly and independently. More specifically, this estimation can help determine the probability of obtaining a negative or a positive state of mind. For example, in a case where there are N value attributions and NF is the number of times the attributed value is negative, then if N becomes increasingly bigger, we can assume that the ratio of NF to N (NF/N) would become gradually closer to one over two (½); which leads us to define the P(F) probability of obtaining a negative value as being the limit when N tends towards infinity:

$$\lim_{N\to\infty} \frac{N_F}{N} = \mathbb{P}(F).$$

This probability estimation of value is an exception to the rule of large numbers; for example, in the situation where the unpredictable variable X is equal to 1 or 0.

The main problem with this method lies in that the value attribution has to be repeated a large number of times, but in practice it is difficult to test a subject's entire language production. Therefore, the estimate is restricted to a sample of language production in the hope that the value thus calculated provides an accurate evaluation. The goal is to obtain non-biased, consistent, efficient, and well-founded value estimations, which can be done using a similarity function containing the desired parameter:

$$L(x_1, \ldots, x_i, \ldots, x_n; \theta) = f(x_1; \theta) \times f(x_2; \theta) \times \ldots \times f(x_n; \theta) = \prod_{i=1}^{n} f(x_i; \theta).$$

In general, the resulting value estimation is the best possible, albeit somewhat inaccurate, given that empirical data is being used to prove a theoretical rule of probability. In the case of discrete probability distribution, each sample has the probability estimator pk and the frequency fk. Since theft variables are inconsistent, it is natural that these estimators not coincide completely with the pk values. In order to measure the significance of these variations, adequacy tests such as the $\chi^2$ are conducted.

Statistical Learning of Values

Bayesian inference can also be used in order to create apprenticeship processes. The initial value, or intrinsic value, is reviewed throughout the trials. The decision of which value to use is based on restrictions imposed by the distributions of the values. The compatible distribution with the maximum entropy is the best option as it contains the least amount of added information. Bayes' theorem helps with the revision of this initial value, equal to P (hypothesis), as it explains the probability of a hypothesis given observed evidence and the probability of that evidence given the hypothesis. A new probability is deducted from this proof. The terms proof and hypothesis were chosen in order to show the link that should exist between the two states as well as the asymmetrical character of these two states.

For this method to be successful in practice, the proof state must either be more or less probable than the occurrence of the hypothesis state. These two states cannot be independent of each other. For example, examining a subject's language production determines what cognitive process will be used. We know the probability that the language production will show signs that the subject suffers from a psychological disorder because a disorder has been diagnosed is P(M|PTSD)=0.9, and the probability that he is healthy based on how well he behaves is P(M|Healthy)=0.2. These probabilities have been estimated based on other methods used on previous productions. In this context, M indicates that the language production predicts the subject's cognitive process. Starting with the intrinsic value that the word will be either positive or negative (P(Negative)=½), we believe there is basically a fifty percent chance that it will be negative. The working hypothesis is that the subject is depressed. Based on this, we hypothesize that the probability of the language production being negative is:

$$P(M) = P(M|PTSD) \cdot P(PTSD) + P(M|\text{Healthy}) \cdot P(\text{Healthy}) = 0.9(0.5) + 0.2(0.5) = 0.55$$

Therefore, the prediction is that 55 percent of the time, the language production will be negative. As a result, the probability that the subject is depressed, based on the fact that the language production has a negative prediction, is given b the following equation:

$$P(PTSD|M) = P(M|PTSD) \cdot P(PTSD) = 0.9(0.5/0.55) = 0.82\,P(M)$$

Based on this, we could prove our hypothesis that the subject is depressed by examining a different language production sample with the above calculation of negative probability as our initial value. This method provides the possibility of revising the axiological value that we have attained based on whether a future state will be positive or negative.

Conclusion

Machine learning algorithms and MSI are two methods that will be used by the BCCS. In order to be clinically relevant additional data streams and methods will need to be added.

Section Five: Machine Learning Experiments

Diagnosing PSD has many complex challenges that too often result in misdiagnosed or undiagnosed cases. PSD symptoms vary greatly between every patient in all aspects including onset, duration, and severity. This continuum of post trauma responses also closely resembles a cluster of diseases with similar symptomologies, including depression, addiction, adult ADHD, generalized anxiety disorder, and panic disorder. All of these conditions are difficult to diagnose because they vary case by case and are often comorbid to each other. The current clinical standard for PTSD by a general practitioner is inadequate; based on subjective methods unable to differentiate between disorders. The success of the diagnosis and treatment depends largely on the experience of the physician's best guess. In addition, there are huge numbers of cases that go unrecognized and undiagnosed because either the individual or the physician does not identify the symptoms as PSD. There is evidence to suggest that the rate of accurate clinical diagnosis of PTSD occurs in as little as 4% of individuals who actually have the disorder.

The following experiments are a preliminary trial inquiries towards developing a PSD detection tool based on machine learning. The advantages of this proposed assay are numerous: 1) objective 2) non-invasive 3) Cost optimization 4) large scale screening 5) would not require a physician to administer. These benefits may be tangible if we can prove that machine learning is capable of the analysis and that the data is sensitive enough to produce an accurate diagnosis (at least as accurate as current methods if not more). The two experiments in this section are basic and simplified to demonstrate that the machine learning using brain code algorithms can analyze PSD datasets. Additionally these two experiments illustrate the accuracy and objectivity of the objective measures (ToDM) we propose for the BCCS.

Experiment 1 can Blogs and the Brain Code Identify Depression from Controls Using Machine Learning

Background

This preliminary data study explores a more objective method for diagnosing PSD and differentiating responses of trauma from other disorders. Machine learning methods of analysis are applied to open source text from blog posts. The analysis aims to identify samples with features of depression from neutral samples.

Data

The dataset consists of 350,000 posts by 19,320 bloggers with and without depression. The blog posts were data mined from screened, credible sources. The dataset includes 30,000 unique words (Neuman et al. 2012). Each blog post was manually annotated.

Claim

Depression is the result of emotional and chemical imbalances. Therefore everything a depressed person says or writes is unconsciously affected by these features of their brain. Therefore is it possible to classify natural language from someone who is depressed compared to someone that is not depressed? This study aims to extract specific linguistic features of depressed text.

Data Analysis 19,320 blog posts from CMU Twitter Tagger output. Every blog post was labeled with the following textual features:

(i) countAdj (number of adjectives)

(ii) countAdv(number of adverbs)

(iii) countNoun (number of nouns, proper nouns, and proper nouns+possessives), (iv) countVerb (number of verbs)

(v) countIntj(number of interjections).

The sum of these five features gives us the totalPos.

Every blog post was analyzed for the following features (i) Word N-grams: Frequencies of contiguous sequences of 1, 2, or 3 tokens. The TF-IDF weighting scheme is applied.

(ii) Sentiment140 Lexicon: The Sentiment140 Lexicon contains 62468 unigrams and 677698 bigrams along with their polarity scores in the range of −5.00 to 5.00. Considering all uni/bi-grams with polarity less than 1.0 to be negative and with polarity greater than 1.0 to be positive, we count the number of negative (negativesCount) and the number of positive (positivesCount) uni/bi-gram occurrences in every blog post (Poria et al., 2014f).

(iii) polarityMeasure was calculated based on the positivesCount and negativesCount. The maximum polarity value (maxPolarityValue) is the most positive or most negative polarity value of all polar uni/bi-gram occurrences in the tweet.

(iv) SenticNet

Results

We obtained 79.21% accuracy when classifying whether the text was from a depressed or non-depressed person. The n-gram features alone gave an accuracy of 62.39%. Adding the sentiment lexicon based features increased to the accuracy significantly.

Experiment Two: Can Machine Learning and Multimodal Data be Used to Differentiate PTSD from Non PTSD

Background

Similar to Experiment 1, machine learning data analysis was used on open source data to classify depressed patients from controls. Using multimodal data, visual and audio features of behavior were parsed and analyzed according to extraction features of interest. Using machine learning algorithms the data was tested for accurate detection of depression.

Data

Audio, visual, and text data was used in order to demonstrate a multimodal analysis. 26-recorded interviews were screened and collected from open source datasets. The sample included interviews with clinically diagnosed PTSD patients. Audio data was recorded and filtered for quality optimization. Each interview was also transcribed into text. Video was broken down into frames focused in on facial expressions. Consistency between data frames was maintained.

Data Analysis

Speech Analysis

We used openEAR software to analyze the audio data. The following features were extracted:

Short Time-Based Features

Short time-based features are mainly used to distinguish the timbral characteristics of the signal and are usually extracted from every short-time window (or frame), during which the audio signal is assumed to be stationary Mel-Frequency Cepstral Coefficients (MFCC)

MFCC are calculated based on short time Fourier transform (STFT). First, log-amplitude of the magnitude spectrum is taken, and the process is followed by grouping and smoothing the fast Fourier transform (FFT) bins according to the perceptually motivated Mel-frequency scaling. The Jaudio tool gives the first five of 13 coefficients, which produce the best classification result (Poria et al., 2014a).

Spectral Centroid

Spectral centroid is the center of gravity of the magnitude spectrum of the STFT. Here, Mi [n] denotes the magnitude of the Fourier transform at frequency bin n and frame i. The centroid is used to measure the spectral shape. A higher value of the centroid indicates brighter textures with greater frequency (Poria et al., 2014a). The spectral centroid is calculated as $$C_i = \frac{\sum_{i=1}^{n} nM_i[n]}{\sum_{i=1}^{n} M_i[n]}.$$

Spectral rolloff is the feature defined by the frequency Rt such that 85% of the frequency is below this point:

$$\sum_{n=1}^{R_i} M_t[n] = 0.85 \sum_{i=1}^{n} M_t[n].$$

Spectral flux is defined as the squared difference between the normalized magnitudes of successive windows (Poria et al., 2014a):

$$F_t = \sum_{n=1}^{N} (N_t[n] - N_{t-1}[n])^2,$$

Root mean square (RMS) is calculated for each window. Suppose xi is the energy of each sample and N is the total number of samples. Then RMS is defined as $$\text{RMS} = \sqrt{\frac{\sum_{i=1}^{N} M_i^2}{N}}.$$

Compactness is calculated as the sum over frequency bins of an FFT. It is a measure of noisiness of the signal.

Time domain zero crossing is a timbral feature which is also used as a measure of noisiness of the signal (Poria et al., 2014f).

Long Time-Based Features

Long-term features can be generated by aggregating the short-term features extracted from several consecutive frames within a time window. We have used derivate, standard deviation, running mean, derivative of running mean, and standard deviation of running mean as the aggregation methods of short time-based features listed above To find the human perceptible pattern for the signal we extracted three main semantic features: beat histogram feature, beat sum, and strongest beat in the audio signal (Poria et al., 2014f).

Beat histogram is a histogram showing the relative strength of different rhythmic periodicities in a signal. It is calculated as the auto-correlation of the RMS.

Beat sum is measured as the sum of all entries in the beat histogram. It is a very good measure of the importance of regular beats in a signal.

Strongest beat is defined as the strongest beat in a signal, in beats per minute and it is found by finding the strongest bin in the beat histogram (Poria et al., 2014a; Poria et al., 2014f).

Ext Based Analysis

We manually transcribed each video and then analyzed each feature. Our analysis found sentiment and emotion to be important features. The bag of concepts features also carry important role.

Bag of concepts: For each concept in the text, we obtained a 100-dimensional feature vector from the EmoSenticSpace (Poria et al., 2014f). Then we aggregated the individual concept vectors into one document vector through coordinate-wise summation:

$$x_i = \sum_{i=1}^{N} x_{ij},$$

where xi is the i-th coordinate of the document's feature vector, xij is the i-th coordinate of its j-th concept vector, and N is the number of concepts in the document. We have also experimented with averaging instead of summation:

$$x_i = \frac{1}{N} \sum_{i=1}^{N} x_{ij},$$

Sentic feature: The polarity scores of each concept extracted from the text were obtained from SenticNet and summed to produce one scalar feature (Poria et al., 2014f).

5.2.5 Facial Expression Analysis

We processed each video using GAVAM software to extract facial features and Luxland software to obtain facial characteristics points (FCP). Our analysis included the following feature extractions from facial expressions. Table 4 shows Luxland features (Poria et al., 2014f)

- Distance between right eye and left eye
- Distance between the inner and outer corner of the left eye
- Distance between the upper and lower line of the left eye
- Distance between the left iris corner and right iris corner of the left eye
- Distance between the inner and outer corner of the right eye
- Distance between the upper and lower line of the right eye
- Distance between the left iris corner and right iris corner of the right eye
- Distance between the left eyebrow inner and outer corner
- Distance between the right eyebrow inner and outer corner
- Distance between top of the mouth and bottom of the mouth Table 5 shows GAVAM features (Poria et al., 2014f)

- The time of occurrence of the particular frame in milliseconds.
- The displacement of the face w.r.t X-axis. It is measured by the displacement of the normal to the frontal view of the face in the X-direction.
- The displacement of the face w.r.t Y-axis. The displacement of the face w.r.t Z-axis.
- The angular displacement of the face w.r.t X-axis. It is measured by the angular displacement of the normal to the frontal view of the face with the X-axis.
- The angular displacement of the face w.r.t Y-axis. The angular displacement of the face w.r.t Z-axis.

Figure 10:
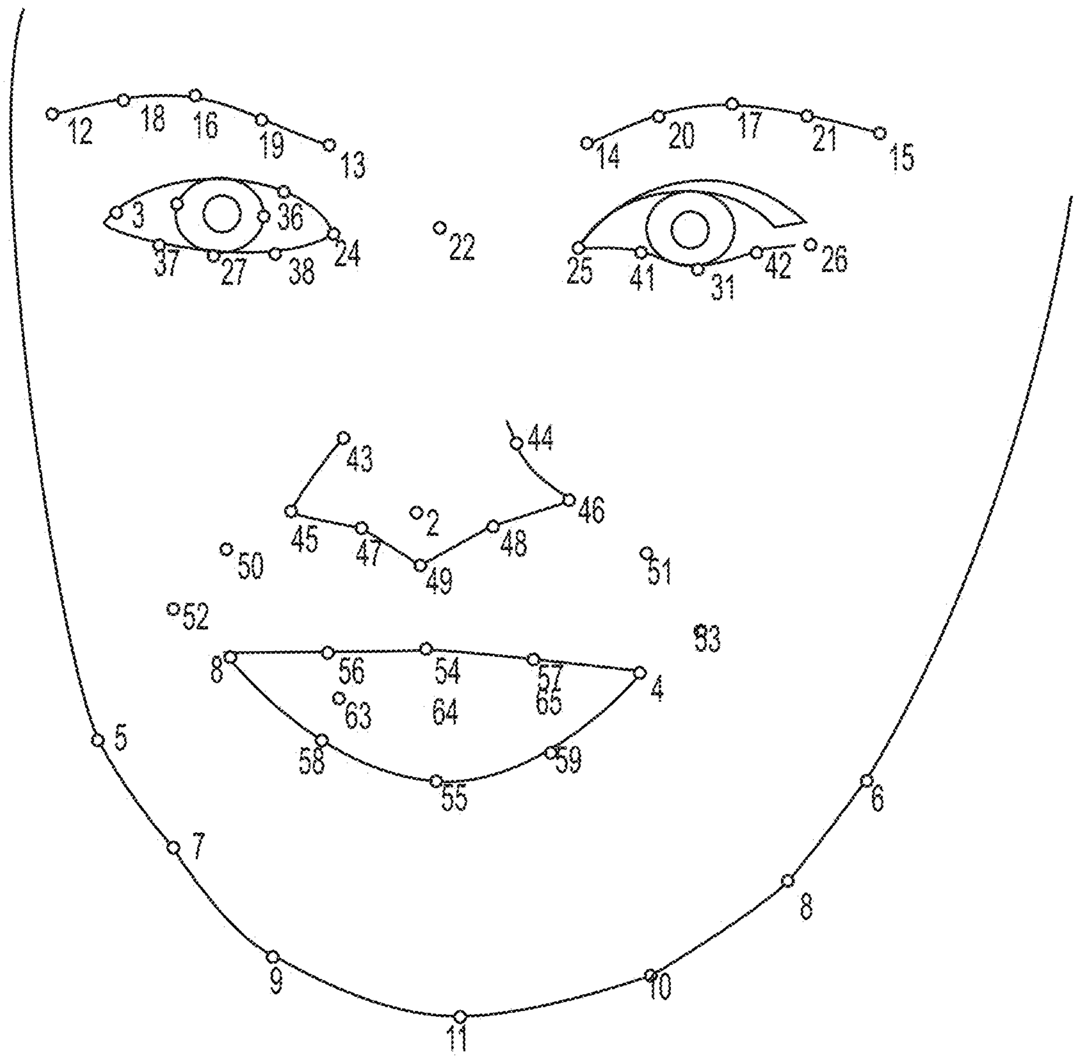
FIG. 10 illustrates Facial Characteristic Points detected by Luxland software.

FIG. 10 illustrates Facial Characteristic Points detected by Luxland software. We used the FCP number with F_n to represent each FCP.

1. Short Difference between F_13 and F_14
2. Long distance between F_29 and F_16 for left eye, F_17 and F_31
3. Long distance between F_3 and F_4.
4. Long distance between F_52 and F_53.
5. How frequently the points between the eyes are not visible (very frequent for PTSD patient).
6. How frequently the points between the leaps are displaced from their original position i.e. when they start talking. (less frequent for PTSD patient)
7. The displacement of the face w.r.t X-axis
8. The angular displacement of the face w.r.t Z-axis.

5.2.6 Results

Our analysis found certain facial features in video data from PTSD patients that distinguished them from videos of non-PTSD patients. These features were more prominent in PTSD patients than in non-PTSD subjects. We acknowledge that these results do not clinically detect or diagnose PTSD simply from classifying facial features. The results are only preliminary to see the potential usefulness of the method.

Using the extraction features described we found significant differences between PTSD and non-PTSD subjects. The strongest beat feature is significantly lower for PTSD patients compared to non-PTSD subjects. Also low frequency of the speech signal, many pauses in the speech signal, and non-steady speech signal were significantly different in PTSD subjects.

5.2.7 Discussion

This preliminary study shows that the task is computationally feasible. A follow up study with larger datasets, varied subject groups, and additional extraction features will be conducted. Additional studies using combinations of multi-modal data of movement, language, and facial features will also be conducted.

One of the disadvantages of these studies is the lack of training data. For future work an algorithm based on the PTSD symptoms from the DSM V will be created to build the model. Data analysis will correlate PTSD symptoms and the extraction features using the algorithm.

5.3 Conclusion

These data analyses, although preliminary, demonstrated the potential of detecting PSD with the BCCS using machine learning. We acknowledge that these data studies have their flaws. The first study used manual annotation, which carries an unavoidable human error and subjectivity. The second study lacked adequate classifiers and of course the PTSD diagnosis of the subjects cannot be confirmed. Furthermore it is not known what methods were used to diagnose. Screening tools such as Primary care PTSD screen could have determined the diagnosis or it could have been a Clinician administered PTSD Interview may have been used. Because we do not have this information causes an inconsistency and unknown variable that may have affected the outcome of the study. Additionally that goes without saying that the subjects identified as controls may not necessarily accurate as misdiagnosis and undiagnosis is prevalent among these psychological disorders (as disused throughout the previous sections). These limitations add an additional layer of complexity, nevertheless the computational methods of analysis were transparent in demonstrating a level of accuracy that is worth exploring further. The next section details the proposed future work of the BCCS, which uses the machine learning methods and algorithms that were validated in our two data experiments.

6 Chapter Six Future Work—LEAPS

The overarching aim of the Longitudinal Evaluation of Adult Post-traumatic Syndromes consortium (LEAPS) is to develop a comprehensive, biomedical, nonintrusive, mobile 'sensor' system to characterize post-traumatic trajectories based on non-invasive measures of pathophysiological, behavioral, cognitive, and emotional and other neurobiological outcomes. These outcomes may serve as objective biomarkers, which should aid the scientific community in better understanding the course and trajectory of posttraumatic syndromes and work towards developing promising targets for intervention. To capture the full spectrum of post trauma syndromes requires a large amount of serial longitudinal data from a large population of patients, and several dimensions of measurable outcomes over time. We have successfully used comparable prototypes for the early detection of neurodegenerative disease with results that demonstrated early detection and classifications of types of neurodegenerative disorders (Parksinon's, Alzheimer's, Huntington's)[14]. The same approach has also been used successfully for the objective detection of pain.

Our hypothesis is that post-traumatic syndromes are segregated into different phenotypes with distinct clinical trajectories on the basis of measurable outcome variables.

Specific Aim 1: Collect a) Deploy LEAPS device, a wireless, non-invasive, multi-level, multi modal, data collection tool, by further refining the Brain Code Collection System (BCCS) for post trauma targets of dimensional measure (ToDM)
b) Establish LEAPS methodologies and quality control at 3 major International trauma centers.
c) Use BCCS algorithms and codes to train machine-learning classifiers to collect, process, store and analyze large, multi-level datasets on a cloud storage platform for later sharing as 'raw' and or 'constructed' data
d) Collect serial, longitudinal ToDMs from 2000+ acute trauma patients for at least 3 years.

Specific Aim 2: Analyze & Classify a) Analyze individual ToDMs to identify pathophysiological changes and cognitive changes in relation to clinical function over time in Tier 1 Analysis.
b) Identify subgroups of interest (SOI) and biomarkers of interest (BOI) leading to the segregation of distinct phenotypes in Tier 2 Analysis.
d) Assess and classify functional relationships between BOIs and clinical phenotypes in Tier 3 Analysis.
e) Construct and test risk prediction algorithms and potential targets for Intervention (TFI)

Specific Aim 3: Predict & Share a) Further validate risk prediction algorithms based on clinical phenotypes and BOIs b) Identify actionable biomarkers and promising TFIs
c) Design target development studies, pilot proof of concept studies and clinical treatment studies
d) Invite research and clinical communities to facilitate analysis beyond the scope of this project and integrate with existing research.

2.1.2 Site Selection

Our team feels that in order to reach a more comprehensive understanding of phenotypical characteristics of reactions to traumatic stress, data collection cannot be limited to a single group, culture, or location. Therefore the partners of the LEAPS consortium have initiated a network of international trauma centers spanning the French West Indies, United Kingdom, and North America.

Martinique

University Hospital of Martinique (UHM, CHU de Martinique)

The University Hospital of Martinique (CHU Centre Hospitalier Universitaire) provides 24-hour service for all types of patients (adults, children, neonates, pregnant women) pre and In-hospital emergencies. In addition UHM provides a very efficient Mobile Emergency Service (SAMU) with highly trained medical responder teams available 24/7 anywhere on the Island via Ambulance, Helicopter, or Aircraft. The A/E (Accidents and Emergencies) Department works 24-Hours a day and assesses, treats, and resuscitates patients who have been injured or are severely ill. More than 100,000 patients are administered to the A/E Department every year. Patients are cared for by specialized medical staff with experience to deal with all life-threatening situations. The A/E Dept. is closely linked with all 24-Hours Medical and Surgical in Hospital Services Such as Stroke Center, Trauma Center, ICUs, Catheters Labs, CT Scan, and OR. The Adult A/E Dpt is on the lower ground floor of the main Hospital of the University Hospital of Martinique (CHU de Martinique). There is a significant need for psychotraumatology on the island of Martinique Centre Hospitalier General Louis Domergue The Emergency Room in this medical center admits around 90 patients per day. It is considered the main ER of the North Atlantic.

United Kingdom

John Radcliffe Hospital

Oxford University Hospitals (OUH) is a world-renowned center of clinical excellence and one of the largest NHS teaching trusts in the UK. Over six percent of patients are delivered from 44 other locations across the region. In 2013 there were 90,000 emergency admissions.

Canada

Montfort Hospital

Montfort Hospital is a University teaching hospital affiliated with the University of Ottawa. The hospital serves over 1.2 million residents of eastern Ontario in 2013-2014 there were 57,000 emergency room visits. Montfort hospital has a research lab directed by Dr. Tempier.

US

Buffalo, NY Police Department

John Violanti has a longstanding relationship with Buffalo, NY police department with whom he has collaborated on several large scale data collection project.

Step by Step Workplan/Methodology

Specific Aim 1: Collect

Initial Investigation

The first objective of this project is to determine exactly what should be measured. A LEAPS committee of experts in PTSD, pain, psychiatry, machine learning, sensor engineering, and neuroscience will discuss the ToDM and decide on the best measures to collect, given the patient population at each trauma center, the sensor capabilities. Device sensors and hardware will be optimized according to final ToMD. Thomas Serre's Lab at Brown University will be responsible for device production.

Refine the BCCS prototype for post trauma Targets of Dimensional Measure (ToDM)

The BCCS is a platform designed for collection of multiple data streams with non-invasive wearable body sensors, image, and audio capture. BCCS is designed for use in a non-clinical setting (at home, at work, etc.) and to be as convenient and comfortable for the patient as possible in order to yield rich, naturalistic data. The existing BCCS prototype has been used and validated in several Parkinson's Disease studies and has undergone several rounds of troubleshooting, therefore for this proposed project we will refine and add to the BCCS prototype to be more adapted and specific for collecting data from trauma patients. Table 6 shows existing BCCS prototypes and modifications to be added for LEAPS.

| Existing BCCS Prototype | Modifications for LEAPS Device |
|---|---|
| EEG Cap | Wireless EEG headset (with added contacts) |
| Upper Body Sensors | Upper limb sensors will be smaller, Bluetooth and infrared |
| Lower Limb Sensors | Lower limb sensors will be smaller, Bluetooth and infrared |
| Audio Capture (headphones and microphone) | Video camera will be built into tablet<br>Audio capture will be built into tablet |

The second generation BCCS will be referred to as the LEAPS device. The BCCS prototype initially built for neurodegenerative disease data collection will be adapted for use in PTSD by 1) refining the BCCS measures of interest (ToDM) 2) integrating optimal sensor hardware and 3) developing a LEAPS app; an interactive tool to procedurally collect data from the patient. Previous work with the BCCS was facilitated in a clinical setting with a person facilitating. This app will replace the need for a person to physically be there with the patient for every data collection session. E-health/telemedicine/mhealth has recently been growing particularly in commercial markets (ex: Fitbit, Nike FuelBand). Some physicians have started utilizing patient-facing apps, such as mobile enabled blood pressure monitors, glucose monitors, ECG Check and many others gaining popularity.

This study proposes to measure upper limb movement, lower limb movement, hyperarousal, cognitive changes, memory changes, speech production, language production, and EEG. To perform this study the LEAPS device will consist of upper limb sensors, lower limb sensors, EKG sensor, EEG electrodes (headset), headphones, mic, video recording, and an interactive app for smartphone or tablets. The chosen ToDM: movement, cognition, speech, facial features, hyper-arousal, and brain oscillatory activity (EEG), will be refined by the Consortium as needed to finalize the specific data streams to be collected from the sensors. With finalized ToDM and hardware the LEAPS app will be designed and developed with input from the software developers, PTSD experts, and sensor experts to ensure the whole system can be integrated to accurately measure each data stream. The app will be similar to many of today's popular apps, creating user-friendly features that will not feel like "data collection." Every week the patient will be asked to login and put on sensor device. First they will answer a series of questions from the Mini International Neuropsychiatric Interview (MINI 5.5), Recent Life Events Questionnaire, and 20 DSM 5 PTSD symptoms. With regards to sensory hypersensitivity, subjects will be asked to report on, localize, and rate their pain or somatic discomfort on a 0-10 Numerical Rating Scale (NRS). Analysis of the change on the Pain Intensity NRS 'as a proportion' has shown to be most consistently correlated with clinically important differences reported on the patient's global impression of change.

The patient will then be asked to play a series of "games/tasks" The games will be randomized by the programmer each week to make certain the patient does a different set of "games" that actually collect consistent data for each ToDM. Each ToDM will be measured with a specific set of behaviors. Because the consortium will finalize the ToDM in phase 1, we cannot describe the specifics of what the games and tasks will be developed, but below we describe examples of BMN Suites of games that were developed for a DOD study. At each trauma center, when a trauma patient is identified and agrees to take part in the study (gives consent, etc.) they will be given a LEAPS system to take home.

The following usability-perspective pipeline will be established:

1. LEAPS Representative (a dedicated postdoc person at each hospital) will set up the patient profile with the patient before discharge (which includes many basic questions and CAPS type questions, etc.), using online versions of the different tests and psychometrics.
2. The LEAPS system will include a customized tablet device pre-installed with the LEAPS app that will be used as the data collection platform. The app will have a tutorial on how to use it, and deliver instructions and tests.
3. The app in the tablet will request the patient login weekly and complete a series of questions, and then tasks/games. These games will be engaging and fun, not feeling like clinical data collection, with games such as tic-tac-toe, memory games, and other popular variations. It will take no more than about 15 minutes, to avoid fatigue and loss of engagement. These simple games will in fact be collecting cognitive/behavioral/psychophysiological data.
4. The app will be very specific and instructive. It will give directions to put on the LEAPS sensors, place the EEG headset, headphones, arm sensors on left arm above elbow, etc. The programmer will randomize the games, so that each week the patient will receive different sets of 'games', while collecting consistent data on a weekly basis, in order to observe changes over time.
5. Automated emails and text messages will be sent to the tablet. If no response is given, the LEAPS Representative will chat or personally phone the subjects in order to determine the problems.
6. In order to promote engagement, rewarding and motivating messages on progress will be sent to the user. Other users progress/scores (gamification techniques) can be used to prompt subjects.

All data will be automatically sent to the cloud storage system.

1. When a LEAPS system is handed over, the LEAPS Representative will create the subject's account, with the initial basic questions, CAPS questions, etc.
2. Every week, subject's data (from games, EEG, sensors, etc.) will be sent to the cloud system:

a. A quality control is applied in order to determine if all data is available as expected. If data is valid (noise, outliers etc.) then b. Data is cleaned and organized by applying to each data the respective pipeline for pre-processing, de-noising, feature extraction.

c. All valid and pre-processed data will then be classified (see following section for details).

All data sent and stored in the cloud platform will be stored anonymously. No personal identifying information will be stored and patients will be assigned a numeric-alpha patient identifier code. In addition the cloud platform will include a set of visualization tools such as interactive charts and plots of the evolution of the monitored data over time to provide a greater amount of information to the LEAPS Reps and other PIs in the project. This will provide a comprehensive overview of the data through its different stages.

Mint Labs will develop the LEAPS app, the centralized app that provides the communication between the patients' (and its data) to the cloud platform (and the Representative). The LEAPS app will:

1. Provide tutorials, instructions, and weekly reminders to play the games
2. Collect the recorded data and send it to the cloud platform
3. Receive messages and emails from the Representative
4. See progress scores, and other engaging data from other users in the study.

Behavioral Media Networks (BMN) and Mint Labs will develop a series of data collection tasks that will collect cognitive and movement data as a game platform. Games will be designed similar to current popular apps such as Luminosity (Hardy and Scanlon, 2009). Data analysis in Specific Aim 2 will use algorithms to extract ToDM from data collected during game playing. For example spatial and non-spatial functional memory tasks, often used with MRI/fMRI imaging, will be analyzed for cognitive changes and performance over time, visual and auditory stroop tasks (such as say the color of the word, instead of the word that is written) to measure attentional and cognitive load, and games such as startling stimuli or visual cues will be used to measure hyperarousal. See FIGS. 11& 12 for mock up examples of the LEAPS App. As the program is developed we will conduct several usability tests in order to ensure straightforwardness and clarity. The App and the LEAPS sensors will undergo several iterations of testing to guarantee accuracy and integration between sensors, LEAP App, and cloud storage. Mint Labs provides a platform that facilitates advanced medical imaging analysis and visualization, data management and collaboration through a cloud platform supporting unlimited storage and computational resources.

Figure 11:
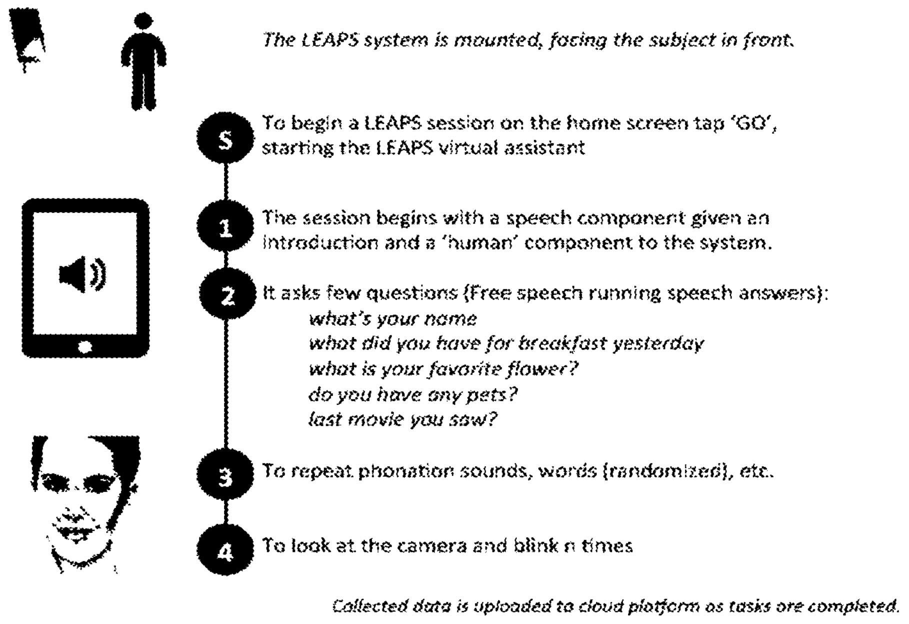
FIG. 11 shows a mockup of a LEAPS app for smart phones and tablets.
Figure 12:
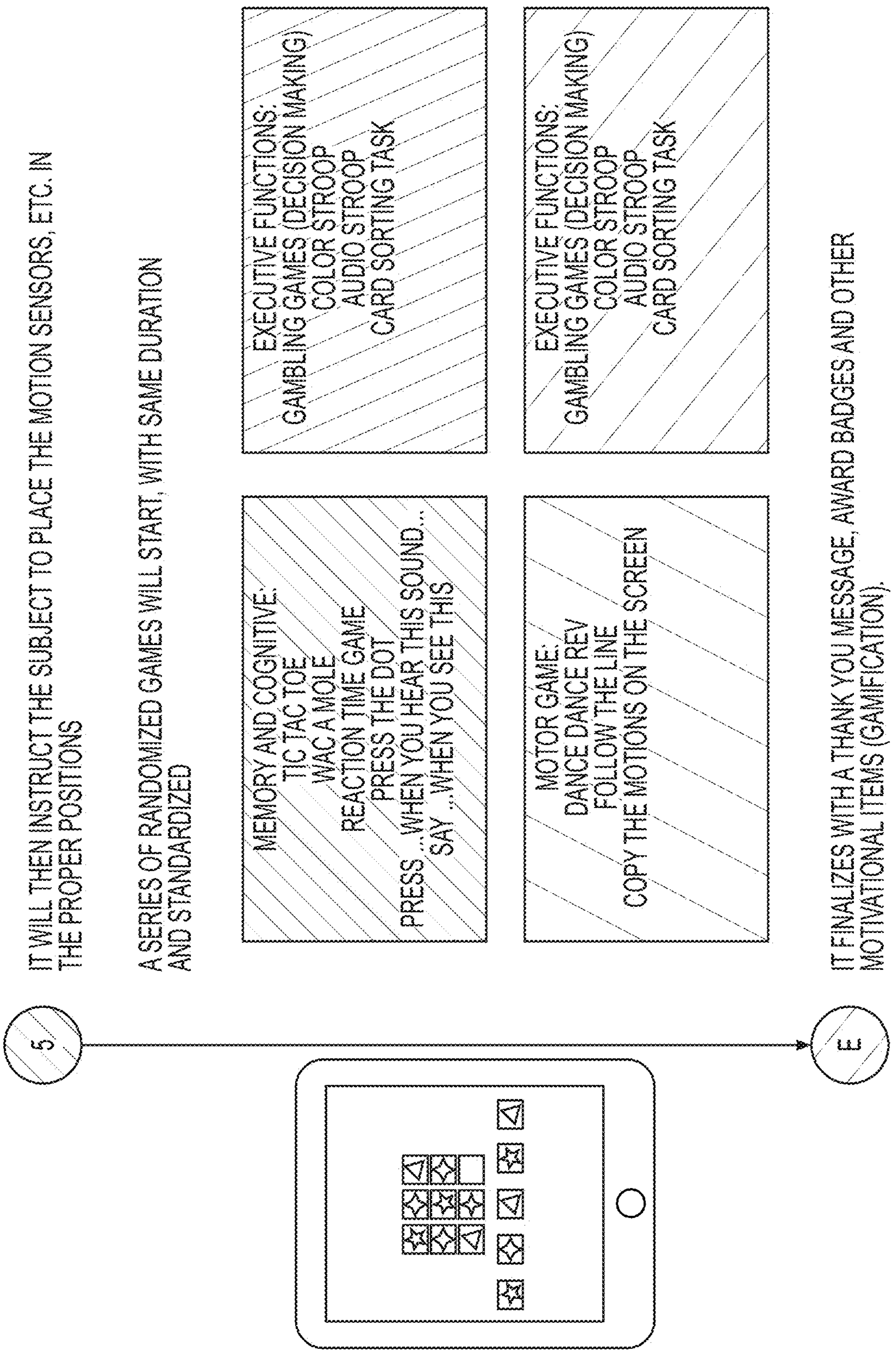
FIG. 12 shows a mockup of a LEAPS app for smart phones and tablets.

FIG. 11 shows a Mockup of a LEAPS app for smart phones and tablets. FIG. 12 shows a mockup of a LEAPS app for smart phones and tablets.

To maintain consistent data collection the app will send alerts when it is time to login, if the patient does not login when prompted, automated emails and text messages will be sent. If there is no response after $1^{st}$, $2^{nd}$, and $3^{rd}$ notifications the LEAPS Representative will personally phone them.

Establish LEAPS methodologies and quality control at 4 major trauma centers.

The consortium has access to four trauma locations, emergency rooms in French Islands, Oxford, UK, and Buffalo NY. Prior to data collection, the data collection committee will finalize the standards and protocols for collecting data. Two well-qualified postdocs with a background in clinical trials will be hired at each trauma center as designated "LEAPS Leaders". The LEAPS leaders will be responsible for all aspects of "hands on" data collection and project management at each center. They will manage coordination and communication between patients, investigators, PIs, and hospital personnel. They will work with the staff of each trauma center to smoothly integrate and 'embed' our data collection into their clinical routine with little disruption of routine clinical operations. LEAPS leaders will be in charge of securing the IRB and Ethics approval from each center, while initiating patient recruitment in real time when an eligible patient has been admitted (including obtained written consent, patient training on app use. setting up their profile using basic information and series of questionnaires, including the self-report PTSD checklist). LEAPS leaders will be in charge of ensuring weekly data deposits from patients. Patients will only meet with LEAPS Leaders in person a couple times, primarily all communication and data collection will be remote. Collect 3+ years of weekly data deposits for 2000+ patients.

Specific Aim 2: Analyze & Classify

Analysis of the data will begin as soon as data collection begins, and will continue throughout the entire collection phase. These disparate data streams beg an important question: how do we extract valuable observations from these streams? Because none of the data streams can provide a complete picture of post trauma responses by themselves, it is important to use a method that allows each to compensate for the others' shortcomings. Data analysis methods that fail to take into account physiological parameters will be limited in producing new insights. The same applies to over-fitting physiological parameters into data processing models. Therefore, we developed statistical analyses, continuous wavelet transform (CWT), and machine learning algorithms to analyze the data.

The app and sensors will wirelessly send information to the "LEAPS Server", where data will go through several phases of data verification, cleaning, labeling, storing, parsing, analyzing, and classifying. The sensors and app will communicate directly with the server. All data will automatically be stored in a secure cloud storage platform. As soon as patient profiles are created, all personal information will be anonymized and only accessible to the LEAPS leaders in password protected archive records. Every week the patients will be asked to log into the app and complete a session of tasks. When a patient completes a session, the data in its raw form will be stored in the cloud. The data will then be verified by machine learning classifiers. If the deposit is too noisy or collected incorrectly etc. it will be flagged for review.

The LEAPS analysis system will use existing BCCS codes and algorithms to train classifiers. The analysis and classification will be based on BCCS framework by extracting each data stream, performing interdependent time series analysis on each. To demonstrate the effectiveness of measuring intelligent action data streams to detect disease biomarkers, an example of Brain Code analysis is given below. It depicts brain code analysis on hand movements recorded from a body sensor. It takes into account the position of the hand, but the analysis is also extended to also include velocity and force as measured by the Golgi tendon organ and muscle spindle sensors. The plot on the left shows the position trace of the hand in X-direction over time. The line shows the measured position with an additional 95% confidence interval (CI) interval. A similar trace can also be obtained for Y and Z proving the information across all three dimensions (X,Y,Z). Only the current position is known with minimum error ($X_N$, $Y_N$, $Z_N$). The previous positions can be recalled but the further we go back in time the less we will be sure about the exact position that was obtained ($X_{i:N-1}$, $Y_{i:N-1}$, $Z_{i:N-1}$). It is likely that the system will rely less on this memory recall, hence the assignment of a weighing factor. On the other hand the task has probably been previously performed, as it is a common behavior in everyday life. The system can therefore rely on previous knowledge to predict the future of the movement ($X_{N+1:E}$, $Y_{N+1:E}$, $Z_{N+1:E}$). The output itself can also be used and is defined as position that arises based on the information available at the current state with a certain delay ($X_{N+D}$, $Y_{N+D}$, $Z_{N+D}$). This information can be used to extract features and determine the probability of a certain cognitive performance/function based on those features. The predicted cognitive performance can be fused with those obtained from other relevant parameters, e.g. speech. The final outcome can be compared with a clinically relevant cognitive scoring on a particular task.

Figure 13:
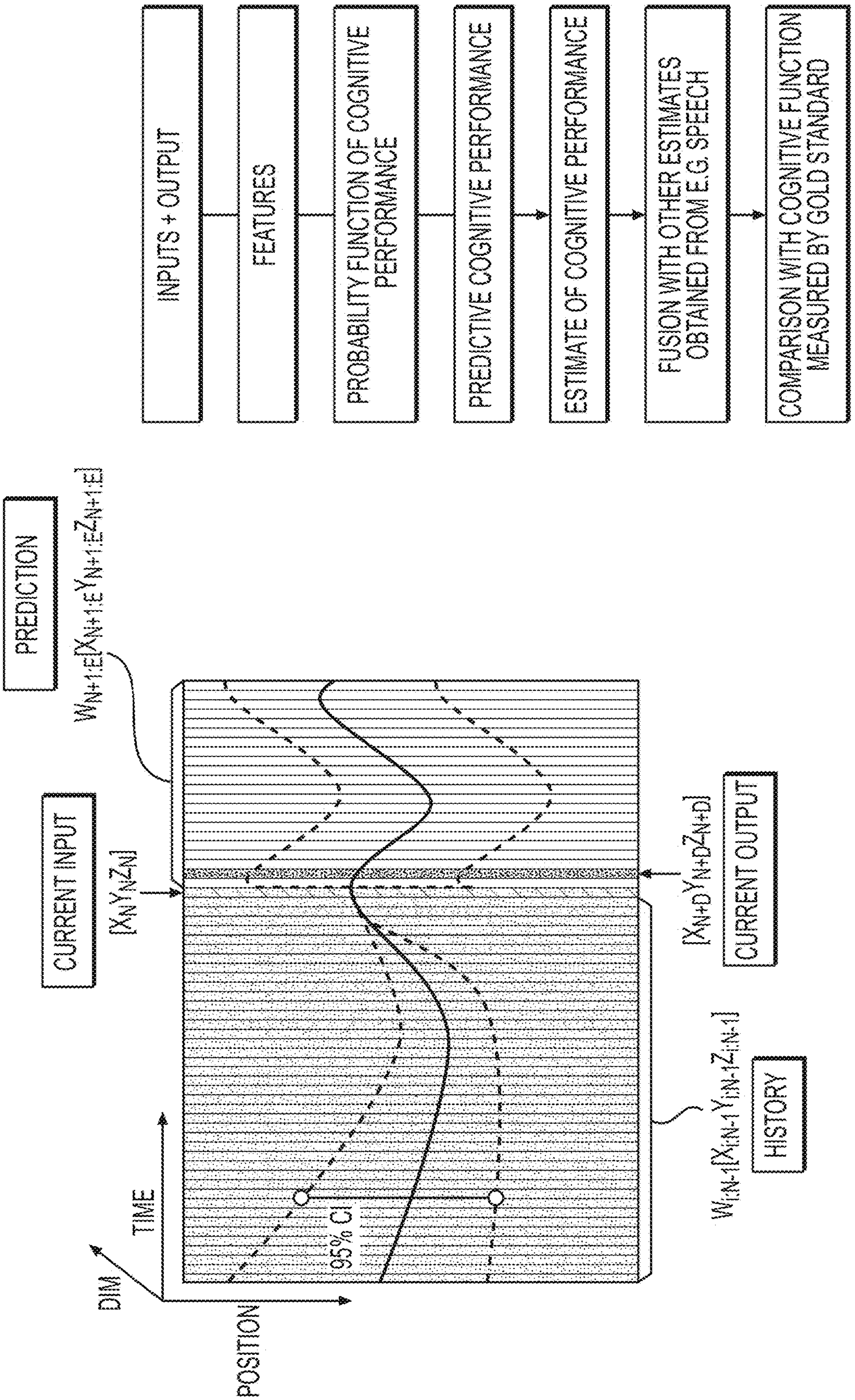
FIG. 13 illustrates a process for LEAPS analysis.

FIG. 13 illustrates a process for LEAPS analysis. The analysis will consist of several phases starting with individual data streams at a high level to determine the most promising metrics.

The analysis will be conducted in the following phases:

Phase I: Basic Statistical analysis, each ToDM separately

Phase II: Identify ToDM correlates and relationships

Phase III: Identify Biomarkers of interest (BOI)

Phase IV: Identify Subgroups of interest (SOI)

Phase V: Classify phenotypes

Phase VI: Identify Targets of Intervention (TFI)

Speech and Language Analysis

Recorded speech data will be parsed through several different linguistic analysis classifiers/axiological classifiers including SENTIC and LXIO (Cambria and Howard, 2013; Cambria et al., 2011; Cambria and Hussain, 2012; Cambria et al., 2010; Cambria et al., 2013; Cambria et al., 2012; Howard; Howard, 2012h; Howard, 2014; Howard and Guidere, 2011; Poria et al., 2012). A microphone and audio capture system will collect language and speech data, which will be analyzed using several linguistic computational algorithms to extract measures of mind state, affect, cognitive impairments and vocal deficiencies. In addition to linguistic analysis LEAP will also collect 30-second vowel phonations such as "aaaaaahhhh . . . ". Speech processing algorithms previously used for Parkinson's data (Tsanas et al., 2010; Tsanas et al., 2011; Tsanas et al., 2012) will be used to extract 16 dysphonia features (described in table 7). Measures include variation of fundamental frequency (jitter), several measures of amplitude (shimmer), noise to harmonics ratio (NHR), harmonics to noise ratio (HNR), detrended fluctuation analysis (DFA), and pitch period entropy (PPE).

Table 7 shows Dysphonia features:

| | Variable ratio | Description |
|---|---|---|
| 1 | Jitter (relative) | If we picture human voice patterns as a waveform with respect to time, then high variation in jitter, or fundamental frequency, means that the lowest frequency per unit time is in flux, suggesting a change in tone of voice, or inability to control voice tone |
| 2 | Jitter (absolute) | |
| 3 | Jitter:RAP | |
| 4 | Jitter:PPQ5 | |
| 5 | Jitter:DDP | |
| 6 | Shimmer | High value for the shimmer variable, which represents the amplitude ranging from the fundamental frequency to local peaks, also indicates lack of normal voice modulation |
| 7 | Shimmer (dB) | |
| 8 | Shimmer: APQ3 | |
| 9 | Shimmer: APQ5 | |
| 10 | Shimmer: APQ11 | |
| 11 | Shimmer: DDA | |
| 12 | NHR | NHR and HNR measure the ratio of noise to tonal components. |
| 13 | HNR | |
| 14 | RPDE | DFA is a Signal fractal scaling exponent (DFA) |
| 15 | DFA | |
| 16 | PPE | PPE is a nonlinear measure of fundamental frequency variation, similar to jitter. |

Facial Feature Analysis

Face processing is a very active area of research in computer vision and machine learning with entire conferences (e.g., IEEE Face & Gesture) dedicated to this topic. It has wide ranging applications and his perhaps the most mature area of research in computer vision. Automated face detection is now included in consumer-grade cameras (for automated adjustment of image exposure) and face recognition algorithms are routinely incorporated in photo library software (e.g., Google Picassa, Apple iPhoto, etc.). Recently, an algorithm for the analysis of facial movement (similar to the approach developed by Serre et al for automated analysis of rodent behaviors) was shown to outperform human subjects in detecting deceptive pain expressions (Bartlett et al., 2014).

Our validated two-stage emotion classifier SENTIC exhibits 97.25% accuracy on an eNTERFACE open source dataset. The classifier was developed based on Ekman's six emotion categories (fear, sadness, joy, disgust, surprise, and anger) plus an extra category 'neutral,' i.e. showing null/void emotion (Ekman, 1992; Ekman, 1993; Ekman and Rosenberg, 1997). A Cohn-Kanade AU-Coded Expression Database (CK++) was used to train the classifier to automatically classify facial expressions at time T to a definite and discrete emotion category (Pantic and Rothkrantz, 2000). Starting from time T0 to time Tn, there were n facial images for each subject. Suppose, at time T0 the subject started to express emotions in front of the camera until time Tn; within the period Tn−T0, there is a set of facial images that forms a sequence. Here, Ti denotes a time unit, and for each time unit Ti, there is a corresponding facial image of the subject. In the CK++ dataset, we found that at time TO (sometimes at T0, T1, T2) the subject expressed a void/null emotion, but at time Tk given that Tk≤Tn, Tk>0 the subject expressed an emotion e for the first time, which continued until the end of the time frame. Therefore, there is a transition of emotion (from void emotion to emotion e) between time Tl to time T (l+1). This feature of the dataset motivated us to clean the facial image sequences in order to obtain an optimal set of facial images of that subject expressing a particular emotion. We manually cleaned the facial image sequence into two categories: images expressing void/null emotion and images expressing a clear emotion (e). We classified a few initial image frames to null/void emotion, and the rest of the images in the sequence were classified to an emotion e according to the annotation in the CK++ dataset for that sequence. As an example of the cleaning process, suppose a sequence had 14 facial image frames among which the first two image frames expressed neutral emotion and the remaining 12 image frames expressed a surprise emotion. We included the two 'neutral emotion' images as null/void and the remaining 12 images were included as 'surprise emotion.' Consequently, we formed a large dataset of 5877 facial images. To classify the facial images we use a 2-step classifier—in the very first step, our classifier determines whether the image illustrated a null/void emotion or one of Ekman's six emotion categories. If the result is not classified as null/void, a 6-way classification is carried out on the image to identify the emotion category of the image otherwise it is declared that the image carries void/null emotion. On 2 open source datasets 97.25% accuracy was obtained using 2 stage, 7-way classification, which suggests that the classifier is neither biased towards a particular dataset nor over-fitted, but can be scalable.

Feature Extraction

To extract facial feature characteristic points (FCPs) we use a face recognition software called Luxland FSDK 1.7. Luxland extracts 62 facial characteristic points from an image of a face and compares it to a master database. As some studies suggest (Breukelaar and Back, 2005; Kulkami et al., 2009) distance-based measures of FCPs may be useful to classify emotion from facial expression. Measures include the distance between the right eye and the left eye (D(0,1)), the distance between the upper and lower lines of the left and right eyes (D(35,38), D(40,41)), and the distance between the inner and outer corners of left and right eyebrows (D(12,13), D(14,15)) (Poria et al., 2014f). If possible portable eye tracker glasses such as, mobile Eye-XG, Tobii, or Sensomotoric Instruments, will be used for blink rate, pupil measurements and other eye measurements. If portable eye tracker glasses are not included with the LEAPS device, video capture via the tablet can measure blink rate using the statistical analysis tool ANOVA, blink rate is calculated by the number of times the irises cannot be identified using the facial expression recognition program in 10-sec intervals. Eye tremor can also be measured based on the movements of the facial points of the eyes. Using the amplitude of eye tremor in each frame of the video stream of a subject we can compute an eye tremor signal from a simple power analysis. Eye movement direction can be quantified using the FCPs around both eyes. Serre Labs is planning to extend the original approach with an additional set of features derived from a computational model, which mimics the anatomy and physiology of the visual cortex and was shown to reproduce many electrophysiological data pertaining to the recognition of biological movements (Serre & Giese, 2010). A hallmark of this model is the combination of both static form information (as done in the existing system) with motion information, which has been shown to yield significantly higher levels of accuracy (Bartlett et al., 2014; Kuehne et al.).

Specific Aim 3: Predict & Share

At the end of the five years we want to have potential biomarkers of interest (BOIs), several models of trajectories and prediction algorithms for specified phenotypes, potential targets of intervention (TOIs) and a fully planned second phase/clinical study.

a) Predict patient trajectories
b) Model trajectories
c) Test risk prediction algorithms
d) Design target development studies
e) Design neuromodulation study
f) Make data available to science community and publish results Target Development Studies Based on longitudinal data we will identify biomarkers of interest (BOI) to test predictive risk algorithms and targets of intervention (TOI) for treatment or assessment of intervention.

We will plan target development studies with external experts. Select patients of interest will be asked to continue in the future study and recruitment of new subjects will be initiated, particularly healthy age matched controls to existing cohort. Testing and validation of these predictive algorithms will depend largely on the establishment of cognitive and physiological baselines, or significant samples of "normal" behavior, so that detection of the earliest trauma responses is possible.

We hypothesize that target development studies will include at least 2 potential biomarker groups and at least 2 targets of intervention groups, one of which will be non-invasive neuromodulation therapy. Serre labs is interested in developing a Kinnect in home target development study[15] with selected patient groups of 8-30.

Neuromodulation Study

Mr. Tipu Aziz from University of Oxford and Dr. Mascha Vant Wout from Brown University will be consulted as neuromodulation experts to plan a TDCS study dependent on the TOIs identified in years 1-4.

Share

Eventually we will invite the research field and clinical community to facilitate analysis beyond the scope of this project and combine with existing research. Make data (raw and analyzed) available to science community on a PTSD database or through NIH and produce open access publications on our observations and results. Table 8 shows a proposed statement of work:

| Month | Task/Milestone | People |
|---|---|---|
| AIM 1 (1-24) | COLLECT | Trauma Committee |
| 1-3 | Finalize ToDM | |
| 1-2 | Inclusion/Exclusion criteria | Trauma Committee & Data Collection Committee |
| 3 | Checkpoint: Center site visits, Patient projections | Steering & Quality Committee |
| 1-5 | Finalize Sensors to be included | Tech & Software Committee |
| 1-3 | Finalize content for app: questionnaire and game/tasks for each ToDM | Trauma Committee & Tech Committee |
| 2-4 | Phase I Hardware Integration (BSN, EKG, EEG, headphones, mic etc.) "Build LEAPS Device" | Tech Committee |
| 3-5 | Develop App for iPhone & android | Tech Committee |
| 3-5 | Cloud platform & storage development | Tech Committee |
| 5-6 | Phase II hardware and app integration | Tech committee & Data Collection Committee |
| 5-9 | Upload BCCS codes, algorithms, train classifiers | Analysis Committee |
| 6 | Checkpoint | Steering & Quality Committee |
| 6-8 | Phase III Troubleshooting | Tech Committee |
| 9-11 | Start mass production of LEAPS devices (100/week) Serre Lab | Tech Committee |
| 9 | Checkpoint | Steering & Quality Committee |
| 12-24 | Recruit 2,000 patients (166/month) collect weekly | Data Collection Committee |
| 12 | Checkpoint | |
| AIM 2(12-36) | ANALYZE & CLASSIFY | |
| 12-18 | Phase I: Basic Statistical Analysis | Data Analysis Committee |
| 14-24 | Phase II: Correlates and relationships | Data Analysis Committee & Trauma Committee |
| 15 | Checkpoint | |
| 20-36 | Phase III: Identify Biomarkers of Interest (BOI) | Data Analysis Committee |
| 20-36 | Phase IV: Identify subgroups of interest (SOI) | Data Analysis Committee |
| 18 | Checkpoint | Steering & Quality Committee |
| 21 | Checkpoint | Steering & Quality Committee |
| 24-36 | Phase V classify phenotypes | Data Analysis Committee & Trauma Committee |
| 24-36 | Phase VI Identify targets of intervention | Data Analysis Committee & Future studies committee |
| 24 | Checkpoint | |
| AIM 3 (36-60) | PREDICT & SHARE | Steering & Quality |
| 27 | Checkpoint | Committee |
| 30 | Checkpoint | Steering & Quality Committee |
| 33 | Checkpoint | Steering & Quality Committee |
| 36-60 | Test prediction algorithms on remaining data | Data Analysis Committee & Trauma Committee & Future studies |
| 36-60 | Test Biomarkers on remaining data | |
| 42-60 | Plan Target Development studies | Future studies Committee |
| 36 | Checkpoint | Steering & Quality Committee |
| 48-60 | Create Open Access PTSD Database & publications | Publishing committee |
| 60 | FINAL Checkpoint | Steering & Quality Committee |

Section Seven: Conclusion

PTSD has recently been reclassified into a new category of psychiatric disorders. The problem with diagnosis is only a small portion of the acute trauma symptoms allow for accurate prediction of the development of chronic PTSD. Present diagnostic tools are based on self-report tests and face-to-face evaluation. There are numerous comorbid diseases that mask PTSD and some of these comorbidities complicate clinical aspects of PTSD. The basis for our proposal is from understanding that traumatic events that cause PTSD tend to alter brain networks, emotion and sensory input and motor output among other characteristics.

We address the factor of resiliency as related to PTSD and how the way in which a patient responds to a traumatic event is impacted by PTSD progression. Resiliency and how people respond to traumatic events can also be impacted by pre-existing factors such as IQ, biological social and genetic factors. Importantly related to the progression of PTSD is the difference between acute and chronic PTSD. Because many of the symptoms don't always appear initially it makes it very difficult to diagnose acute patients that will progress into a chronic PTSD diagnosis. Another concern with diagnosis is the problem of comorbidities that increase the chance of misdiagnosis. Along with these comorbid diagnoses, Valderas et al. (2009) says it is also associated with worse health outcomes, difficult clinical management, and increased health costs.

There are a variety of biomarkers that are known to be prevalent in PTSD however they haven't yet been utilized for diagnosis. These consist of genetic predictors, heart rate, hypothalamic-pituitary-adrenal (HPA) axis, hippocampal volume, and lifestyle. However current diagnostic assessments remain limited in scope. They are brief and many are self-reporting. They require a clinician face-to-face interaction and use few points of information to pinpoint the traumatic event. Although these diagnostic tools are only useful once the trauma has already been established. Once diagnosis of PTSD has been made, a significant portion of management methods become a pharmaceutical blanket that can subsequently lead to more problems and more disorders.

The Brain Code Collection System (BCCS) is a way to quantify the link between input and output to segregate specific biomarkers. The goal is to non-invasively collect multi-level data, integrate multi data streams, and apply multi-level paradigm analyses using these previously established theories. Though successful for Parkinson's disease, BCCS for PTSD will use data streams Target of Dimensional Measure (ToDM) that represent the brain output. These ToDMs will eventually be utilized in the final Longitudinal Evaluation of Adult Post-Traumatic Syndromes consortium (LEAPS) to create a holistic non-invasive way to characterize posttraumatic course.

Our suggested development of the LEAPS study by developing a machine to interact with the brain a thorough understanding cognition particularly aspects of perception, prediction and speech and language is required. Perception has typically been fundamental to diagnosis of neurological disorders because it exposes the patient's experience through the self-reports currently used in diagnosis. Perception is also an accumulation of several sensory inputs. Morris et al.'s research indicates that perception comes from pre-existing neural patterns and new combinations of neural activity. These unconscious processes according to Quasaibaty et al. (2004) can be organized into a "hierarchy of basic conscious components" (Quasaibaty et al. 2004). There have been successful uses of systems that incorporate this situational awareness particularly with high volumes of data. Intention awareness systems must copy aspects of human cognition in order to present intention awareness to the analyst. When there is a lack of information to make a conclusion, humans extrapolate to fill in information. The second is prioritizing when there is too much information. Because the nature of intention awareness often comes from imperfect environments, systems can never create flawless results only approach them. Intention is significant in neurological disorders because it in itself predicts actions based on the idea that actions are guided by the desire for a specific outcome. Mathematical modeling can help predict these outcomes. Intentionality also incorporates the notion of time. This can also tell us a great deal about neurological disorder.

We discuss the importance of speech and language and how it can be a basis for detection. Within language there are linguistic primes that exist at the word and sub-word level. Because PTSD signs is restricted to the hippocampal region, in order to differentiate between the other comorbid diseases studying natural language could be a way to interact with the brain without using an invasive process. Papangelic et al. (2013) has developed a system that performs the assessment on natural language and is recurrently modifying diagnosis with the new information. Although their developed system engages the patient in conversation and subsequently develops vectors off of the dialogue to produce a data set, it lacks the incorporation of visual and audiovisual inputs, which are important for PTSD diagnosis. Linguistic analysis using MSI and LXIO is an important aspect of the BCCS and the proposed LEAPS study. It assigns positive and negative values to words and concepts based on their context and connotations. The LXIO engine breaks each sentence down into words and creates data for these phrases within a specific timeframe. The axiology of LXIO is used to map words to feelings and to predict cognitive states based on the use of language.

Understanding the Brain Code (BC) is essential to grasping an understanding of the BCCS and LEAPS Project. Essentially the BC is a higher-level analysis that incorporates several inputs to produce a cognitive output. The Fundamental Code Unit (FCU) codes this cognitive output. First aspect of FCU is the transmission of information once the threshold of the neuron is reached. Duration combined with threshold crossing may define selection mechanism. The third is transfer of information and processing relies on energy and the fourth is the human sensing system, which serves as a transducer between different forms of energy. The Brain Code combines cognitive events such as neural spikes, network activation, and memory recall. The BC is decoded to a combination of inputs (natural language, behavioral outputs, and electrical activities of the brain), which yields the cognitive output. The combination of these inputs is mentioned because in order to ensure a comprehensive analysis of PTSD, it's important to not just analyze one of these inputs, rather the holistic picture. We have suggested the analysis of neural oscillations, linguistics, and behavior combined is essentially the basis of the Brain Code. A main objective of the BC development is learning how each of these individual data streams relates to one another.

The motivation for developing the FCU framework was influenced by Marx and Gilon's method, which takes a three-part model of memory engrams and focuses on individual neurons, neural neurons, extracellular matrices, and chemicals that affect the activity. Beyond this was the argument that there exists an energy paradox in the brain. We argue that energy constraints are governed by optimal coding principles. The Brain Code itself requires an accurate and relevant energy efficient descriptions. The purpose it to consider many of these factors but bridge the gap between cognitive outputs and biological, chemical, and physical sources of these processes.

The Brain Code Collection System (BCCS) involves non-invasive data collection while combining multiple data streams and finally applying a multi-level analysis. The BCCS collects stream of broken data and aims to quantify this data and link input to output. Target of Dimensional Measure (ToDM) is a stream of multi-level data and each ToDM represents brain output. A combination of these ToDMs can be collected to be utilized in the LEAPS study.

One of the most hallmark symptoms is the inability to turn off conditioned fear. Although cognitive behavioral therapy (CBT) using exposure treatment has some benefits majority of PTSD patients treated with this method still have residual symptoms. The inability to limit this fear response is shown in the dACC area which appears to be over-active while the vmPFC which inhibits fear tends to be smaller in volume and less activated in PTSD patients. Our proposed idea of frequent measuring of heart rate and electrodermal area may give insight as to the probability of someone developing PTSD and also the effectiveness of the CBT therapy. As a part of the LEAPS system, understanding that neural oscillations hold potential for evaluation of brain disorders. EEG and MEG measurements can examine these neural oscillations to assess another potential biomarker. With the establishment of biomarkers the question now becomes the calculation of how these biomarkers will be measured and algorithms calculated. The proposal for the BCCS combines methods that have been applied for the past decade to evolve into the methodology to detect PTSD.

Analysis of social media Dodds et al. (2011) classifies messages into positive and negative examples and can subsequently detect the levels of stress relaxation time etc. This is similar to the LXIO method in which an algorithm is used to detect positive or negative values in natural language. Understanding metaphors or lack thereof can be indicative of brain dysfunction. Using fMRI with patients of schizophrenia it is shown there is an inability to utilize the brain regions crucial for processing these metaphors. Metaphor processing requires activation of certain areas of the brain associated with abstract comprehension.

Multilayered Perceptron Neural Networks (MLPNNs) utilized by Sagiroglu et al. (2007) are a way of adding or removing weight for each input signal that matches the pre-trained lexical network. This helps determine whether the input matches a given language. The MLPNNs can be broken down into three layers of input output and a "hidden" layer.

In terms of machine learning there are important steps that are taken into consideration to create the most effective machine learning. The greater data the better grasp the machine will have which is a basic concept. However the machine seeks to minimize the overall size of the data payload to not lose on speed performance or efficiency. Translation step is done using pre-defined grammar rules and thirdly transformation rule such as patterns for determining structural differences in different languages must be applied. The machine must go through evolutionary training. In discussing the ideas put forth by Goguen (2006), Malouf (2002), Meehan (1977) and Madsen (2009) regarding language translation, the probabilistic perspective is beneficial because it is conducive to the development techniques that use multisensory sources. The lack of understanding a patient's state of mind led us to provide an assessment database of default values referred to as the Mind Default Axiology (MDA). This database assigns negative and positive values as well as matching word patterns using the pseudocode function. We construct the multilayered perception neural networks (MLPNNs) by adjusting for occurrence frequency of text in each language. Each of the calculations there is a mathematical basis for these theories and postulations. Using machine as a function of analyzing metaphor comprehension required the ability to extract meaning of metaphors as well as determining which metaphor connections be made by default. It also requires an understanding of cultural basis. Because this idea is significantly underdeveloped my goal is to expand on the research objectives and to investigate the phenomenon if metaphor recognition can be used to aid in the identification of neurodegenerative disorders.

Our model for the mind default axiology (MDA) is novel for the reason that we measure the observable phenomena that composes our emotional expression which is lacking in previous research on developing an analysis of mind state. Going further the resulting Mind State Indicator (MSI) can indicate a wider range of psychological phenomena than permissible with existing assessment tools. The MSI allows precise emotional states in time and space. The importance of LXIO lies in the ability to identify a patient's state of mind using an analyzer dependent on axiological values, time orientation, and inter-relation between words. To further increase accuracy of the mind state would require inclusion of facial and gesture analysis.

Understanding that gait and posture are an indicator and an important biomarker of PTSD we tested the body sensors network (BSN) by measuring differences in motor behavior in response to a changing environment. The BSN has previously demonstrated that wavelet analysis allows for differentiation between patients and healthy controls. To develop these BSN for everyday living the systems were tested for robustness in extreme environments. The results still showed indicative results even after being exposed to extreme environments. The next and final goal was to create sensors that don't interfere with everyday life and that could provide higher levels of conformity. Using the already developed integrated clothing sensing system (ICSS) as a wearable body sensory to measure movement patterns related to joint stability can detect different levels of stability.

We have additionally proposed a non-invasive way of recording local field potential (LFP) using EEG hardware to detect the pain biomarker. We suggest that it may be effective in detecting sensory abnormalities in PTSD patients as well as allowing us to segregate comorbid diseases related to the sensory disturbances. The NOD algorithm was effective in distinguishing pain and control subjects from using the EEG recordings by the observation of spindle bursts.

We know that facial expression indicates a lot about a person's mood state. A study completed tested a classifier and used facial feature points to analyze a Parkinson's disease patient. This previous research indicated the difference of eye movement in a Parkinson's disease patient and shows promises to benefit the research and detection of PTSD.

Using all of the significant research that has previously been used in various neurodegenerative diseases, we have proposed combining these and creating an all-inclusive measurable way of detecting PTSD. Our proposal begins with the collection of a large amount of raw data. We plan to deploy the LEAPS device as a way of non-invasively, collecting multi-level and multi-modal data using the BCCS system for multiple streams of ToDMs. In order to do this the BCCS requires refining. The BCCS will then train machine to collect process and store this large amount of data over a series of time. The next goal is the analyze these ToDMs to observe changes in cognitive behavior in relation to clinical function. We plan to identify effective biomarkers to assess the relationships between clinical phenotypes. Our final aim is to validate risk prediction based on the biomarkers and identify potential targets for intervention. We have established a variety of locations that are equipped to handle this kind of large scale data collection project.

The first generation of the project is referred to as the BCCS which will collect multiple data streams using non-invasive body sensors, and capture image and audio. It is intended for use at home and to be convenient and user friendly for the user. The second generation is the LEAPS device. It consists of the BCCS redefined to specifically target PTSD patients and contain a specific app that is an interactive tool to collect data. The LEAPS analysis uses the BCCS codes and algorithms to train classifiers. Unlike current evaluations that are being used, this app removes the need to face-to-face clinician involvement. Beyond the app, the LEAPS device will consist of upper limb sensors, lower limb sensors, EKG sensor, EEG electrodes, headphones, mic, and video recording. The games/tasks the patient is asked to complete will collect consistent data for each ToDM. The data collected will be related to specific biomarkers already established. The microphone and audio capture will collect language and speech data which will be reflected by the natural language processing analysis. Facial feature characterization will be classified using a face recognition software that measures a variety of values related to facial expression. This data will then be sent and stored in the cloud platform and stored anonymously.

In this paper we have proposed an innovative diagnostic tool that can enable a more effective way of diagnosing and treating patients with PTSD. Combined analysis of natural language processing, previous utilized diagnostic tools as well as brain code analysis from the BCCS can allow for complete streams of data to quantify input and output. The data produced from the BCCS to provide the basic foundation for LEAPS provides the needed precision methods as well as speed that is lacking in current diagnostic methods. The combination of multiple biomarker analysis leads towards a more comprehensive overview. The previous success of LEAPS used in Parkinson's patients allows for anticipated development towards a more successful PTSD diagnosis and management system. Developing a successful system for diagnostic tools could as a result aid in screening measures for susceptibility of developing PTSD.

Brain Code Multi-Modal Fusion Model Case Study

Understanding cortical computing is crucial for addressing several scientific and medical challenges such as the expected increase in the prevalence of neurodegenerative diseases. The growing understanding of brain-like computations suggests that at the strategic level this challenge should be addressed from a fresh perspective. A Brain Code Platform (BCP) has been proposed as an integrative environment for measuring brain activity. The BCP will focus on cheap and noninvasive measurement of brain-activity at (1) several complementary levels of analysis, in (2) naturalistic settings (3) by fusing brain related activities such as speech and movement and by (4) using novel mathematical tools for understanding these activities, fusing different measurements of the brain and brain-related activities, and using this information fusion for early warning signals for the outburst of neurodegenerative diseases. This platform is based on analysis of brain primitives through spontaneous patterns of activation. A growing understanding in the field of brain-like computations is the critical importance that a-priory information plays in the generation of computational primitives. We would like to review the growing evidence that such a-priory information is readily available for examination in the human brain—through the newly discovered phenomena of spontaneously emerging neuronal activity patterns. These patterns offer a unique window into in-built, a-priory information that plays a critical role in cortical networks on the one hand, and in allowing powerful and optimal computational processes that are inherent in human cognition. Such a-priory information has been amply recognized as playing a critical role in numerous cognitive functions—from perception to motor control (Arieli et al., 1996; Amal and Giraud, 2012; Barraclough et al., 2004; Boly et al., 2007; Busch et al., 2009; Chavan et al., 2013; de Lange et al., 2013; Drewes and VanRullen, 2011; Engel et al., 2001; Fiser et al., 2010; Fried et al., 2011; Hesselmann et al., 2008; Kayser et al., 2009; Kok et al., 2012; Köver and Bao, 2010; Ploner et al., 2010; Sadaghiani et al., 2010; SanMiguel et al., 2013; Schurger et al., 2012; Soon et al., 2008; Stefanics et al., 2010; Wang, 2008).

An important set of computational failures concerns cases where cognitive biases are distorted to such an extreme level that they lead to cortical mal-function. We argue that the resting state patterns should recapitulate the typical functional abnormalities encountered by patients suffering from brain pathologies. Although a large body of data is rapidly accumulating with regards to abnormalities of spontaneous patterns (SPs) associated with various brain pathologies—surprisingly few studies have attempted to directly compare task-related abnormalities with their corresponding SPs (Gilaie-Dotan et al., 2013; Liu et al., 2011; Watkins et al., 2012).

The BCP will allow us to measure the spontaneous patterns of subjects at different levels of analysis in a non-invasive way. The information gained through this measurement will be integrated with the measurement of speech and movement that have been found to be efficient indicators of pathologies in neurodegenerative disease (Aarsland et al., 2004; Aarsland et al., 2007; Aarsland et al., 1999; Bavelier et al., 2006; Bottini Bonfanti, 2013; Chaudhuri et al., 2006; de la Monte et al., 1989; Fahn, 2003; Howard et al., 2013f; Howard et al., 2013v; Hu et al., 2011; Jankovic, 2008; Riedel et al., 2008; Skodda et al., 2012; Starkstein et al., 1989; Tsanas et al., 2011; Tsanas et al., 2012; Wertman et al., 1993). Novel mathematical tools and methodologies, such as the affine invariance (Pham and Bennequin, 2012) and dynamic graph methods will be used to identify patterns in the data, pattern that through Machine Learning algorithms aim to predict the outburst of the neurodegenerative disease.

Here we review a cognitive load experiment, evaluating the effect of everyday living behavior on cognitive processing (Bergmann et al., 2015; Bergmann et al., 2013c). A spatial auditory Stroop task was used. The input signal consisted of a spatial signal (sound in left or right ear) with a sound ("Left" or "right"). After cognitive processing was assessed using the Stroop task a simple behavioral response was required depending on if the sound and spatial orientation matched or differed, by shaking the head. It has been shown that the planum temporale region is responsible for perceiving the location of sounds (Deouell et al., 2007). The neurons in this region represent, in a non-intentional or pre-attentive fashion, the location of sound sources in the environment. Space representation in this region may provide the neural substrate needed for an orientation response to critical auditory events and for linking auditory information with information acquired through other modalities. This indicates a neural basis that can be linked with the defined brain encoding for this example. A connection between different modalities has been shown between e.g. speech and vision (Blank et al., 2011). This link can be structural, but the brain code provides a more abstract approach. The concept relies on the well-known phenomenon of resonance (Spiegler et al., 2011). The resonance transfer of energy between molecules, or between sites within a large molecule, plays a central role in many areas of modern chemistry and physics (Andrews and Demidov, 1999). There is evidence that stochastic resonance within the human brain can enhance behavioral responses to weak sensory inputs (Kitajo et al., 2003).

Both speech and intended movement can be transformed to wavelets to provide a signal that can resonate (Howard et al., 2013m; Kronland-Martinet et al., 1987). The fundamental frequency of speech is roughly 50-210 Hz (Traunmüller and Eriksson, 1994) and for movement the relevant physiological range is 0.5-10 Hz (Barnes et al., 1978). Signals are normalized against those ranges generating a unitary pseudo frequency. The association between these modalities can be determined based on the coherence between wavelets from normalized signals. We performed a brain code analysis by extracting each of these data streams, performing interdependent time series analysis on each. The brain code concept is shown receiving input from an audio task and memory to generate a specific voluntary movement. A machine learning approach is currently used as placeholder for linking the different data streams. Once specific features start to emerge a unitary method will be introduced. This replacement of machine learning with unitary math provides a generalization across data streams, which allows for further direct linkage between modalities.

Examining the Brain Code Principles

A growing understanding in the field of brain-like computations is the critical importance of a-priory information in the generation of computational primitives. For example in (Lerner et al., 2008) a critical parameter in developing brain-inspired visual recognitions algorithm is the incorporation of a-priory information about informative vs. uninformative primitives of visual recognition. Such extensive information, which typically can be derived either through evolutionary processes or through daily experience, is available to the system a-priori—i.e. even before it interacts with the optical information. By embedding vast levels of such a-priory information in the computational primitives—the task of recognition systems becomes much more efficient and performance is greatly improved. The critical question that is still unclear is to what extent the human brain actually makes use of such information, whether it is acquired only during early development, and whether it extends throughout all cognitive processes.

Contrary to previous concepts—the incorporation of a-priory information is an extremely pervasive process, that occurs throughout all daily life, extends to all cognitive and neuronal aspects- and can explain both the outstanding computational capabilities of the human brain on the one hand, but also its devastation in various brain pathologies on the other. There is growing evidence that such a-priory information is readily available for examination in the human brain—through the newly discovered phenomena of spontaneously emerging neuronal activity patterns.

Spontaneously Emerging Spatiotemporal Neuronal Activity Patterns

Figure 14:
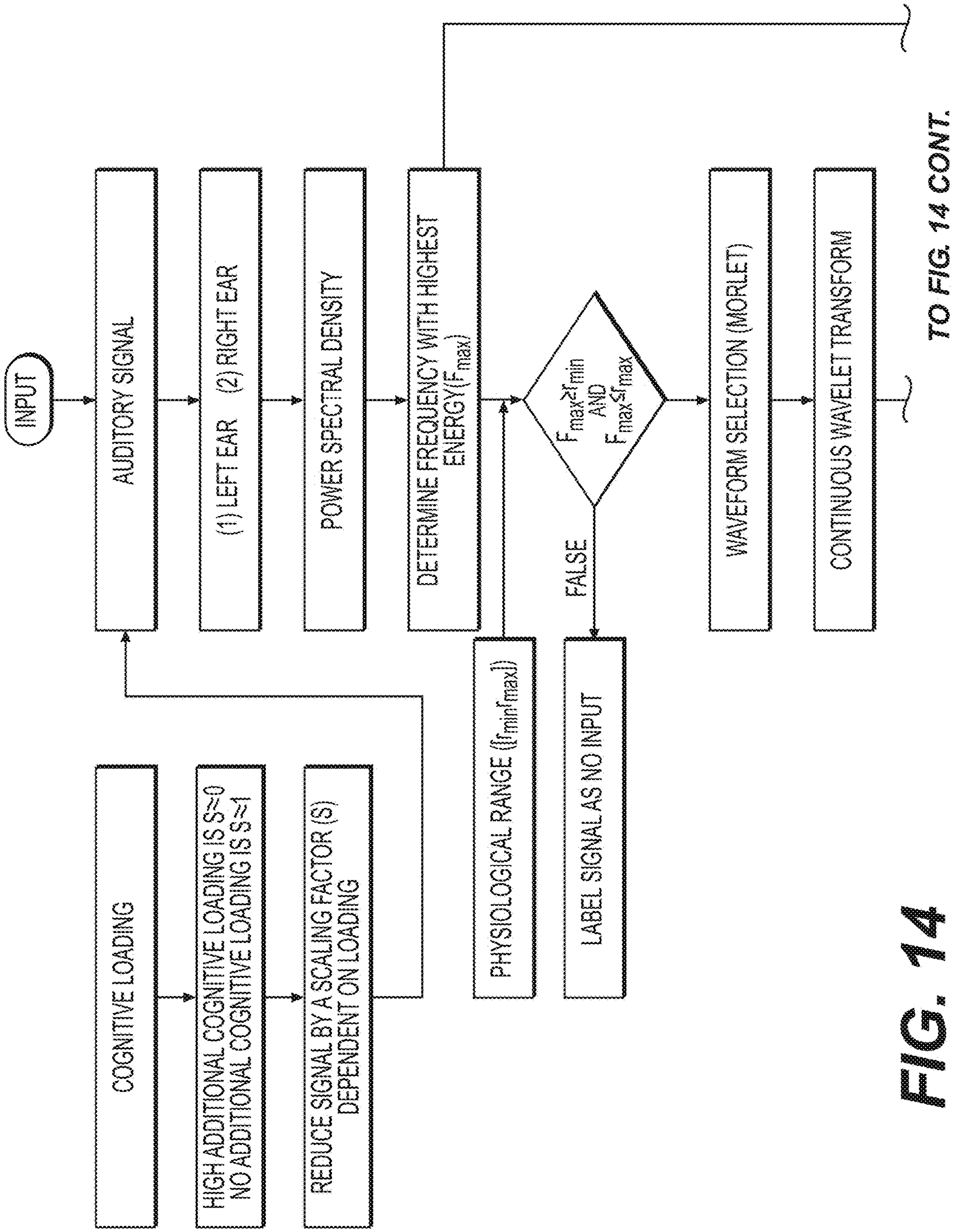
Figure 14:
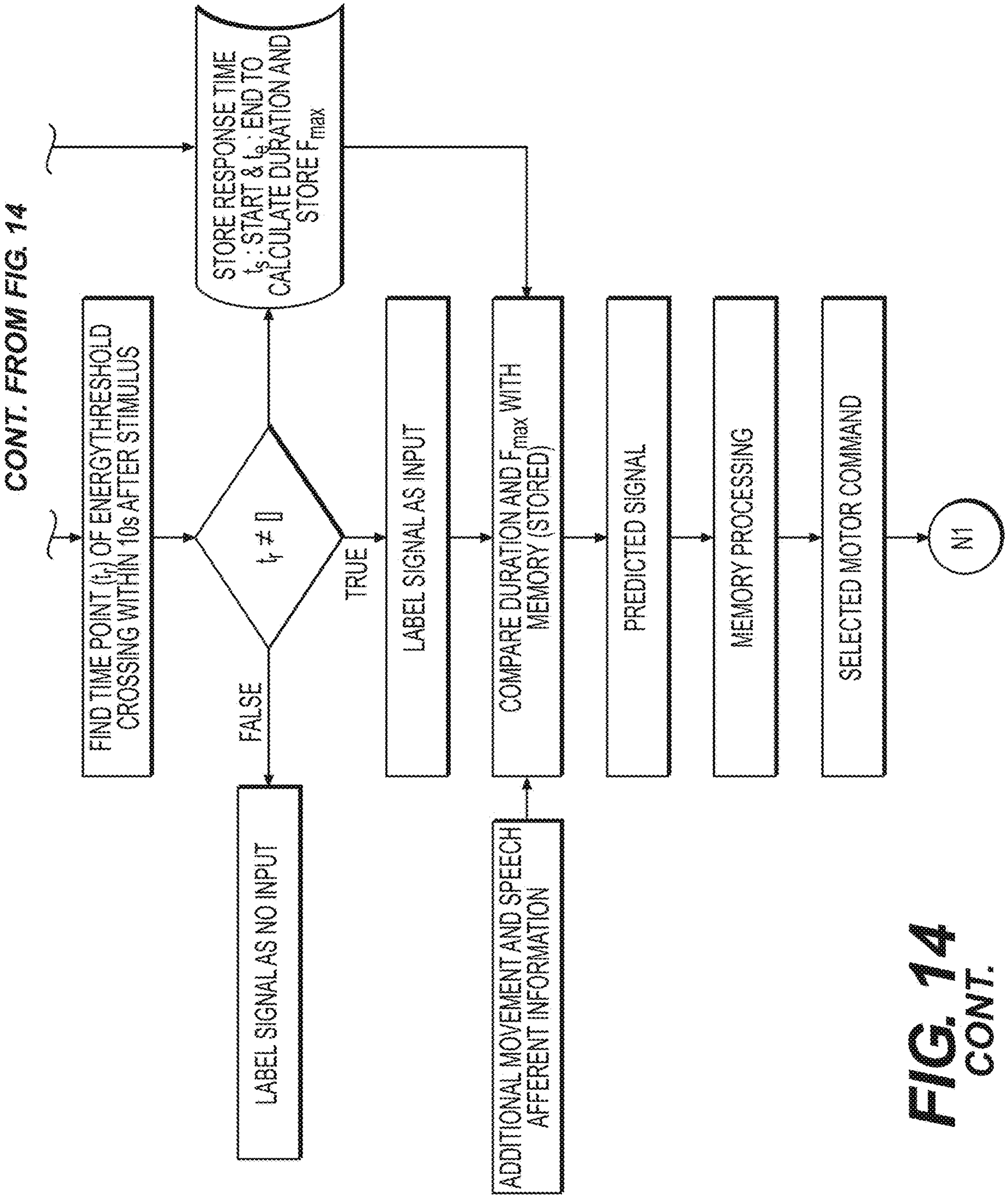
Figure 15:
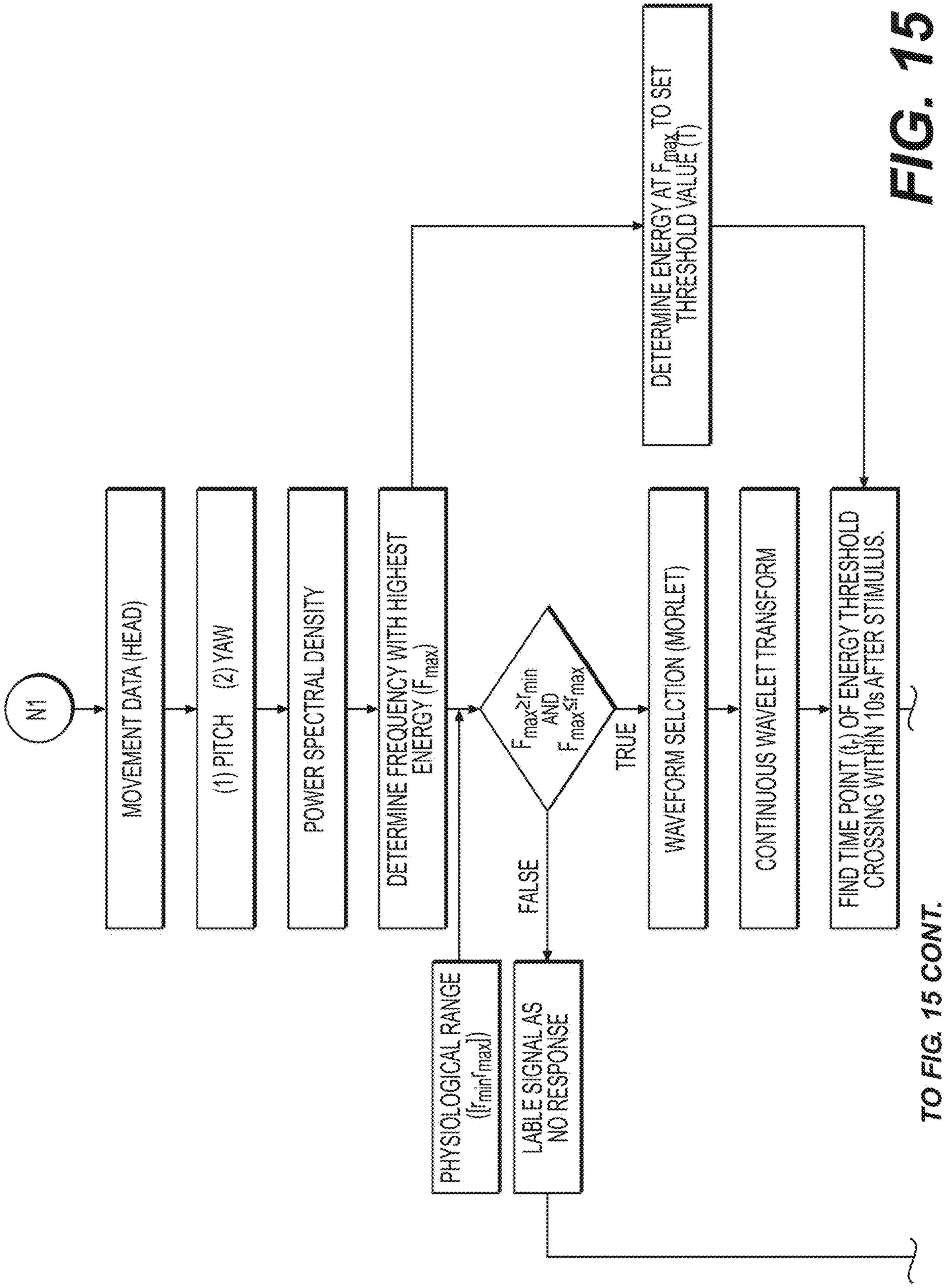
Figure 15:
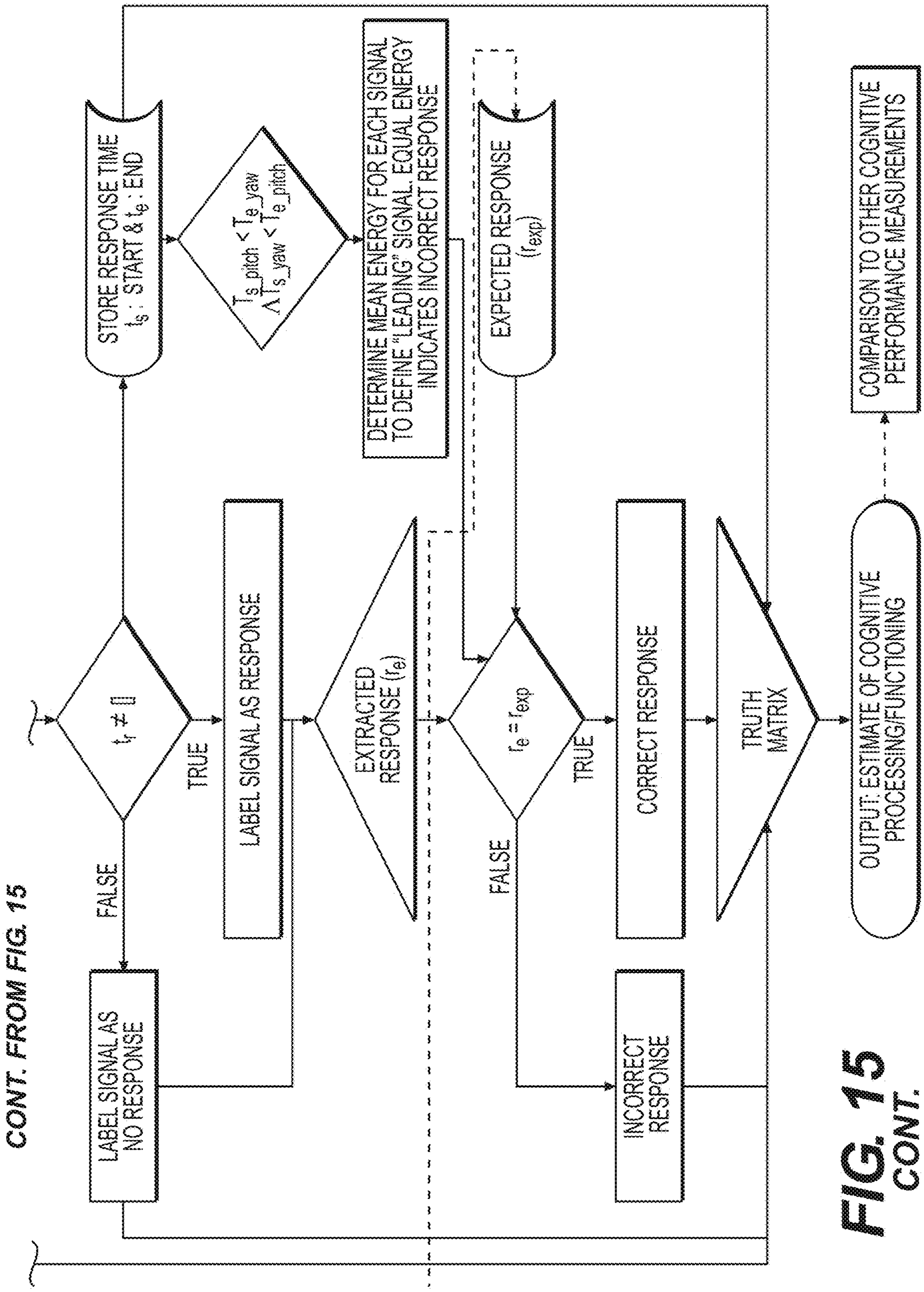

While traditionally most cognitive neuroscience research has focused on mapping the details of task-induced activation patterns, more recently it is becoming evident that highly informative activity goes on also in the absence of such overt tasks. FIG. 14 shows a diagram of a Brain Code algorithm for cognitive processing under task loaded conditions. FIG. 15 shows a diagram of a B rain Code algorithm for cognitive processing under task loaded conditions.

Thus, it is now becoming quite clear that even during rest the brain is active- and not in a random manner, but in a highly complex rich and robust pattern of activity (Nir et al., 2006). Furthermore, these activity patterns have now been documented not only in brain imaging but in single units and -LFP recordings as well (He et al., 2008; Manning et al., 2009; Nir et al., 2008a), showing ultra-slow dynamics (Nir et al., 2008b).

The functional role of these spontaneous (also termed "resting state") patterns remains elusive. However, regardless of their function we can ask—what can these patterns tell us about the underlying cortical function? I would like to propose here that these patterns offer a unique window into in-built, a-priory information that plays a critical role in cortical networks on the one hand, and in allowing powerful and optimal computational processes that are inherent in human cognition.

Since the pioneering work of Hebb (1949) it has been realized that such a-priory biases are embodied in the synaptic efficacies of synaptic connections in cortical networks. SPs uncover the underlying structure of synaptic connectivity in cortical networks and thus offer us a unique window into the a-priory information stored in the cortex. More generally—these a-priory tendencies are an essential component in determining individual traits and sensitivities in typical and individuals suffering from brain pathologies. Thus, the SPs may provide an important and unique window into deciphering such biases in individual brains. Such a-priory information has been amply recognized as playing a critical role in numerous cognitive functions—from perception to motor control (Arieli et al., 1996; Arnal and Giraud, 2012; Barraclough et al., 2004; Boly et al., 2007; Busch et al., 2009; Chavan et al., 2013; de Lange et al., 2013; Drewes and VanRullen, 2011; Engel et al., 2001; Fiser et al., 2010; Fried et al., 2011; Hesselmann et al., 2008; Kayser et al., 2009; Kok et al., 2012; Köver and Bao, 2010; Ploner et al., 2010; Sadaghiani et al., 2010; SanMiguel et al., 2013; Schurger et al., 2012; Soon et al., 2008; Stefanics et al., 2010; Wang, 2008).

A Toy Model of a-Priory Biases

Why should SPs reflect the cortical a-priory network biases? To illustrate how the hypothetical link comes about we will consider a highly simplified "toy" model (FIG. 3). We start by considering a simple feed-forward circuit, consisting of four V1-like "line detectors" that feed converging inputs into a target high order neuron. Following Hebbian learning we expect the training pattern to generate a corresponding modification of synaptic efficacies—essentially embedding a trace of the average co-activations in the network connections (red plus signs). Importantly, note that the restructuring of the connectivity strength of this simple circuit now endows it with a-priory sensitivity towards a triangle shape.

Figure 16:
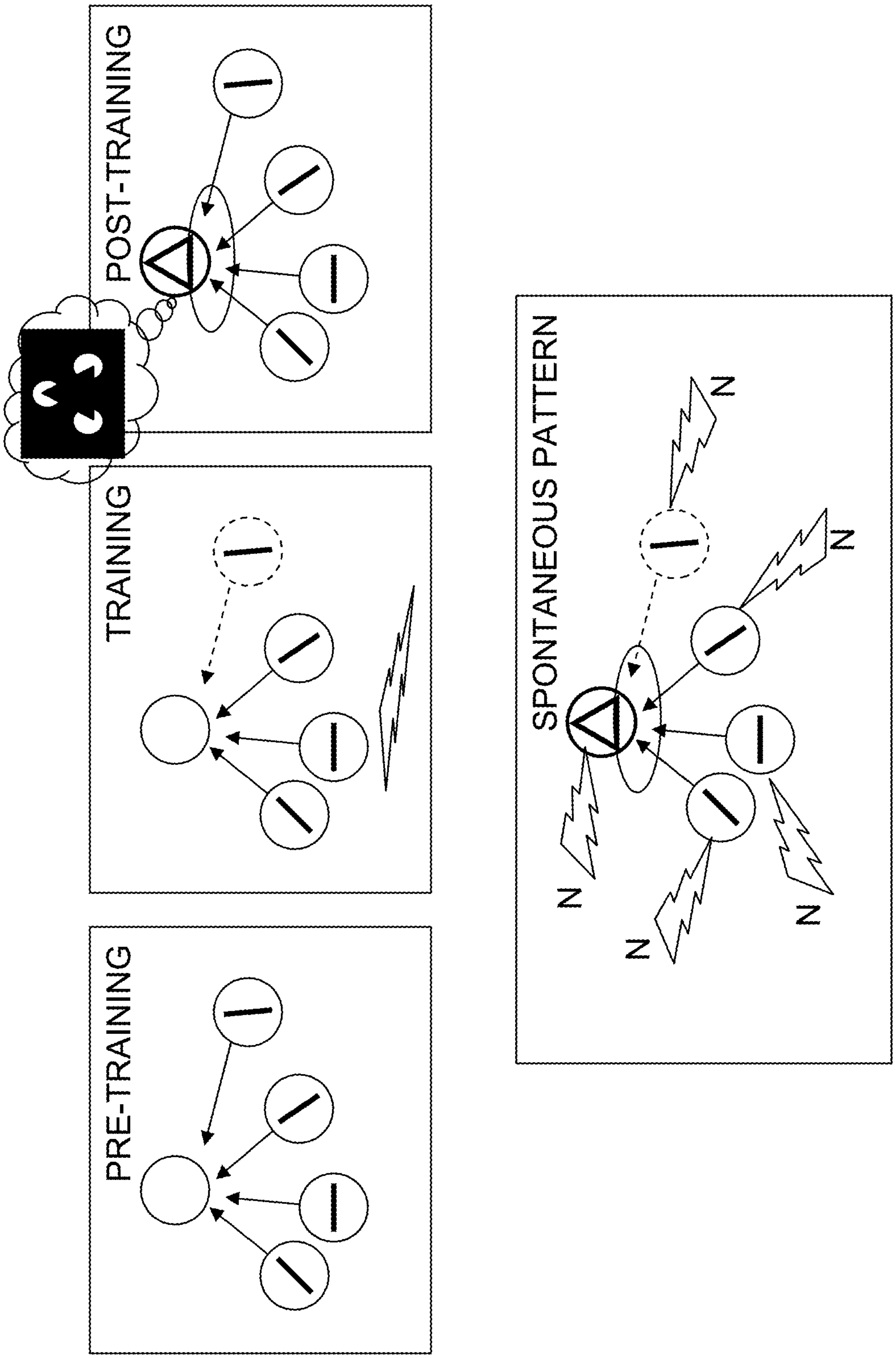
FIG. 16 shows an example of a toy model.

The crucial question to consider with regards to the SPs is what happens to this simple toy model when sensory inputs are blocked—i.e., in a state of "rest"? Making the simplest assumption of residual internal noise that uniformly drives cortical neurons—it is not difficult to see (bottom panel)—that under the impact of uniform random activations, the tendency of the red neurons will be to co-activate—due to their strong excitatory connectivity, while the red and blue neurons will be de-correlated given the weak synaptic biases in this case. An example of a toy model is shown in FIG. 16.

Thus, the spontaneous activity will uncover the pattern underlying connectional structure—essentially recapitulating the trained trace of a-priory network biases. Simply put—the inherent, spontaneously generated, noise in the system is sufficient to uncover the a-priory synaptic biases of cortical networks. Such biases could then be measured by mapping the correlation structures (also termed "Functional Connectivity", FC) in the spontaneous activity fluctuations—the spontaneous patterns—that emerge during rest.

Experimental Support for the Hypothesis

While this is of course a highly over-simplified model, it contains within it three main testable predictions that are reviewed below. First, we expect that the SPs will generally correspond to the average "training" of cortical networks during natural daily life. Second, we would expect the SPs to reflect individual differences in network and cognitive biases, including reflection of cortical abnormalities. Finally, given the dependence of a-priory biases on prior training—it should be possible to re-shape the structure of SPs through controlled focused task-activation under laboratory conditions. Below we consider the experimental evidence pertinent these predictions.

Spontaneous Patterns Reflect Daily Activation Patterns

Figure 18:
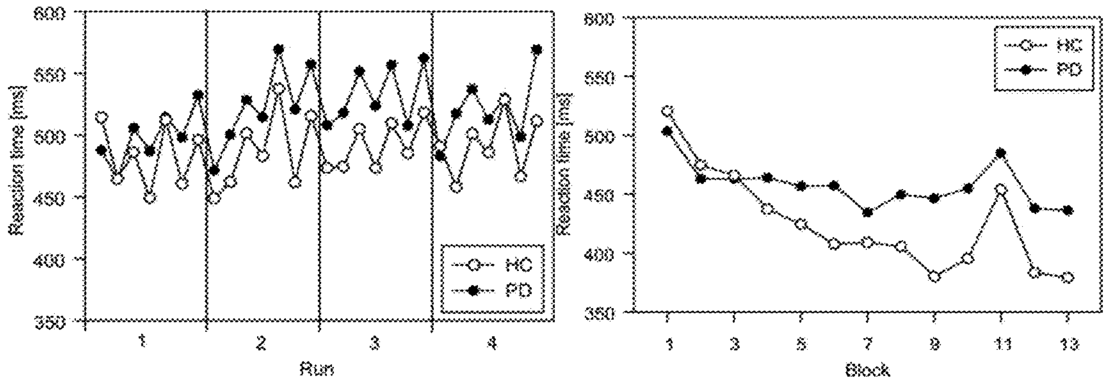
FIG. 18 depicts Z-maps that show the contrast between 'Sequence' and 'Random' condition for healthy controls and patients with Parkinson's disease.

The first prediction is based on the assumption illustrated in FIG. 18—that the structure of the SPs reflects the average "training" patterns that cortical networks exhibit in the course of daily life. Given the methodological limitations of our ability to follow cortical activations during natural conditions, this prediction cannot be precisely tested using current methodologies. However, first order approximations are abundant.

As previously argued by (Hasson et al., 2004), a fruitful methodology for approximating naturalistic stimuli, at least within the domain of audio-visual cortical systems, could be the use of movies. Following this logic, and taking advantage of the fact that during sleep SPs appear to be as informative as during the wake resting state (Dinstein et al., 2011; Nir et al., 2008b), Ramot et al. (Ramot et al., 2013) used ECOG recordings in patients to map the correlation structure generated in the patients' cortex by repeated movie segments. Critically, when this movie-driven correlation pattern was compared to the patterns that emerged spontaneously when the patients were asleep—the movie and sleep patterns were significantly correlated—indicating a recapitulation of the correlation structure of the movie driven and spontaneous patterns (see FIG. 18). Interestingly the range of patterns was significantly richer during REM sleep—suggesting a possible from the typical resting state statistics during dreaming.

Under the reasonable assumption that approximately the same networks were activated during movie watching and during the truly natural audio-visual stimulation the patients underwent in their daily experience—then these results support the notion that the SPs reflect the averaged prior activation patterns of the patients.

Individual differences in network computations are reflected in spontaneous patterns While the main body of brain imaging research has focused on mapping common principles of human cortical function—an important complementary aspect relates to individual differences—how unique cognitive biases and traits of individuals are reflected in their cortical organization. A number of studies reveal that these patterns should provide a potentially powerful method to map such cognitive traits across individuals and unique groups.

Important set of computational failures concerns cases where cognitive biases are distorted to such an extreme level that they lead to cortical mal-function. In this case the STR hypothesis predicts that the resting state patterns should recapitulate the typical functional abnormalities encountered by patients suffering from brain pathologies. Although a large body of data is rapidly accumulating with regards to abnormalities of SPs associated with various brain pathologies—surprisingly few studies have attempted to directly compare task-related abnormalities with their corresponding SPs (Gilaie-Dotan et al., 2013; Liu et al., 2011; Watkins et al., 2012).

In the visual domain, Gilaie-Dotan et al (Gilaie-Dotan et al., 2013) have compared visual activation patterns in an individual suffering from a developmental form of object agnosia with his SPs. A striking abnormality in the visual activation pattern in this individual was manifested in a profound inactivation of mid-hierarchy visual areas during processing of a variety of visual stimuli. Such inactivation is expected to produce a strong de-correlation between these mid-areas and the rest of visual areas during naturalistic viewing. As expected from the STR hypothesis—examining the SPs revealed a similar disruption in FC of the SPs in this individual (see FIG. 18).

In an important study Baldassarre et al. (Baldassarre et al., 2012) demonstrated a correlation between individual differences in resting state FC and individual differences in performance of a subsequent novel perceptual task. According to Zou et al intrinsic resting state activity (ALFF—amplitude of low-frequency fluctuations) can predict subsequent task-evoked brain responses and behavioral performance in a working memory task (Zou et al., 2012). ALFF—behavior correlations were also described for object color knowledge tasks (Wang et al., 2013) and resting state FC has been shown to predict cognitive control and intelligence (Cole et al., 2012; van den Heuvel et al., 2009), as well as reading competency (Koyama et al., 2011; Wang et al., 2012a) and pain perception (Riedl et al., 2011; Wager et al., 2011). A number of other studies have demonstrated similar predictive properties of spontaneous ongoing activity on individual performance (Barttfeld et al., 2013; Boly et al., 2007; Coste et al., 2011; Engel et al., 2001; Freyer et al., 2013; Hampson et al., 2006; Martin et al., 2012; Mennes et al., 2010; Seeley et al., 2007; Tambini et al., 2010; Ventura-Campos et al., 2013; Wang et al., 2012a; Zhu et al., 2011) and even personality traits (Adelstein et al., 2011).

Figure 17:
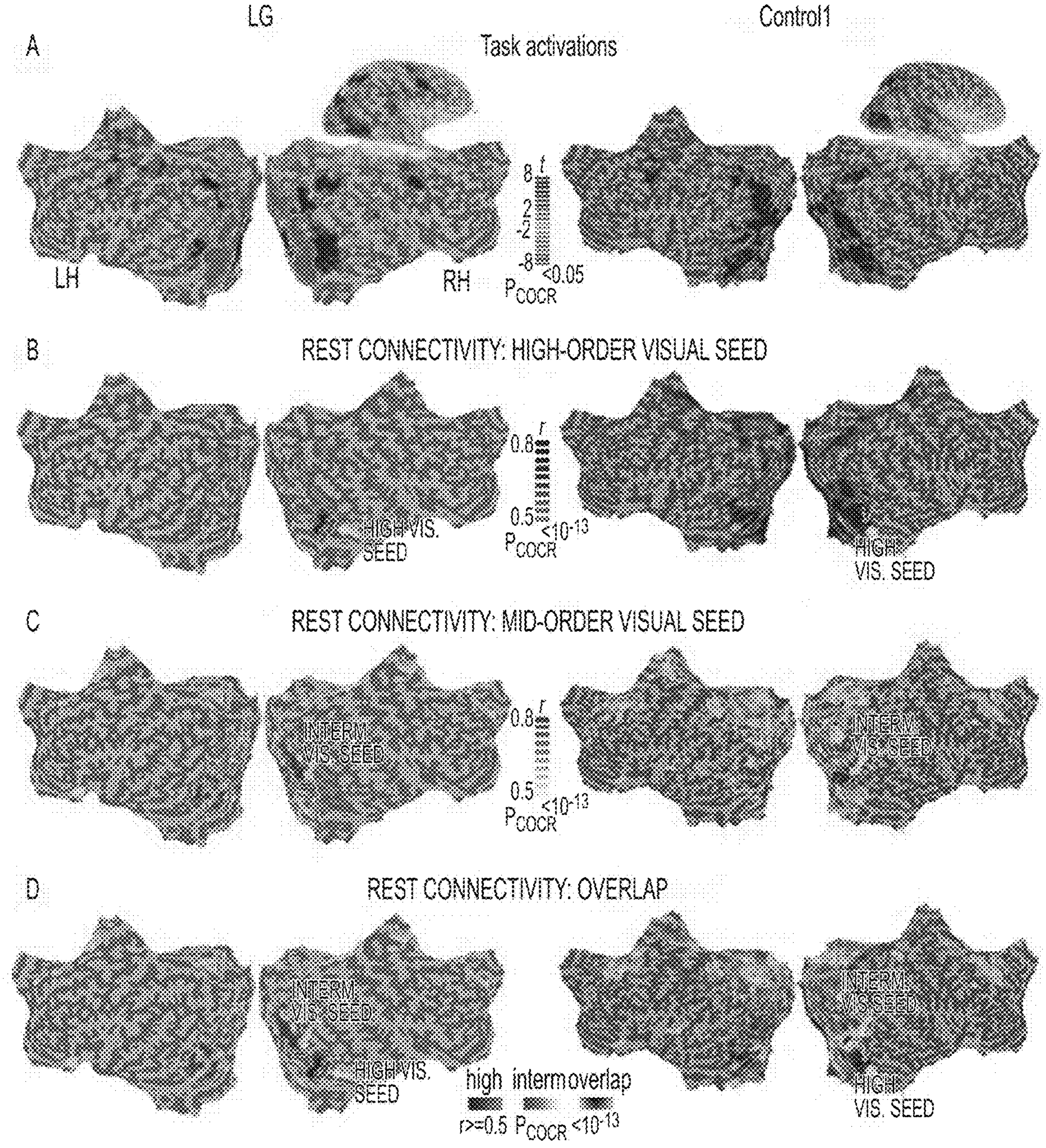
FIG. 17 shows an example of Task activation and rest connectivity (Gilaie-Dotan et al., 2013).

FIG. 17 shows an example of Task activation and rest connectivity (Gilaie-Dotan et al., 2013).

Examining Storage of a-Priory Information Under Laboratory Conditions

Finally, the most direct means of studying the dynamic storage of a-priory information is to inject such information under laboratory conditions. A number of recent studies have indeed addressed this possibility under carefully controlled experiments. Thus, it was shown that prolonged exposure to distinct categories of visual information causes differential coupling of frontal networks with posterior category-selective visual regions during subsequent rest (Stevens et al., 2010). A connection between mechanisms of learning and resting state activity was also described for associative encoding (Tambini et al., 2010), visual perceptual learning (Lewis et al., 2009), motor learning (Albert et al., 2009; Taubert et al., 2011; Yoo et al., 2013), semantic matching (Wang et al., 2012c), language comprehension (Hasson et al., 2009), and emotional and pain processing (Eryilmaz et al., 2011; Riedl et al., 2011). Plastic changes triggered by learning have been demonstrated for sleep regulation as well (Huber et al., 2007). Huber et al. (Huber et al., 2007) found an increase in slow-wave sleep localized to the premotor site that underwent TMS-induced potentiation during the previous wakefulness.

If indeed the SPs reflect past cortical activations—the a-priory information should, in principle, be present at a fairly long delay after the original activation. A direct demonstration that this is indeed the case has been recently provided by Harmelech et al (Harmelech et al., 2013). In this study, the SPs were compared before and a day after a single short epoch of intense activation was induced in the dorsal anterior cingulate cortex (dACC) using an fMRI-based neurofeedback (NF) paradigm. A significant and lasting restructuring of the SPs according to a Hebbian-like rule was observed. Thus, the change (increase and decrease) in FC strength of cortical voxels during rest reflected the level of their prior co-activation during the NF epoch. Data-driven examination of the change in global FC a day after the NF revealed the dACC as the region demonstrating the most prominent change.

In order for an audio signal to be detected a certain threshold needs to be crossed. The same applies for any other sensory input. Perception takes place when a certain perceptual dynamic threshold is crossed. However, capacity might already have been taken up for proper perception of the signal, due to additional tasks such as speaking and/or moving. This means that the perceptual “threshold” is reliant on the data streams of motion and speech (reflecting higher cognitive functioning needed e.g. everyday tasks). Essentially, these data streams can add noise to the perception of the initial signal. Fusion now happens as additive noise to the signal of interest (e.g. audio signal “left”). Subsequently, this will mean that a particular signal “left” can be drowned out if too many other things require attention/cognitive function Werheid et al. (Werheid et al., 2003) investigated implicit rule learning in a combination of Parkinson’s and healthy patients, using a combination of fMRI and a variation of serial reaction time tasks to measure brain activity of previously learned motion-based task sequences. The results of this study suggest that activations in the frontomedian and posterior cingulate cortex, instead of random blocks, are linked to a larger role for the frontomedian cortex in stimulus prediction, an area of cognitive deficit in Parkinson’s patients. Patients with early-stage Parkinson’s disease experienced difficulties in the pre-training phase of the experiment, but rule-learning remained intact during fMRI data acquisition when the rules had been instilled and stimulus prediction was taken out of the equation. fMRI results showed very little difference between the PD and control patients in terms of frontomedian and posterior cingulate activations, and that the effect on patients with early stage PD of the disease progression is primarily limited to lateral striatofrontal dopaminergic projections, because medial dopaminergic projections, which are used in the application of previously known “rules,” or routines, are not significantly affected by the disease in this stage.

FIG. 18 depicts Z-maps that show the contrast between ‘Sequence’ and ‘Random’ condition for healthy controls and patients with Parkinson’s disease. There is a significant disparity between reaction times for healthy controls (white) and patients with Parkinson’s disease (black)(Werheid et al., 2003). Note that in patients with PD, the activity level decreases in the transition from sequence to random activities, suggesting greater difficulty with stimuli for which the patients are unprepared. This phenomenon is notably absent in the healthy control component. Their findings are in agreement with the results of the cognitive load study previously mentioned (Bergmann et al., 2015). The fMRI study confirms that processing will show differential indicators during task load conditions.

Supporting Work

A number of supporting techniques may be used to implement methods described herein. Such techniques may relate to the data mining for military and intelligence applications (Cambria et al., 2013; Cambria et al., 2012; Howard, 2001a; Howard, 2001c; Howard, 2002; Howard, 2007; Howard, 2011a; Howard, 2011c; Howard, 2012b; Howard, 2012h; Howard, 2013b; Howard, 2013e; Howard, 2013h; Howard and Argamon, 2009; Howard et al., 2009; Howard and Cambria, 2013a; Howard and Guidere, 2011; Howard and Leisman, 2013; Howard and Lieberman, 2012). These methods have evolved into a methodology and research design philosophy we call the BCCS.

Background

Preliminary studies have validated the hardware and methods necessary to lay the foundation for a non-invasive detection system using wearable sensors and a combination of algorithms we call the Brain Code Collection System (BCCS).

Experiment 1: Body Sensors as Accurate as Gold Standard Optical Tracking

We have demonstrated that sensor networks and wavelet analysis can be used to accurately measure and differentiate complex movement in real-life situations. Data collected from complex arm movements and joint stability demonstrated that wearable body sensors can measure activities of daily living with similar accuracy to gold standard optical tracking (Bergmann et al., 2013a; Bergmann et al., 2013). Body Sensors Networks (BSN) allow all three spatial dimensions to be used, and thus provide a potentially more comprehensive analysis of movement. We have tested the BSN’s ability to measure the distal point of the left arm (hand plus wrist) during elbow movements. Complex arm movements were measured for three different activities: 90-degree elbow flexing from an upright sitting position, 90° shoulder abduction with the elbow fully extended, and 90° shoulder abduction and 90° elbow flexion with an internal rotation, followed by moving to 45° shoulder retroflexion and 120° elbow flexion (See FIG. 20). We found that BSN performed comparably to its optical counterpart, with correlations in the X, Y, and Z dimensions reaching 0.99, 0.95, and 0.99 respectively. Therefore the body sensors measure as accurate as optical tracking, which is the gold standard for measuring body movement.

Figure 19:
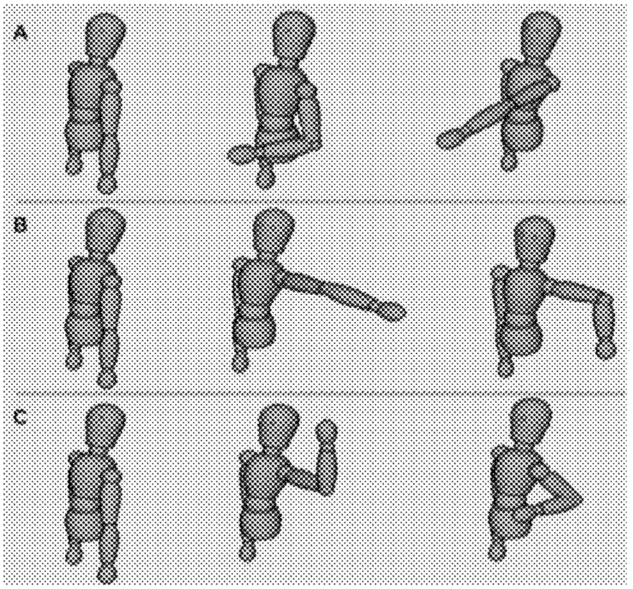
FIG. 19 shows complex arm movements.
Figure 20:
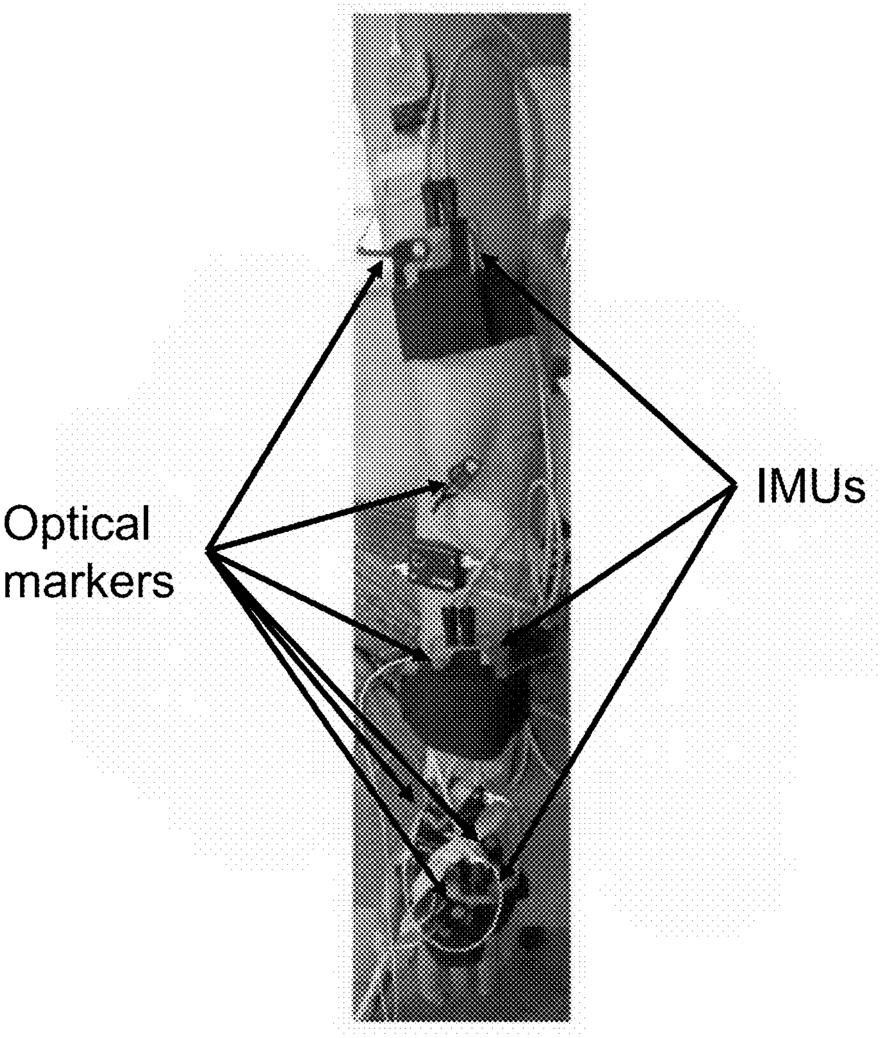
FIG. 20 shows a prototype BSN for an upper limb.

FIG. 19 shows complex arm movements. FIG. 20 shows a prototype BSN for an upper limb.

Experiment 2: Body Sensors that Accurately Quantify User Interaction with Objects The BSN system was further validated by measuring differences in motor behavior, in response to a changing environment. In Bergman et al. (2013) three subjects were asked to perform a water-pouring task with three slightly different containers; pitcher, teapot, and kettle. Wavelet analysis was used to measure behavioral changes within each subject and between all three subjects. There were significant differences in movement with each container. Results showed that body sensors and wavelet analysis accurately quantified subtle behavioral adjustments due to environmental changes (FIG. 20). This preliminary validation demonstrates the potential utility of a BSN system to measure a range of body movement with object interaction. In assessing BSN's effectiveness in Alzheimer's disease Bergmann and Howard (2012) found the BSNs effective in measuring a range of activities. They also determined that temporal changes can be categorized using the MSI classification method. This technique allows for natural randomness, which can provide a non-invasive screening method to measure real-life behavior.

Figure 21:
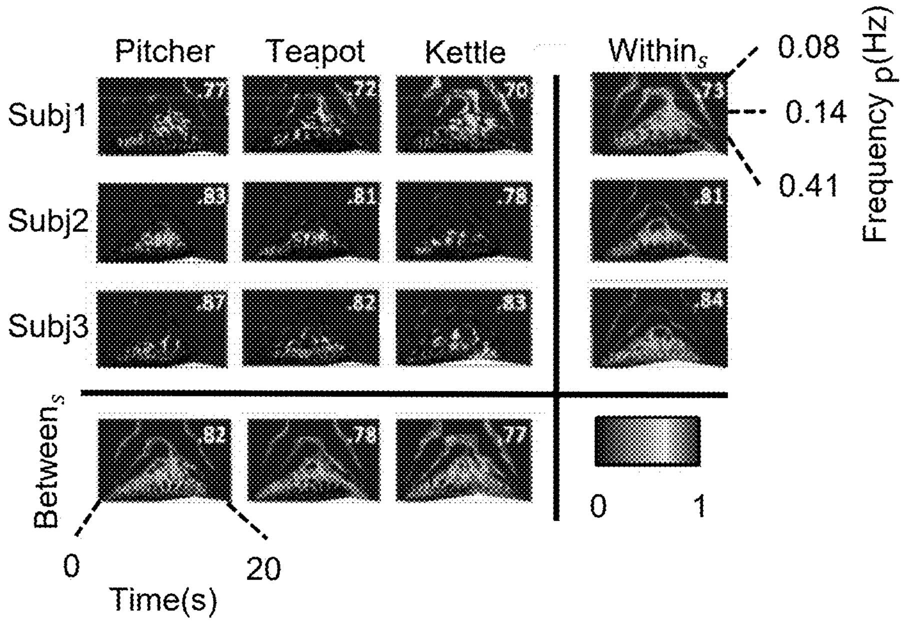
FIG. 21 shows the results of range-of-motion tasks under different speed conditions.
Figure 22:
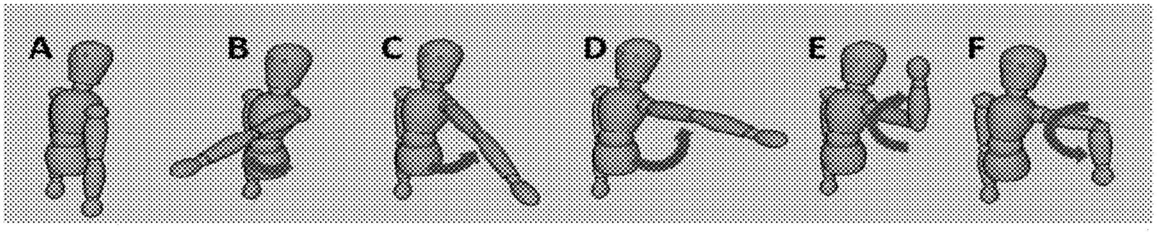
FIG. 22 shows movements performed by participants.

Experiment 3: Validation of Wavelet Analysis to Define Spatial and Temporal Changes Howard et al. (2013m); Howard et al. (2013o) demonstrate that wavelet analysis can differentiate between patients and "healthy" controls. Seven healthy participants and eight rotator cuff injury patients performed five range-of-motion tasks under different speed conditions. FIG. 21 shows the results of range-of-motion tasks under different speed conditions. These results showed differences in range of motion and speed of movement between the patient and healthy groups. Rotator cuff patients exhibited range of movement (ROM) limitations compared to control subjects with significant differences across all elevations at "normal" speed. Two examples of simulated outcomes for wavelet coherence are given in (FIG. 22). These examples show the wavelet coherence of two generated sine waves, which mimic the "fast" and "normal" condition. In example (A.1) there is a factor 2 difference in movement frequency between the conditions, while the second example (A.2) shows a very small offset from the baseline frequency. It is clear from FIGS. 21-25 that there are more localized similarities in B.2 compared to B.1.

FIG. 22 shows Movements performed by participants (A) Starting position for each movement (B) sagittal (forward flexion) plane rotation (C) scapular plane rotation (D) frontal (abduction) plane rotation (E) external rotation and (F) internal rotation.

Figure 23:
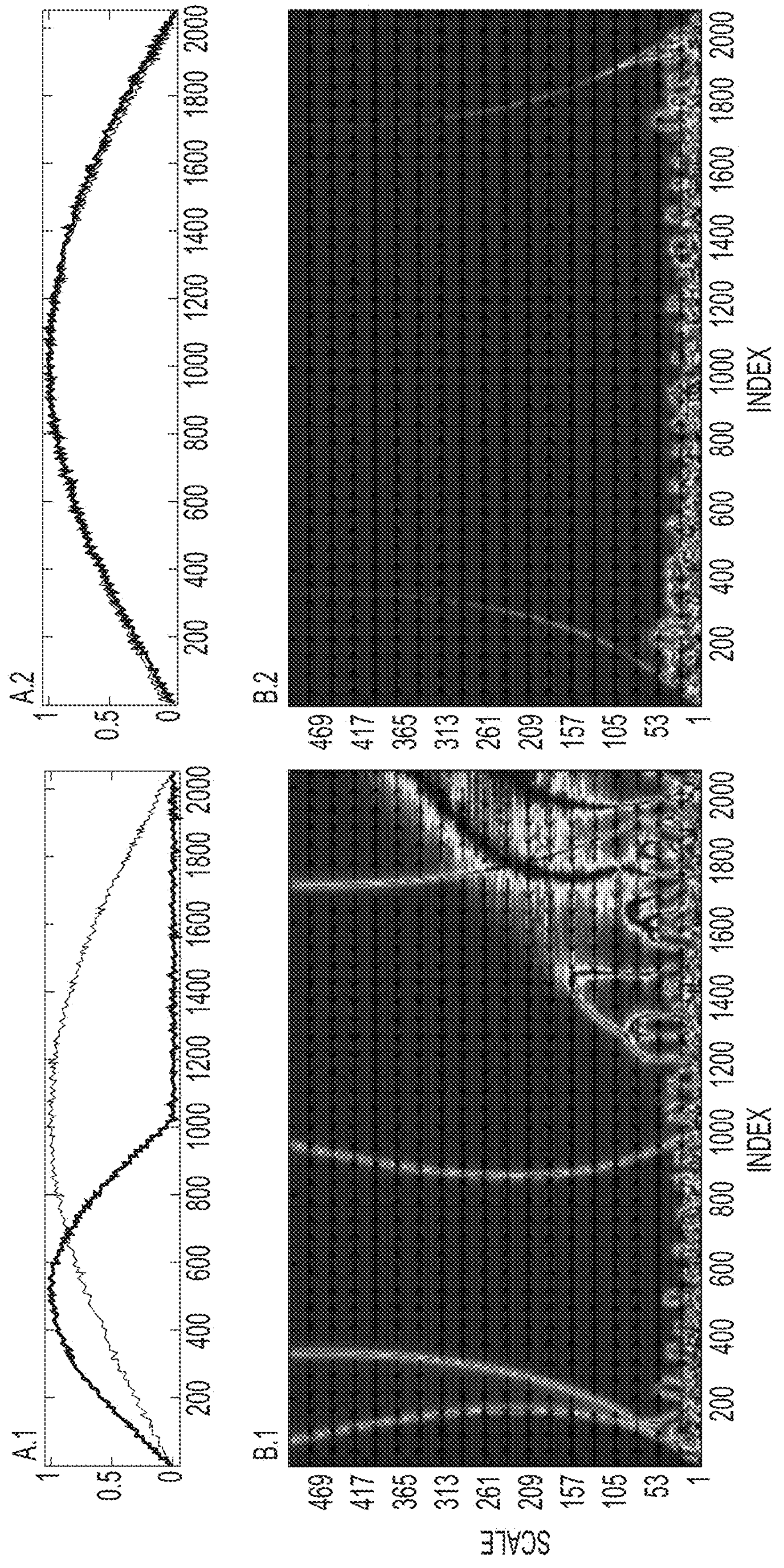
FIG. 23 shows two examples of simulated outcomes for wavelet coherence.

FIG. 23 shows two examples of simulated outcomes for wavelet coherence.

Experiment 4: Body Sensors Capable of Measuring Acceleration Even Under Extreme Conditions After testing accuracy of the BSN to measure complex movement and object interaction, we considered engineering and design criteria for use in naturalistic/real world environments—for future design of wearing sensors 24/7 during everyday living (Bergmann and Howard, 2013). The BSN was tested for robustness in an extreme environment. Accelerometer data was collected from a wearable sensor and high frequency camera. Pilot testing showed that decelerations during water-ski jumping were out of the measurement range using a 5 g accelerometer system. Our analysis computed two 100 g accelerometers would be required to measure decelerations during water-ski jumping. The sensor, circuitry, and interface remained working under these extreme conditions. Findings suggest that BSNs are capable of measuring in harsh-environments and would be adequate to measure in naturalistic environments, which do not present conditions as extreme as water-ski jumping.

Figure 24:
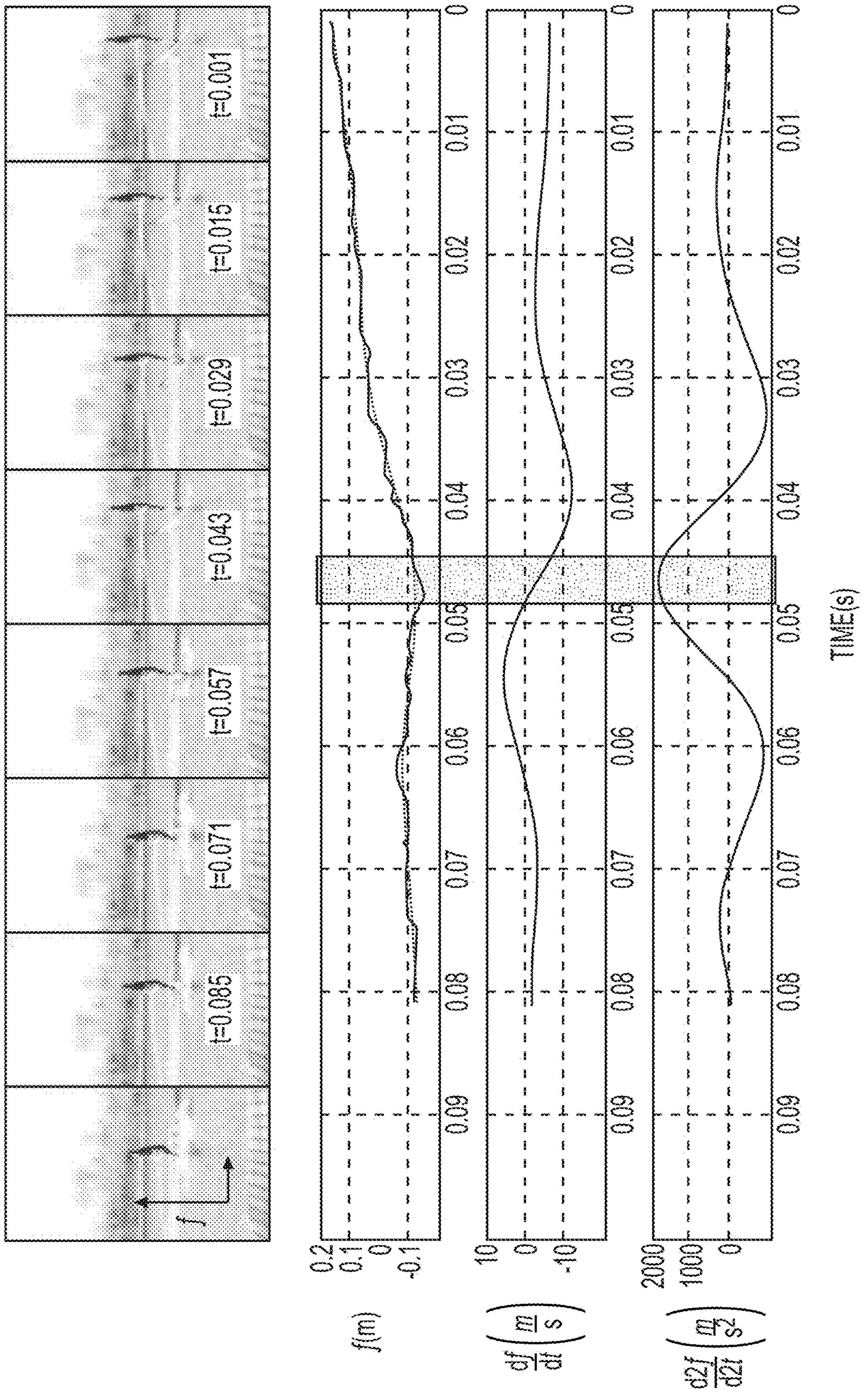
FIG. 24 shows frames from the high frequency camera showing the landing of a skier entering from the right side of the frame.

FIG. 24 shows frames from the high frequency camera showing the landing of a skier entering from the right side of the frame. The subsequent plots show the position f of the ski binding and the two derivatives with m representing meters and s denoting seconds. The red line shows the data low-pass filtered at 50 Hz, while blue lines show "non-filtered" data. Peak acceleration occurs during the initial landing period highlighted by the filled blue box.

Experiment 5: Pocket Sensors

Most sensor systems interfere with everyday life and prevent normal activities from being carried out. Better functional placement could provide higher levels of conformity. For this reason, a truly unobtrusive system, integrated into objects that are already used on an everyday basis, would be beneficial for the quality and quantity of data collection. With this in mind, we wanted to assess the potential for sensor integration into a smart phones by testing the BSN's adaptability to functional in a pocket. (Bergmann et al., 2013a) conducted a study to compare traditional and functional body sensor placement. The goal of this analysis was to show the viability of inertia-based activity recognition sensors to determine what types of behaviors a subject is engaging in. Results suggest that the directional shifts of median frequency are independent of the placement, meaning there is a greater possibility of using more functional placement and there is potential to use the BSN in a pocket.

Figure 25:
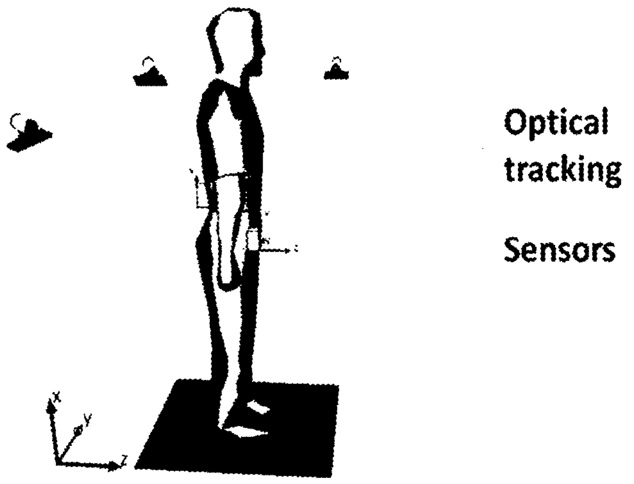
FIG. 25 shows an example of pocket sensors and optical tracking sensors.

FIG. 25 shows an example of pocket sensors and optical tracking sensors.

Experiment 6: Clothing Sensors that Measure Joint Stability

Recent studies have verified that wearable body sensor systems can be used to measure a variety of movement patterns related to joint stability (Bergmann et al., 2009a; Bergmann et al., 2009b; Bergmann et al., 2013). A novel Integrated Clothing Sensing System (ICSS) was constructed at Imperial College London in collaboration with Queen's Mary University. The sensor designed for the ICSS is made of innovative carbon black and polyurethane composite films. Results to date have demonstrated that the ICSS BSN technology successfully monitors joint stability, at a level of sensitivity comparable to gold standard measurements. By testing the body sensor networks in a harsh environment such as water-skiing, we validated that the current sensors can be used in real world situations. However, less obtrusive methods are necessary to integrate these systems into activities of daily life. More functional placements of the sensors should provide higher levels of conformity, but may affect the quality and generalizability of the signals. Differentiation of the signal into a translational and gravitational component decreased the level of agreement further, suggesting that combined information streams are more robust to changing locations then a single data stream. Integrating multiple sensor modalities to obtain specific components is not likely to improve agreement across sensor locations. This study confirmed the potential to measure signals with more user-friendly sensor configurations that will lead to a greater clinical acceptance of body-worn sensor systems.

Figure 26:
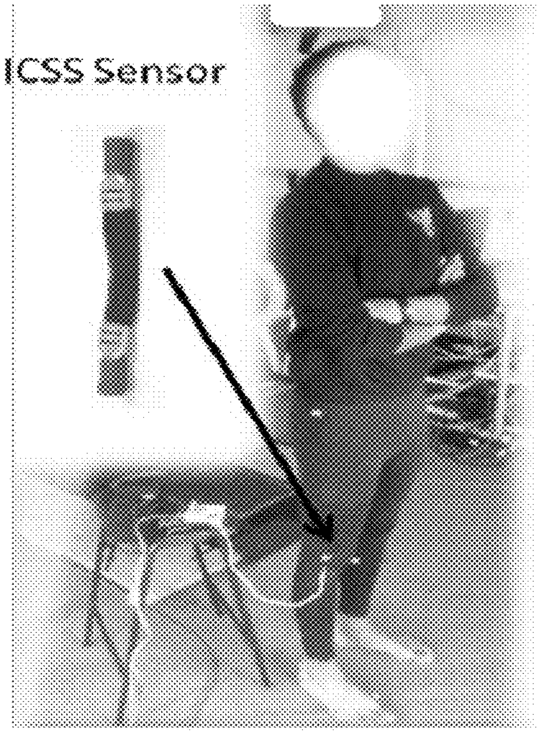
FIG. 26 shows an example of an ICSS Sensor.

Knee joint stability was measured using the Integrated Clothing Sensing System (ICSS) and compared to the gold standard measurement system (Vicon). Results found that the ICSS is capable of measuring different levels of joint stability. An overall correlation coefficient of 0.81 ($p<0.001$)

was calculated, meaning there was a strong association between the ICSS and the optical tracking system during different levels of stability. FIG. 26 shows an example of an ICSS Sensor.

Experiment 7: Measuring Cognitive Load

We often perform speech and movement tasks simultaneously, but it remains unclear how cognitive processing is affected by multiple demands. Cognition is affected across several dimensions of functioning and requires attention sharing across these functions. Bergmann et al. (2015) explored whether attentional demands could be assessed using a cognitive load experiment requiring speech, movement, and an auditory Stroop task simultaneously. It focused on everyday living routines previously identified in the Motor Activity Log (MAL) for the upper extremity (Uswatte et al., 2005). This work explored how everyday motion and speech tasks can affect cognitive processing measured by performance on a Stroop task. The single loaded tasks consisted either of speaking or making a sandwich, while the dual task required both. Results indicated that cognitive function is affected by loaded conditions. Correct responses were lowest under dual task conditions.

Experiment 8: Pain Biomarker

Preliminary data from the laboratories of our colleagues at the universities of Oxford, U K and Brown, US converge on the observations that pain deregulates network dynamics in the thalamocortical circuitry. Pre-clinical studies using animal models of pain, as well as intraoperative recordings from humans, suggest that pain causes increased power of oscillation in the 3-30 Hz range within brain areas mediating the processing of nociceptive signals (Brittain et al., 2009; LeBlanc et al., 2014; Saab, 2012; Stern et al., 2006b)

At a preclinical level, the Saab lab at Brown University demonstrated that animal models of acute and chronic pain are invariably associated with a deregulation of network dynamics in the thalamocortical circuitry (LeBlanc et al., 2014; Saab, 2012). In particular, pain caused an increase in the power of oscillatory activity within the low frequency range (3-30 Hz) of the local field potential recorded from primary somatosensory (Si) cortex, in addition to attenuating signal coherence between Si and sensory thalamus. Interestingly, manifestations of chronic pain were different from those of acute pain, suggesting the possibility of phenotype segregation based on empirical data. These data are in support of clinical observations indicating increased cortical power, recorded by EEG, in patients with chronic intractable pain (Stein et al., 2006). Green et al. (2009) identified an electrophysiological signature of intractable pain in patients at a thalamic level, whereby intraoperative recordings during a cluster headache episode displayed a significant increase in local field potential power at approximately 20 Hz (Brittain et al., 2009). Human imaging studies further suggest that the transition of pain from the acute, manageable pain to the chronic, treatment-resistant pain phenotype can be predicted based on temporal follow up of intra-cortical functional connectivity (Baliki et al., 2012). This evidence from the literature is mostly relevant to our goal of longitudinally assessing disease trajectories and of segregating disease phenotypes and comorbid conditions such as pain and other sensory disturbances. It is also particularly appealing that these potential 'biomarker' modalities for the detection of pain-related brain activity are non-invasive and amenable to standard EEG recordings with appropriate algorithms for data analysis. We postulate that similar pain 'biomarkers' can be applied in our study to detect sensory abnormalities in our patient population. In addition, we believe that a similar approach using longitudinal EEG assessment can be adopted to identify and validate novel biomarkers for PTSD. Furthermore, the fact that the pain biomarker is presumably sensitive to acute versus chronic forms of pain, and that it's possible to predict pain transition from acute-to-chronic, is support that our approach of similarly detecting and predicting PTSD-sensitive phenotypes is based on empirical measures.

Experiment 9: Pain Detection Algorithm

As a follow up to our published data, we propose to use the pain biomarker at the electrophysiological level using EEG hardware, also referred to here as non-invasive recording of local field potential (LFP). Based on our previous observations, we will record spontaneous, resting state LFP from electrodes targeting predominantly Si (corresponding to 2 cm posterior or occipital to C3/C4). In order to analyze spectral changes in the 3-30 Hz band, we will apply complex Morlet wavelets, yielding in a time-frequency domain. A mean of the time-frequency energy is then obtained across single trials, allowing analysis of non-phase-locked frequency components. Mean spectral power is then averaged across extended 10-20 electrodes. The validation of this biomarker at pre-clinical and clinical levels suggests if may be useful for detecting sensory abnormalities in the PTSD population tested in this study. Furthermore, it will allow us to segregate PTSD from other comorbid or confounding sensory disturbances.

Experiment 10: EEG Algorithm as Accurate as In Vivo DBS

Howard et al. (2013t) tested whether the NOD algorithm could identify a biomarker, originally detected in DBS recordings of LFPs, using EEG recordings. A signature for neuropathic pain identified in deep brain electrodes LFPs was used to test the NOD algorithm with raw EEG collected from chronic pain patients. The NOD algorithm was able to detect the signature and distinguish pain and control subjects from EEG recordings. The validation of the NOD algorithm with pain data suggests that it may also be useful for PTSD. In future work, EEG may become a means to link motor and cognitive function, but for now it is being explored as a reference measurement.

The NOD algorithm takes EEG recordings to detect a biomarker previously identified with in vivo recording. A neuropathic pain biomarker (this biomarker will be referred to as "pain spindles," the term is used in this thesis interchangeably with alpha spectrum.) observed by (Green et al., 2009) was recorded from local field potentials deep within the periaqueductal grey and the sensory thalamus. Pain evoked an increase in spindle shaped bursts in 8-12 Hz in the PAG and 17-30 Hz in the sensory thalamus. Therefore, the NOD algorithm used the alpha band as input features for machine learning. Raw EEG data was input into the algorithm, which consists of pre-processing, signal processing, and machine learning. The algorithm flowchart is shown in the figure below. The results of the Howard et al. (2013) NOD algorithm used on Parkinson's patients gave 95% accuracy levels, this system could replace the currently used 256e EEG method. With PD patients it showed promise as utility for the assessment of the "different stages of disease progression" (Howard et al. 2013).

Figure 27:
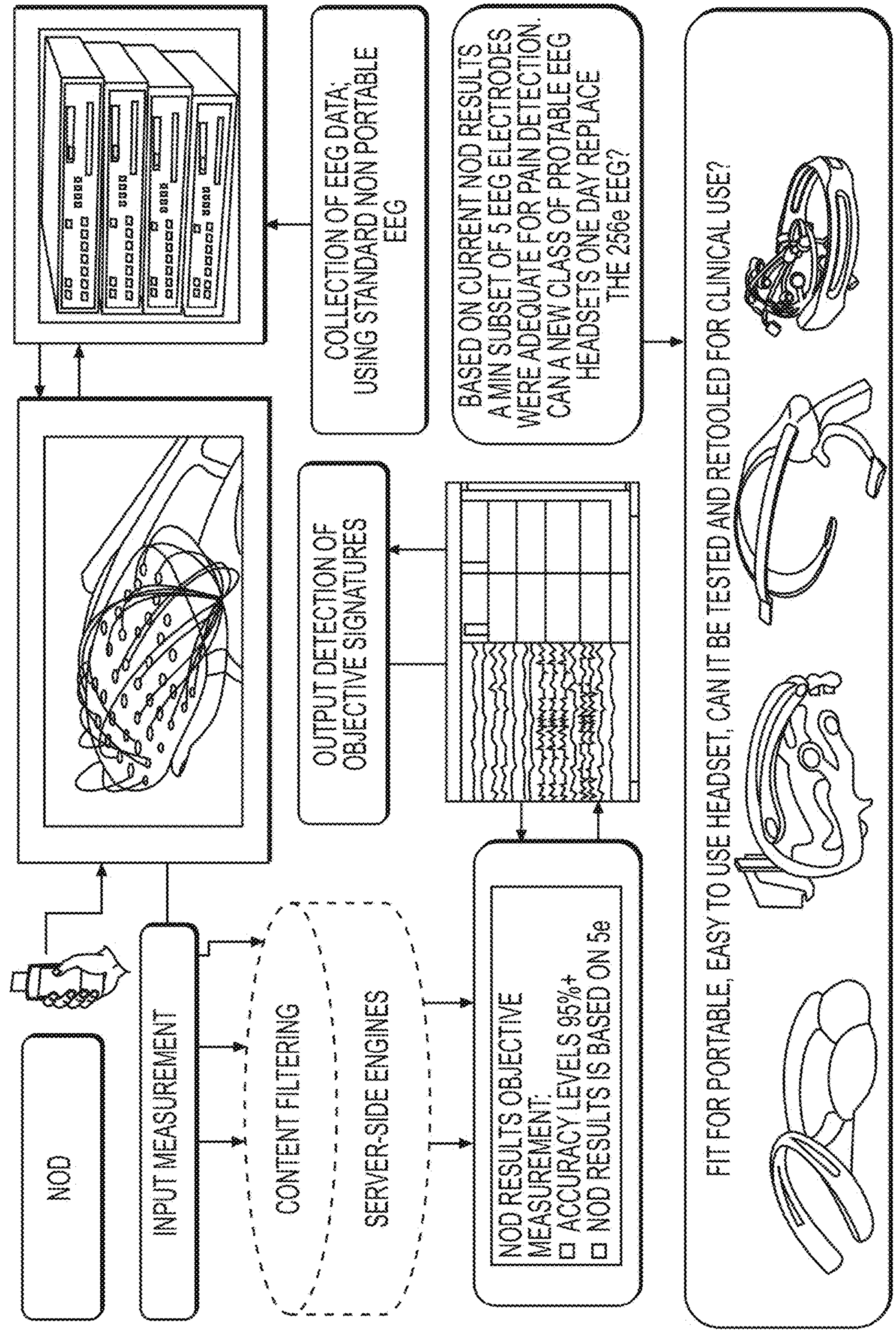
FIG. 27 shows an example of a NOD algorithm.

FIG. 27 shows an example of a NOD algorithm.

Figure 28:
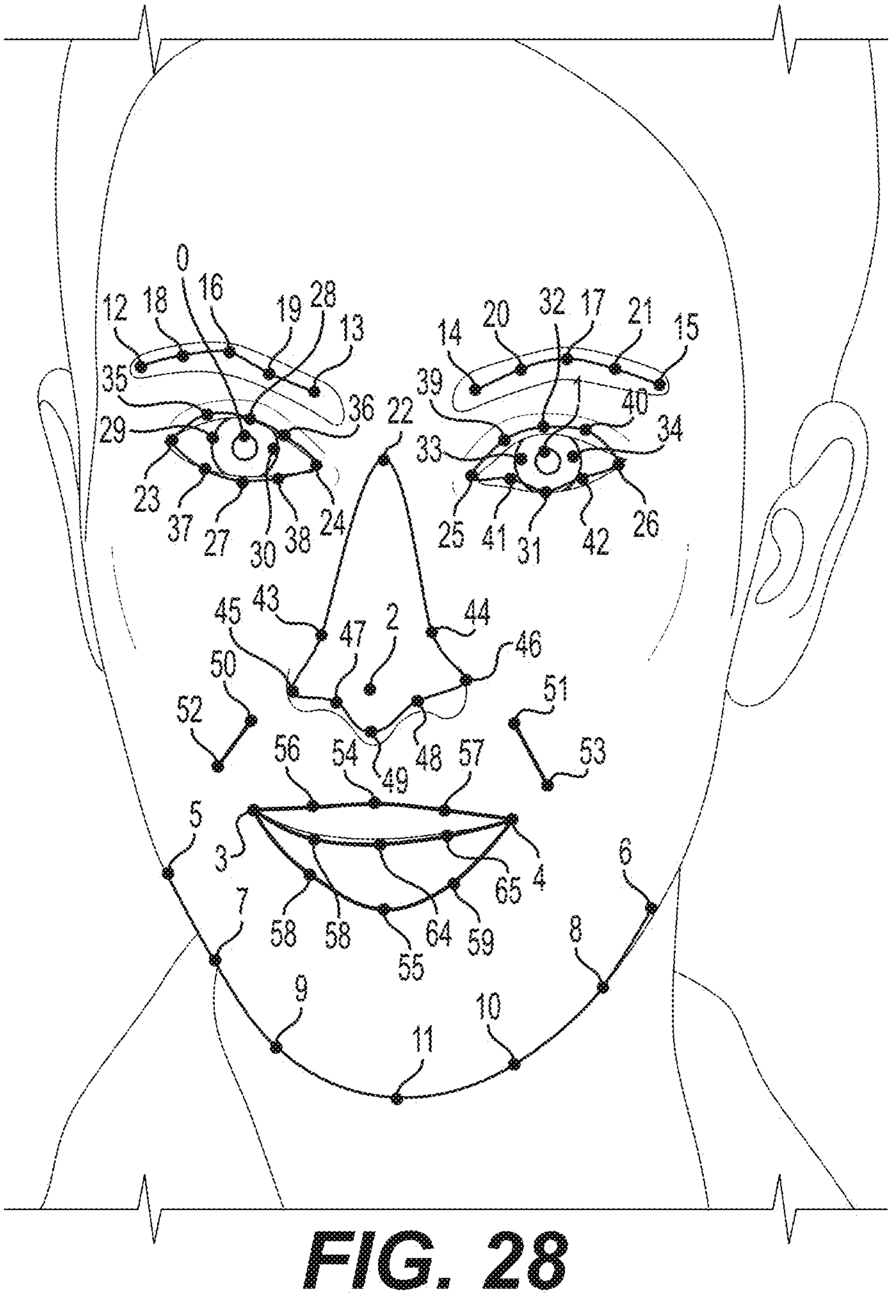
FIG. 28 shows an example of facial feature characteristic points.

Experiment 11: Emotion Classification and Facial Feature Extraction Using Machine Learning To better understand facial expressions as they relate to both motor control and emotions, (Poria et al., 2013) conducted a two part data analysis study to 1) test a sentiment classifier and 2) use facial feature points to analyze a Parkinson's Disease patient compared to a universal database(Howard, 2014). The emotion classifier algorithm was trained and tested using control data and demonstrated 97.25% accuracy compared to human annotation. In part two of the study, facial feature extraction applied to images of a Parkinson's Disease patient indicated several differences between the facial characteristic points (FCP) of the Parkinson's Disease face compared to "normal" averages of a universal database. FIG. 28 shows an example of facial feature characteristic points. Significant measures included lower blink rate, distance between right eye and left eye, distance between the upper and lower line of the left and right eye, distance between the left, right eyebrow inner and outer corner. In addition, 4-6 Hz rate of random eye movement was found in the Parkinson's disease patient (Poria et al., 2013). Although there were several limitations in the study, the preliminary findings encourage further research on facial features to measure motor impairment and facial expression to detect emotional states in trauma patients.

Experiment 12: Vision System

Jhuang et al. (2010) recently reported a significant advancement with the development of an automated vision system (based on motion processing in the dorsal stream of the visual cortex) capable of rapidly and continuously tracking and identifying rodent behaviors with a degree of accuracy far superior to current automated methods and indistinguishable from that of human observers (Jhuang et al. 2010). The robust quantification of complex behaviors imposes a major bottleneck and a number of controversies in behavioral studies because of the inherent biases and challenges associated with the manual annotation of behavior. Our hope is to resolve many of these issues with the development of objective quantitative computerized techniques.

Current automated testing systems of animal behavior, including expensive commercial systems, rely solely upon simple digital subtractive and sensor based approaches that give coarse estimates of animal behavior yet often fail to discriminate between subtle differences in behaviors. These systems are error-prone and cannot be used to study natural behaviors. Our system departs from these commercial systems in that (1) it leverages state-of-the-art computer vision techniques and (2) it is trainable, i.e., it learns to distinguish between behaviors from labeled video examples rather than through programming, and based on user feedback, can improve its accuracy. The current iteration of the system allows us to non-invasively track, identify, and quantify naturally occurring behaviors in singly housed mice over long spans of developmental time. In collaboration with Dr. Bath, we have developed the first of its kind fully automated high-throughput rodent behavioral testing facility (mdb.clps.brown.edu). This facility is unique in that it integrates high-level computer vision, machine learning, and custom-built hardware solutions with behavioral testing to automate long-term tracking, cataloging, and analysis of home cage behaviors along with standard rodent testing paradigms. We are now capable of simultaneously monitoring and analyzing the behavior of dozens of animals over long spans of developmental time (Leussis et al. 2012; Bath et al. in sub). The core produces everyday several Terabytes of data, which would require nearly 1,000 human experimenters for manual annotations.

More recently, Serre et al. have been extending the approach to human actions. A key initial step in developing automated computer vision systems is to collect and annotate videos that train and test the vision algorithms. Serre's group has thus collected two very large datasets of human action: The Human Motion DataBase (HMDB) is the largest action video database to-date with 51 action categories, which in total contain around 7,000 manually annotated clips extracted from a variety of sources ranging from digitized movies to YouTube (Kuehne et al. 2011). We used this database to evaluate the performance of representative computer vision systems for action recognition (including our own) and have explored the robustness of these methods under various conditions such as camera motion, viewpoint, video quality, and occlusion. More recently, we have collected a large dataset of daily cooking activities (Kuehne et al. 2014): The dataset includes a total of 52 participants, each performing a total of 10 cooking activities in multiple real-life kitchens, resulting in over 77 hours of video footage. We have developed a structured temporal generative approach in combination with multiple video feature descriptors, for both the recognition of cooking activities (e.g., making pancakes) as well as the semantic parsing of videos into action units (e.g., cracking eggs).

Narrative and Figurative Language

Narrative in language offers an account of a sequence of events homomorphically preserving an order structure of thoughts and its elements, as the narrative sequence of events is usually chronological. In 1985 Marvin Minsky related narrative to thought and the mind in his publication Society of Mind (Minsky, 1985). Minksy understood narrative as storytelling, which he considered a framework of intelligent acts. Through this understanding, narrative in the form of storytelling enables people to share information and knowledge about reality. Additionally, narrative is not just an informational exchange, but informed by our moral and cultural identity, hence narrative is central to the way we think, perceive ourselves, and understand the world suggested that narrative should be used as a basis for design systems relating to the very insights of cognitive state and process. The common approach in neurolinguistics has been to study narrative discourse by looking at mental representations and processing mechanisms using propositional analysis methods (Stemmer, 1999). However the hierarchical aspects of mental representations and the relationship that exists between them have often been neglected. More recently narratives have been examined further in terms of cognition in order to understand how the brain comprehends and responds to these narratives and evokes emotion. Emotion has been a central focus of neuroscience, but the interaction of the brain, emotion and narrative has only recently begun to be studied. These studies suggest that some meaningful shared emotional biological response occurs across individuals, and that emotions experienced in a narrative context resemble emotional responses to very simple stimuli (Wallentin et al., 2011).

Metaphors can be used as a case study to show how emergent properties arise beyond the "normal" context of a signal. Although languages differ in phonetics, concept roots, and perception of the self, many concept templates are common to all languages (Wierzbicka, 1972). These templates are commonly known as conceptual metaphors, and are, simply speaking, concepts that represent other concepts figuratively (Krennmayr, 2007). While models of metaphors and algorithms that differentiate between non-figurative and figurative language have been investigated in contemporary natural language processing and cognitive sciences, their relevance to clinical diagnostics has largely been overlooked.

The idea of a metaphor is abstract as rather than being based in concrete reality. For example, in schizophrenia patients, language disturbance is characterized by the inability to understand the figurative meaning of metaphors (Kircher et al., 2007). Kircher et al. (2007) studied metaphoric sentence processing in patients with schizophrenia and controls using functional magnetic resonance imaging (fMRI). They suggest that the inability to utilize the brain regions crucial for context processing, which are the left inferior frontal and right lateral temporal cortex, may underlie schizophrenic concretism. This finding suggests that studying language and specifically detecting disturbed metaphors in patients with schizophrenia could aid in the diagnosis of such disorders. In order to detect metaphors to diagnose neurological disorders one has to understand the underlying mechanisms that bring about the disordered state. Given that metaphor comprehension has been studied in various neurological disorders, this suggests that analyzing metaphors in various brain disorder patient cohorts at various stages in disease development would aid in developing a neurodiagnostic strategy to detect the correlates of brain disorders early and improve treatment strategies. Further, metaphor analysis can be used to track treatment efficacy as well.

Monetta and Pell (2007) studied metaphor comprehension in PD patients and found that metaphor interpretation is highly dependent on intact fronto-striatal brain regions, which are compromised, in early PD patients. This suggests that PD patients are less efficient in processing metaphors. Maki et al. (2013) studied metaphor comprehension in patients with mild cognitive decline and Alzheimer's disease patients and found that metaphor comprehension deteriorated with disease progression. Brownell et al. (2012) studied metaphor interpretation in patients with TBI and showed improvement after a metaphor-training program. Pragmatic communication, which includes interpretation of metaphors, relies on higher brain regions as well as intact language systems. Pragmatic communication has been studied in patients with Traumatic Brain Injury (TBI) (McDonald, 2013; McDonald, 1998) schizophrenia (Kircher et al., 2007; Titone et al., 2002) and PD (Monetta and Pell, 2007; Natsopoulos et al., 1997). There is also great interest in studying the neural correlates of metaphor processing (Schmidt and Seger, 2009). Although very little is known about this neural phenomenon, we know that metaphors associated with specific concept types (i.e., predicate metaphors) involve increasingly abstract processing along the lateral temporal cortex and can be analyzed accordingly (Chen et al., 2008). Neuman et al. (2013) developed a set of algorithms capable of detecting conceptual metaphors from text. The algorithms developed by a state-of-the-art automated metaphor detection tool with 71% precision and 27% averaged improvement in prediction (Assaf et al., 2013a; Assaf et al., 2013b; Gandy et al., 2013; Neuman et al., 2013).

Metaphor-Based Diagnosis of and Cognitive Disorders

Like the long-lasting neural network patterns that develop in the hippocampal region of the brain after exposure to a traumatic event (one of the leading causes of PTSD), language and culture play a similar important role in developing long-term neural connections that inform cognition, expression, and behavior. Recent predicate metaphor research, based on the figurative use of terms associated with motion and action, suggests that the processing of these metaphors and their translation into intended meanings is reflected in the anatomical configuration of the brain. Although very little is known about this neural phenomenon, we know that metaphors associated with specific concept types (i.e., predicate metaphors) involve increasingly abstract processing along the lateral temporal cortex and can be analyzed accordingly. (Chen, Evan, Page Widick, Anjan Chatterjee. Functional-anatomical organization of predicate metaphor processing. Brain & Language 107 (2008) 194-202.)

Although languages differ phonetically, concept roots as well as perception of the self, many concept templates are common to all languages. (Wierzbicka, Anna. 1972. *Semantic Primitives*. Frankfurt: Athenaum) These templates are commonly known as conceptual metaphors, and are, simply speaking, concepts that in reality represent other concepts figuratively. (Krennmayr, Tina. (2007) Using Dictionaries in Linguistic Metaphor Identification. VU UniversityAmsterdam. Web: http://www2.english.su.se/nlj/metfest_06_07/Krennmayr_07.pdf Like hippocampal alterations in PTSD victims, neural networks responsible for metaphors tend to be a cornerstone of cognitive processes, and can thus be used in new diagnostic methods that seek to identify cognitive impairments at an early stage. While models of metaphors and algorithms for differentiating non-figurative from figurative language have been investigated in contemporary natural language processing and cognitive sciences literature, their relevance to diagnostics has largely gone overlooked.

Diagnostic systems using metaphors as a foundational concept presuppose the ability to extract meanings from metaphors, as well as determine which metaphor connections should be made by default and which ones should not. Of course, the latter ability relies greatly on cultural context and personal experiences, and while it is possible to determine based on speech context and mind state when a metaphor is being used, metaphor usage instances need to be compared to "cultural controls" as well as healthy controls in order to determine if the instance is normal or aberrant.

In order to use metaphors to diagnose neurodegenerative disorders, three objectives must first be achieved:

1. A fully populated, language-agnostic database of metaphors and their equivalents in other cultures and languages
2. Validated studies and methodologies for the effect of specific disorders (Alzheimer's, dementia, etc.) on the parts of the brain responsible for metaphor processing
3. A multifactor questionnaire, or interview, that coaxes the natural use of several common metaphors and allows clinicians to evaluate whether they are being properly used, and the mind state associated with them.

Each of these factors will ultimately contribute to a metaphor-based "doctor-in-a-box" that can evaluate the correlates of each patient's presentation with those of known neurodegenerative diseases. Much of the founding research for each is already realized, but simply has yet to be assembled to apply metaphors to diagnosis. For instance, the OpenMind-CommonSense database, which catalogues commonsense knowledge based on conceptual primes (i.e., concepts that have no sub-concepts to comprise them). (Howard, N. and H. Lieberman. 2012. "BrainSpace: Relating Neuroscience to Knowledge About Everyday Life," Cognitive Computation. doi: 0.1007/s12559-012-9171-2)

As metaphors simply represent a different configuration of prime-based knowledge, the data from OMCS and similar databases can be reconfigured to reflect commonly accepted metaphors, and then used to test the metaphor recall ability of patients.

The original goal of the program was to gain cross-cultural insights. The research has been focused on an exploratory analysis of differences between the cultures, specifically regarding the source concepts that are used to represent the Program Target concepts. These differences are interpreted via cultural dimensional analysis, using Hofstede's cultural dimensional metrics. Further research objectives may investigate if conceptual metaphor recognition can be used to identify neurodegenerative disorders.

Methodology

How can we develop a metaphor-based computational method to determine the correlates of neurodegenerative disorders and dementia? To do so will require repeated experimentation based on linguistic, cultural, demographics as well as health-related variables. Because metaphors are not intrinsically "commonsense" knowledge, it is important to determine which metaphors should be detectable to an individual. As a result, trials to determine the baseline human cognitive capacity for metaphor processing and recognition should be primarily dependent on cultural and linguistic affiliation. Experiments have the following composition:

- Healthy controls: people with no known cognitive or psychological disorders whose metaphor responses are compared against test groups
- Test group 1: people with a high risk factor for a specific cognitive disorder, such as Alzheimer's, but who haven't manifested any known symptoms yet
- Test group 2: people who may or may not have a diagnosed cognitive impairment, but are presenting early signs of a disorder
- Test group 3: people with diagnosed cognitive impairments with well developed symptoms The use of three test groups with a spectrum of symptom presentations is designed to determine the precise relationship between metaphor processing and cognitive ability as it relates to neurodegenerative disorders. These groups are used in order to eliminate the possibility that reduced metaphor processing ability may simply be a product of one's culture or upbringing, or pre-existing cognitive tendencies to process concepts literally rather than evaluate them for a secondary meaning. In addition, a broad scope of symptoms allows clinicians and analysts to track the progression of metaphor processing ability degeneration without carrying out a years-long experiment, and to tell whether other symptoms progress at the same rate. If metaphor processing is found to degrade at a faster rate, or to occur earlier than the other known symptoms of Alzheimer's and other neurodegenerative disorders, then survey methods that test the patient's ability to recognize and use metaphors in speech and writing will provide a promising means of early detection and superior treatment guidance.

The design of surveys is intended to evaluate metaphor processing should be both open-ended and relatively subtle, so as not to force the patient to think consciously about metaphors. There are three basic means of obtaining such data:

- Directed conversations: subjects are encouraged to make small talk with one another and with those evaluating them, and are directed toward the use of metaphors.
- Reading comprehension: passages whose essential meaning is tied to the use of one or several metaphors are either read to or by subjects, who are then asked their opinion and insights Word-association surveys: subjects are shown metaphor phrases, or word concepts closely related to metaphors, and asked to draw meaning from them. Surveys are a combination of open-answer and multiple-choice questions.

APPENDIX VI: KINNECT TARGET DEVELOPMENT STUDY

Our goal is to develop a suite of vision algorithms to analyze complex goal-directed behaviors from video and depth sensor data. These algorithms will be developed in year 3-5 and are expected to complement body sensors for the analysis of fine movements but, in addition, they will also allow us to analyze behaviors for a large repertoire of goal directed actions. We will combine recent innovations in data-intensive machine learning with novel depth sensor technologies to build automated systems with unprecedented visual capabilities. Serre Labs will contribute their unique expertise in large-scale automated analysis. Thomas Serre is the co-director of Brown's behavioral core facility, which is the first fully automated behavioral core. The core currently processes over 4,000 hours of behavioral videos monthly corresponding to over 100,000 hours of human manual work. Serre has lead the development of an automated computer vision system for the analysis of rodent behaviors in their homecage. The system is capable to discriminate between about a dozen homecage behaviors at a level undistinguishable from that of human annotators (Jhuang et al. 2010). Initial results suggest that the approach is applicable to facial expression recognition (Jhuang et al. 2007). Recent extensions of the system have been already tested on human actions (Kuehne et al., 2011 2014). The latest iteration of the system is able to discriminate between a dozen cooking activities in people's own kitchen (see FIGS. 29 and 30 for sample frames) at a level of accuracy of about 75% (chance level 10%) significantly outperforming state-of-the-art approaches. The system is capable of recognizing actions at multiple levels from the coarse level of cooking activity (e.g., making pancakes) to fine motor behaviors (e.g., opening bottle).

Figure 29:
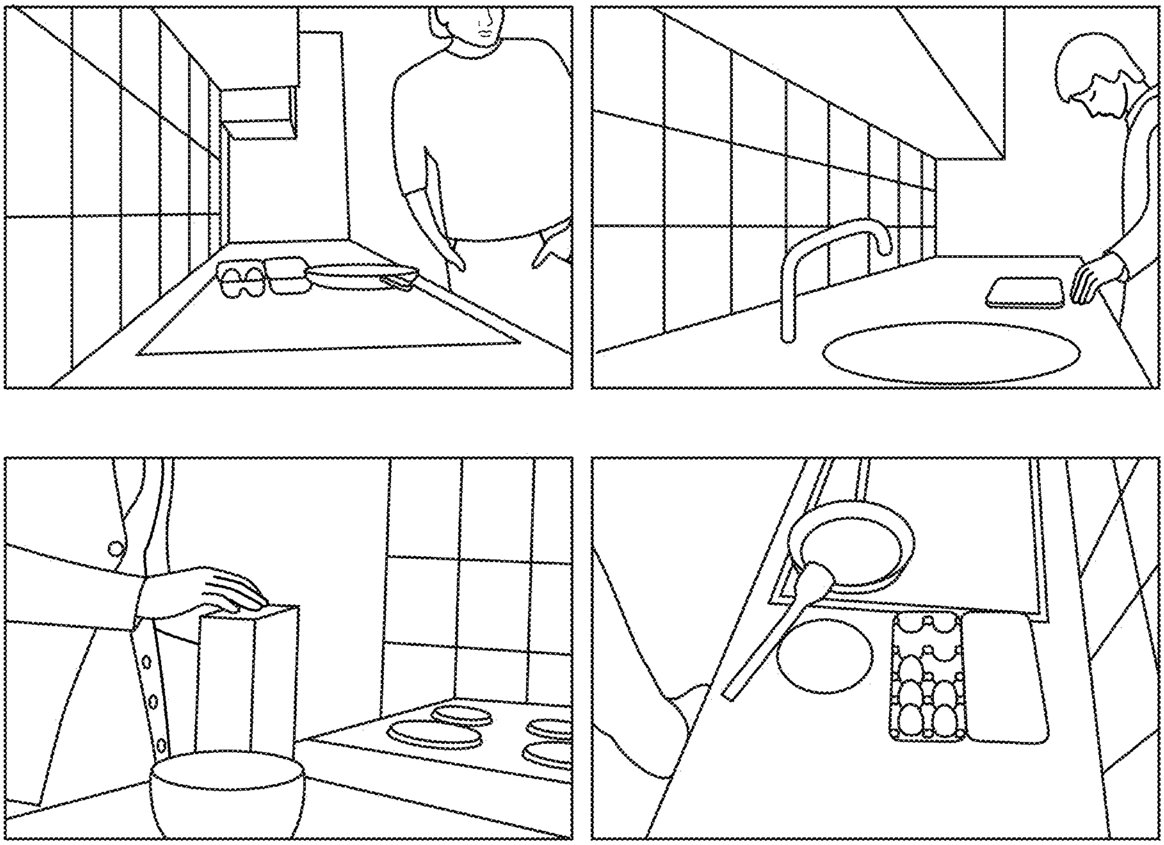
FIG. 29 shows sample frames from the Breakfast database collected in Serre's group.
Figure 30:
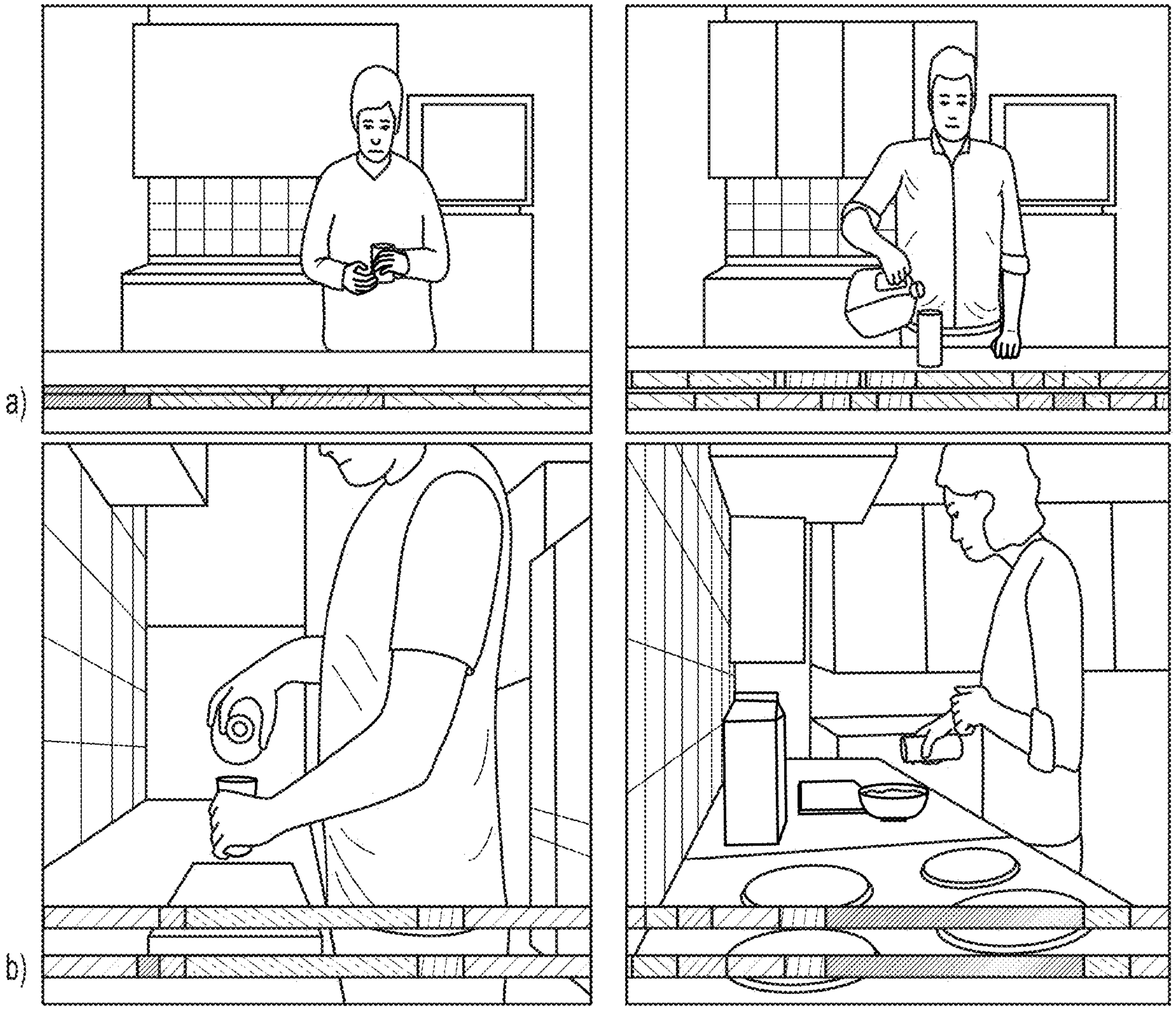
FIG. 30 shows sample results for the segmentation of a video clip into action units.

FIG. 29 shows sample frames from the Breakfast database collected in Serre's group (see Kuehne et al. 2014). FIG. 30 shows sample results for the segmentation of a video clip into action units for: a) activities from the ADL dataset ("use phone" and "drink water"), b) for activities from our own Breakfast dataset ("prepare juice" and "prepare scrambled eggs"). The upper color bar shows the ground-truth and the lower bar shows the automated parsing by the computer vision system.

More recently, Serre's group has started to work with the MICROSOFT™ KINECT™ and other depth sensors. Such sensors are inexpensive (<100$) and permit the capture of 3D data under any ambient light conditions. The group is already using depth sensors in their "smart playroom" (see FIG. 31). The "smart playroom" is used to try to automatically discover behavioral markers to help scientists diagnose autism and other mental disorders earlier than currently possible. The room is currently equipped with several video cameras and KINECT™ sensors in order to track children as they roam around the room playing with toys. Combined with Serre's original video-based approach, these sensors will enable the development of a new breed of vision algorithms for the monitoring and analysis of human behaviors from fine movements to complex goal-directed actions.

Figure 31:
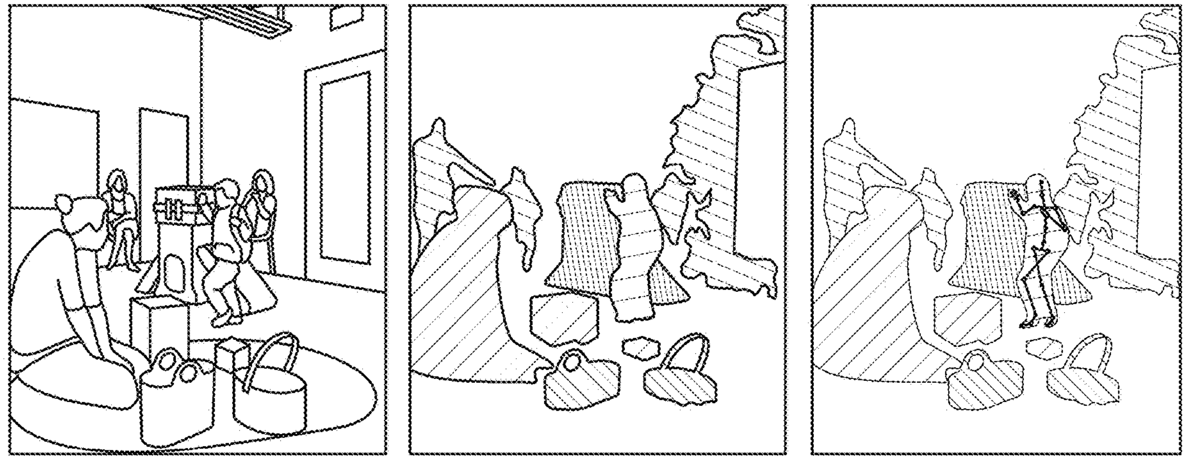
FIG. 31 shows an example of using the KINECT™ sensors.

FIG. 31 shows an example of using the KINECT™ sensors in the smart playroom at Brown. Serre and colleagues are currently using video (left) and depth (middle) sensors for the automated analysis of children's behavior in the smart playroom. The KINECT™ sensor can be used to recover joint locations and associated kinematics (right), which is then combined with.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A computer-implemented method for detecting a disease condition comprising:

receiving a plurality of data streams from a plurality of sensors, each of the plurality of data streams representing a measurement of a brain activity, wherein the measurement comprises modalities including electroencephalographic monitoring, linguistic assessment, behavioral tracking, facial feature analysis, mood state, cognitive state, language analysis, speech and vocal impairments, modes of speaking, and/or body movement;

integrating the plurality of data streams into a same coordinate system, creating an integrated data stream;

constructing, for the integrated data stream a wavelet function representing an indication of the cognitive state or a disease condition to form at least one fundamental code unit of a brain code corresponding to the cognitive state or the disease condition;

matching the at least one fundamental code unit of the brain code to at least one of a plurality of different fundamental code units of the brain code; and outputting and storing the matched at least one fundamental code unit in non-transitory storage.

2. The method of claim 1, further comprising constructing another wavelet function representing patterns in each of the plurality of data streams corresponding to the cognitive state or the disease condition for each of the plurality of data streams.

3. The method of claim 1, further comprising processing at least some data of the plurality of data streams using a Hidden Markov Model to predict unknown states of the modalities from observed states of the modalities, wherein a Viterbi algorithm is used to determine a sequence of the unknown states that makes the observed states most probable.

4. The method of claim 1, wherein the received plurality of data streams are integrated by performing pattern analysis comprising at least one of language analysis using machine learning, syntactic structure identification, multilayered perceptron neural networks, machine translation processes, case-based reasoning, analogy-based reasoning, speech-based cognitive assessment, mood state indicator, linguistic-axiological input/output, and mind default axiology.

5. The method of claim 1, wherein the linguistic assessment determines dysphonia features including a variation of fundamental frequency, at least one measure of amplitude, a noise to harmonics ratio, a harmonics to noise ratio, detrended fluctuation, and/or pitch period entropy.

6. The method of claim 1, wherein the facial feature analysis comprises determining whether a captured image illustrates at least one emotion of a plurality of emotion categories using a binary classifier.

7. The method of claim 1, wherein the facial feature analysis processes at least one facial characteristic point, wherein the at least one facial characteristic point comprises a blink rate, a distance between a right eye and a left eye, a distance between an upper line of the right eye and a lower line of the right eye, a distance between an upper line of the left eye and a lower line of the left eye, and/or a distance between a left eyebrow and a right eyebrow.

8. The method of claim 1, further comprising normalizing the plurality of data streams against a fundamental frequency range, creating a unitary pseudo frequency.

9. The method of claim 1, further comprising linking the plurality of data streams using machine learning and/or unitary math.

10. The method of claim 1, wherein the wavelet function is a Morlet wavelet.

11. A computer program product for detecting a disease condition, the computer program product comprising a non-transitory computer readable storage having program instructions embodied therewith, the program instructions executable by a computer, to cause the computer to perform a method comprising:

receiving a plurality of data streams from a plurality of sensors, each data stream representing a measurement of a brain activity, wherein the measurement comprises modalities including at least a plurality of electroencephalographic monitoring, linguistic assessment, behavioral tracking, facial feature analysis, mood state, cognitive state, language analysis, speech and vocal impairments, modes of speaking, and/or body movement;

integrating the received plurality of data streams into a same coordinate system, creating an integrated data stream;

constructing, for the integrated data stream a wavelet function representing an indication of the cognitive state or the disease condition to form at least one fundamental code unit of a brain code corresponding to the cognitive state or the disease condition;

matching the at least one fundamental code unit of the brain code to at least one of a plurality of different fundamental code units of the brain code; and outputting and storing the matched at least one fundamental code unit in non-transitory storage.

12. The computer program product of claim 11, wherein the program instructions further cause the computer to process at least some data of the plurality of data streams using a Hidden Markov Model to predict unknown states of the modalities from known states of the modalities.

13. The computer program product of claim 11, wherein the program instructions further cause the computer to construct another wavelet function representing patterns in each of the plurality of data streams corresponding to the cognitive state or the disease condition for each of the plurality of data streams.

14. The computer program product of claim 11, wherein the received plurality of data streams are integrated by performing pattern analysis comprising at least one of language analysis using machine learning, syntactic structure identification, multilayered perceptron neural networks, machine translation processes, case-based reasoning, analogy-based reasoning, speech-based cognitive assessment, mood state indicator, linguistic-axiological input/output, and mind default axiology.

15. The computer program product of claim 11, wherein the linguistic assessment determines dysphonia features including a variation of fundamental frequency, at least one measure of amplitude, a noise to harmonics ratio, a harmonics to noise ratio, detrended fluctuation, and/or pitch period entropy.

16. The computer program product of claim 11, wherein the program instructions further cause the computer to link the plurality of data streams using machine learning and/or unitary math.

17. The computer program product of claim 11, wherein the wavelet function is a Morlet wavelet.

18. A computer-implemented method for detecting a disease condition comprising:

receiving a plurality of data streams from a plurality of sensors, each of the plurality of data streams representing a measurement of a brain activity, wherein the measurement comprises modalities including electroencephalographic monitoring, linguistic assessment, behavioral tracking, facial feature analysis, mood state, cognitive state, language analysis, speech and vocal impairments, modes of speaking, and/or body movement;

linking the plurality of data streams using machine learning and/or unitary math;

processing at least some data of the plurality of data streams using a Hidden Markov Model to predict unknown states of the modalities from observed states of the modalities;

integrating the plurality of data streams into a same coordinate system by performing pattern analysis comprising at least one of language analysis using machine learning, syntactic structure identification, multilayered perceptron neural networks, machine translation processes, case-based reasoning, analogy-based reasoning, speech-based cognitive assessment, mood state indicator, linguistic-axiological input/output, and mind default axiology, creating an integrated data stream;

constructing, for the integrated data stream a wavelet function representing an indication of the cognitive state or the disease condition to form at least one fundamental code unit of a brain code corresponding to the cognitive state or the disease condition;

constructing another wavelet function representing patterns in each of the plurality of data streams corresponding to the cognitive state or the disease condition for each of the plurality of data streams;

matching the at least one fundamental code unit of the brain code to at least one of a plurality of different fundamental code units of the brain code; and outputting and storing the matched at least one fundamental code unit in non-transitory storage.

19. The method of claim 18, wherein the disease condition is posttraumatic stress disorder.

* * * * *